US009551036B2

(12) United States Patent
Shaul et al.

(10) Patent No.: US 9,551,036 B2
(45) Date of Patent: Jan. 24, 2017

(54) METABOLIC GENE MESENCHYMAL SIGNATURES AND USES THEREOF

(71) Applicant: Whitehead Institute for Biomedical Research, Cambridge, MA (US)

(72) Inventors: Yoav D. Shaul, Brookline, MA (US); David M. Sabatini, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/189,226

(22) Filed: Feb. 25, 2014

(65) Prior Publication Data

US 2014/0357693 A1 Dec. 4, 2014

Related U.S. Application Data

(60) Provisional application No. 61/937,399, filed on Feb. 7, 2014, provisional application No. 61/768,922, filed on Feb. 25, 2013.

(51) Int. Cl.
| | | |
|---|---|---|
| C12N 15/11 | (2006.01) | |
| C12Q 1/68 | (2006.01) | |
| G01N 33/50 | (2006.01) | |
| C12N 15/113 | (2010.01) | |

(52) U.S. Cl.
CPC .......... *C12Q 1/6886* (2013.01); *C12N 15/113* (2013.01); *G01N 33/5011* (2013.01); *G01N 33/5023* (2013.01); *C12N 2320/12* (2013.01); *C12N 2330/51* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 2006/0121498 A1* | 6/2006 | Murphy | ............ | C07K 14/4747 435/6.14 |
| 2012/0071350 A1* | 3/2012 | Damelin | .............. | C12N 5/0695 506/10 |
| 2013/0028899 A1* | 1/2013 | Sarkar | ................ | A61K 31/7105 424/138.1 |
| 2013/0324570 A1* | 12/2013 | Hansen | .............. | A61K 31/4741 514/291 |
| 2014/0303133 A1* | 10/2014 | Pietenpol | ............. | C12Q 1/6886 514/183 |
| 2015/0037401 A1* | 2/2015 | Chang | ................. | C12N 15/113 424/450 |

FOREIGN PATENT DOCUMENTS

WO WO 2009/126310 A2 10/2009

OTHER PUBLICATIONS

Nukatsuka et al., Antimetastatic and anticancer activity of S-1, a new oral dihydropyrimidine-dehydrogenase-inhibiting fluoropyrimidine, alone and in combination with paclitaxel in an orthotopically implanted human breast cancer model, 2004, International Journal of Oncology, vol. 25, pp. 1531-1536.*
Sellappan et al., Lineage infidelity of MDA-MB-435 cells: expression of melanocyte proteins in a breast cancer cell line, 2004, Cancer Research, vol. 64, pp. 3479-3485.*
Kalluri et al., The basics of epithelial-mesenchymal transition, 2009, The Journal of Clinical Investigation, vol. 119, pp. 1420-1428.*
Ciccolini et al., A simple and rapid high-performance liquid chromatographic (HPLC) method for 5-fluorouracil (5-FU) assay in plasma and possible detection of patients with impaired dihydropyrimidine dehydrogenase (DPD) activity, 2004, Journal of Clinical Pharmacy and Therapeutics, vol. 29, pp. 307-315.*
Aigner et al., The transcription factor ZEB1 (deltaEF1) promotes tumour cell dedifferentiation by repressing master regulators of epithelial polarity. Oncogene. Oct. 25, 2007;26(49):6979-88. Epub May 7, 2007.
Amstutz et al., Dihydropyrimidine dehydrogenase gene as a major predictor of severe 5-fluorouracil toxicity. Pharmacogenomics. Sep. 2011;12(9):1321-36. doi: 10.2217/pp. 11.72.
Barretina et al., The Cancer Cell Line Encyclopedia enables predictive modelling of anticancer drug sensitivity. Nature. Mar. 28, 2012;483(7391):603-7. doi: 10.1038/nature11003. Erratum in: Nature. Dec. 13, 2012;492(7428):290.
Barrett et al., NCBI GEO: mining tens of millions of expression profiles—database and tools update. Nucleic Acids Res. Jan. 2007;35(Database issue):D760-5. Epub Nov. 11, 2006.
Brabletz, To differentiate or not—routes towards metastasis. Nat Rev Cancer. May 11, 2012;12(6):425-36. doi: 10.1038/nrc3265.
Büchel et al., LC-MS/MS method for simultaneous analysis of uracil, 5,6-dihydrouracil, 5-fluorouracil and 5-fluoro-5,6-dihydrouracil in human plasma for therapeutic drug monitoring and toxicity prediction in cancer patients. Biomed Chromatogr. Jan. 2013;27(1):7-16. doi: 10.1002/bmc.2741. Epub Mar. 27, 2012.
Cantor et al., Cancer cell metabolism: one hallmark, many faces. Cancer Discov. Oct. 2012;2(10):881-98. doi: 10.1158/2159-8290.CD-12-0345. Epub Sep. 25, 2012.
Carey et al., Triple-negative breast cancer: disease entity or title of convenience? Nat Rev Clin Oncol. Dec. 2010;7(12):683-92. doi: 10.1038/nrclinonc.2010.154. Epub Sep. 28, 2010.
Chaneton et al., Serine is a natural ligand and allosteric activator of pyruvate kinase M2. Nature. Nov. 15, 2012;491(7424):458-62. doi: 10.1038/nature11540. Epub Oct. 14, 2012. Erratum in: Nature. Apr. 18, 2013;496(7445):386.
Dai et al., Evolving gene/transcript definitions significantly alter the interpretation of GeneChip data. Nucleic Acids Res. Nov. 10, 2005;33(20):e175.

(Continued)

*Primary Examiner* — Dana Shin
(74) *Attorney, Agent, or Firm* — Wolf, Greenfield & Sacks, P.C.

(57) ABSTRACT

Aspects of the invention relate to methods and compositions for characterizing or modulating the expression of metabolic mesenchymal genes. In some embodiments, methods for assessing the expression of metabolic mesenchymal genes and related gene signatures are provided that are useful for cancer classification, prognosis, diagnosis, or treatment selection.

17 Claims, 69 Drawing Sheets

(56) References Cited

OTHER PUBLICATIONS

Dang et al., Cancer-associated IDH1 mutations produce 2-hydroxyglutarate. Nature. Dec. 10, 2009;462(7274):739-44. doi: 10.1038/nature08617.

Dolinnaya et al., Thymidine glycol: the effect on DNA molecular structure and enzymatic processing. Biochimie. Feb. 2013;95(2):134-47. doi: 10.1016/j.biochi.2012.09.008. Epub Sep. 20, 2012.

Dontu et al., In vitro propagation and transcriptional profiling of human mammary stem/progenitor cells. Genes Dev. May 15, 2003;17(10):1253-70.

Elbein et al., Molecular screening of the human glutamine-fructose-6-phosphate amidotransferase 1 (GFPT1) gene and association studies with diabetes and diabetic nephropathy. Mol Genet Metab. Aug. 2004;82(4):321-8.

Elenbaas et al., Human breast cancer cells generated by oncogenic transformation of primary mammary epithelial cells. Genes Dev. Jan. 1, 2001;15(1):50-65.

Ezzeldin et al., Dihydropyrimidine dehydrogenase deficiency, a pharmacogenetic syndrome associated with potentially life-threatening toxicity following 5-fluorouracil administration. Clin Colorectal Cancer. Sep. 2004;4(3):181-9.

Ferry et al., S32826, a nanomolar inhibitor of autotaxin: discovery, synthesis and applications as a pharmacological tool. J Pharmacol Exp Ther. Dec. 2008;327(3):809-19. doi: 10.1124/jpet.108.141911. Epub Aug. 28, 2008.

Gottlieb et al., Mitochondrial tumour suppressors: a genetic and biochemical update. Nat Rev Cancer. Nov. 2005;5(11):857-66.

Hanahan et al., Hallmarks of cancer: the next generation. Cell. Mar. 4, 2011;144(5):646-74. doi: 10.1016/j.cell.2011.02.013.

He et al., Citric acid cycle intermediates as ligands for orphan G-protein-coupled receptors. Nature. May 13, 2004;429(6988):188-93.

Hensley et al., Glutamine and cancer: cell biology, physiology, and clinical opportunities. J Clin Invest. Sep. 3, 2013;123(9):3678-84. doi: 10.1172/JCI69600. Epub Sep. 3, 2013.

Hsu et al., Cancer cell metabolism: Warburg and beyond. Cell. Sep. 5, 2008;134(5):703-7. doi: 10.1016/j.cell.2008.08.021.

Hu et al., Heterogeneity of tumor-induced gene expression changes in the human metabolic network. Nat Biotechnol. Jun. 2013;31(6):522-9. doi: 10.1038/nbt.2530. Epub Apr. 21, 2013.

Ide et al., Dihydrothymidine and thymidine glycol triphosphates as substrates for DNA polymerases: differential recognition of thymine C5-C6 bond saturation and sequence specificity of incorporation. Nucleic Acids Res. Dec. 9, 1988;16(23):11339-54.

Ide et al., Synthesis of dihydrothymidine and thymidine glycol 5'-triphosphates and their ability to serve as substrates for *Escherichia coli* DNA polymerase I. Biochemistry. Feb. 10, 1987;26(3):964-9.

Iwamoto, Diagnosis and treatment of Ewing's sarcoma. Jpn J Clin Oncol. Feb. 2007;37(2):79-89. Epub Feb. 1, 2007.

Jaggupilli et al., Significance of CD44 and CD24 as cancer stem cell markers: an enduring ambiguity. Clin Dev Immunol. 2012;2012:708036. doi: 10.1155/2012/708036. Epub May 30, 2012.

Kao et al., Molecular profiling of breast cancer cell lines defines relevant tumor models and provides a resource for cancer gene discovery. PLoS One. Jul. 3, 2009;4(7):e6146. doi: 10.1371/journal.pone.0006146.

Lehmann et al., Identification of human triple-negative breast cancer subtypes and preclinical models for selection of targeted therapies. J Clin Invest. Jul. 2011;121(7):2750-67. doi: 10.1172/JCI45014.

Li et al., Cell surface glycan alterations in epithelial mesenchymal transition process of Huh7 hepatocellular carcinoma cell. PLoS One. Aug. 20, 2013;8(8):e71273. doi: 10.1371/journal.pone.0071273. eCollection 2013.

Li et al., Up-regulation of miR-200 and let-7 by natural agents leads to the reversal of epithelial-to-mesenchymal transition in gemcitabine-resistant pancreatic cancer cells. Cancer Res. Aug. 15, 2009;69(16):6704-12. doi: 10.1158/0008-5472.CAN-09-1298. Epub Aug. 4, 2009.

Locasale et al., Phosphoglycerate dehydrogenase diverts glycolytic flux and contributes to oncogenesis. Nat Genet. Jul. 31, 2011;43(9):869-74. doi: 10.1038/ng.890.

Lohkamp et al., Insights into the mechanism of dihydropyrimidine dehydrogenase from site-directed mutagenesis targeting the active site loop and redox cofactor coordination. Biochim Biophys Acta. Dec. 2010;1804(12):2198-206. doi: 10.1016/j.bbapap.2010.08.014. Epub Sep. 8, 2010.

Lu et al., IDH mutation impairs histone demethylation and results in a block to cell differentiation. Nature. Feb. 15, 2012;483(7390):474-8. doi: 10.1038/nature10860.

Ma et al., O-GlcNAc in cancer biology. Amino Acids. Oct. 2013;45(4):719-33. doi: 10.1007/s00726-013-1543-8. Epub Jul. 9, 2013.

Mani et al., The epithelial-mesenchymal transition generates cells with properties of stem cells. Cell. May 16, 2008;133(4):704-15. doi: 10.1016/j.cell.2008.03.027.

Mizutani et al., Significance of dihydropyrimidine dehydrogenase activity in renal cell carcinoma. Eur J Cancer. Mar. 2003;39(4):541-7.

Mootha et al., PGC-1alpha-responsive genes involved in oxidative phosphorylation are coordinately downregulated in human diabetes. Nat Genet. Jul. 2003;34(3):267-73.

Morel et al., Generation of breast cancer stem cells through epithelial-mesenchymal transition. PLoS One. Aug. 6, 2008;3(8):e2888. doi: 10.1371/journal.pone.0002888.

Neve et al., A collection of breast cancer cell lines for the study of functionally distinct cancer subtypes. Cancer Cell. Dec. 2006;10(6):515-27.

Nieto et al., The epithelial-mesenchymal transition under control: global programs to regulate epithelial plasticity. Semin Cancer Biol. Oct. 2012;22(5-6):361-8. doi: 10.1016/j.semcancer.2012.05.003. Epub May 18, 2012.

Nieto, The ins and outs of the epithelial to mesenchymal transition in health and disease. Annu Rev Cell Dev Biol. 2011;27:347-76. doi: 10.1146/annurev-cellbio-092910-154036. Epub Jul. 8, 2011.

Nomura et al., Monoacylglycerol lipase regulates a fatty acid network that promotes cancer pathogenesis. Cell. Jan. 8, 2010;140(1):49-61. doi: 10.1016/j.cell.2009.11.027.

Offer et al., Phenotypic profiling of DPYD variations relevant to 5-fluorouracil sensitivity using real-time cellular analysis and in vitro measurement of enzyme activity. Cancer Res. Mar. 15, 2013;73(6):1958-68. doi: 10.1158/0008-5472.CAN-12-3858. Epub Jan. 17, 2013.

Onganer et al., Neuronal characteristics of small-cell lung cancer. Br J Cancer. Nov. 28, 2005;93(11):1197-201.

Park et al. Characterization of cell lines established from human hepatocellular carcinoma. Int J Cancer. Jul. 28, 1995;62(3):276-82.

Park et al., Snail1 is stabilized by O-GlcNAc modification in hyperglycaemic condition. EMBO J. Nov. 17, 2010;29(22):3787-96. doi: 10.1038/emboj.2010.254. Epub Oct. 19, 2010.

Peinado et al., Snail, Zeb and bHLH factors in tumour progression: an alliance against the epithelial phenotype? Nat Rev Cancer. Jun. 2007;7(6):415-28. Epub May 17, 2007.

Possemato et al., Functional genomics reveal that the serine synthesis pathway is essential in breast cancer. Nature. Aug. 18, 2011;476(7360):346-50. doi: 10.1038/nature10350.

Samadi et al., Regulation of lysophosphatidate signaling by autotaxin and lipid phosphate phosphatases with respect to tumor progression, angiogenesis, metastasis and chemo-resistance. Biochimie. Jan. 2011;93(1):61-70. doi: 10.1016/j.biochi.2010.08.002. Epub Aug. 13, 2010.

Scheel et al., Phenotypic plasticity and epithelial-mesenchymal transitions in cancer and normal stem cells? Int J Cancer. Nov. 15, 2011;129(10):2310-4. doi: 10.1002/ijc.26311. Epub Aug. 29, 2011.

Schulze et al., How cancer metabolism is tuned for proliferation and vulnerable to disruption. Nature. Nov. 15, 2012;491(7424):364-73. doi: 10.1038/nature11706. Review. Erratum in: Nature. Feb. 7, 2013;494(7435):130.

(56) References Cited

OTHER PUBLICATIONS

Singh et al., EMT, cancer stem cells and drug resistance: an emerging axis of evil in the war on cancer. Oncogene. Aug. 26, 2010;29(34):4741-51. doi: 10.1038/onc.2010.215. Epub Jun. 7, 2010.

Tam et al., Protein kinase C α is a central signaling node and therapeutic target for breast cancer stem cells. Cancer Cell. Sep. 9, 2013;24(3):347-64. doi: 10.1016/j.ccr.2013.08.005.

Taube et al., Core epithelial-to-mesenchymal transition interactome gene-expression signature is associated with claudin-low and metaplastic breast cancer subtypes. Proc Natl Acad Sci U S A. Aug. 31, 2010;107(35):15449-54. doi: 10.1073/pnas.1004900107. Epub Aug. 16, 2010. Erratum in: Proc Natl Acad Sci U S A. Nov. 2, 2010;107(44):19132.

Tennant et al., Targeting metabolic transformation for cancer therapy. Nat Rev Cancer. Apr. 2010;10(4):267-77. doi: 10.1038/nrc2817. Epub Mar. 19, 2010.

Ulanovskaya et al., NNMT promotes epigenetic remodeling in cancer by creating a metabolic methylation sink. Nat Chem Biol. May 2013;9(5):300-6. doi: 10.1038/nchembio.1204. Epub Mar. 3, 2013.

Van Gennip et al., Defects of pyrimidine degradation: clinical, molecular and diagnostic aspects. Adv Exp Med Biol. 2000;486:233-41.

Van Kuilenburg et al., Dihydropyrimidinase deficiency: Phenotype, genotype and structural consequences in 17 patients. Biochim Biophys Acta. Jul.-Aug. 2010;1802(7-8):639-48. doi: 10.1016/j.bbadis.2010.03.013. Epub Apr. 1, 2010.

Van Kuilenburg et al., Novel disease-causing mutations in the dihydropyrimidine dehydrogenase gene interpreted by analysis of the three-dimensional protein structure. Biochem J. May 15, 2002;364(Pt 1):157-63.

Van Kuilenburg et al., β-ureidopropionase deficiency: phenotype, genotype and protein structural consequences in 16 patients. Biochim Biophys Acta. Jul. 2012;1822(7):1096-108. doi: 10.1016/j.bbadis.2012.04.001.

Vander Heiden et al., Understanding the Warburg effect: the metabolic requirements of cell proliferation. Science. May 22, 2009;324(5930):1029-33. doi: 10.1126/science.1160809.

Verhaak et al., Integrated genomic analysis identifies clinically relevant subtypes of glioblastoma characterized by abnormalities in PDGFRA, IDH1, EGFR, and NF1. Cancer Cell. Jan. 19, 2010;17(1):98-110. doi: 10.1016/j.ccr.2009.12.020.

Ward et al., Metabolic reprogramming: a cancer hallmark even warburg did not anticipate. Cancer Cell. Mar. 20, 2012;21(3):297-308. doi: 10.1016/j.ccr.2012.02.014.

Yoo et al., Identification of genes conferring resistance to 5-fluorouracil. Proc Natl Acad Sci U S A. Aug. 4, 2009;106(31):12938-43. doi: 10.1073/pnas.0901451106. Epub Jul. 21, 2009.

Zhang et al., Common variants in glutamine:fructose-6-phosphate amidotransferase 2 (GFPT2) gene are associated with type 2 diabetes, diabetic nephropathy, and increased GFPT2 mRNA levels. J Clin Endocrinol Metab. Feb. 2004;89(2):748-55.

Zhang et al., Glycine decarboxylase activity drives non-small cell lung cancer tumor-initiating cells and tumorigenesis. Cell. Jan. 20, 2012;148(1-2):259-72. doi: 10.1016/j.cell.2011.11.050. Epub Jan. 5, 2012. Erratum in: Cell. Mar. 2, 2012;148(5):1066. Mitchell, Wayne [added].

Zhi et al., Potential prognostic biomarker CD73 regulates epidermal growth factor receptor expression in human breast cancer. IUBMB Life. Nov. 2012;64(11):911-20. doi: 10.1002/iub.1086.

Submission. DPYD. HGNC:3012. Retrieved from http://www.genenames.org/cgi-bin/gene_symbol_report?hgnc_id=3012 on Feb. 18, 2016.

Submission. MDA-MB-435S (ATCC® HTB-129™). *Homo sapiens*, human. 1976.

Holliday et al., Choosing the right cell line for breast cancer research. Breast Cancer Res. Aug. 12, 2011;13(4):215. doi: 10.1186/bcr2889.

Prasad et al., Continued use of MDA-MB-435, a melanoma cell line, as a model for human breast cancer, even in year, 2014. Nature. 2015;1.

Scudellari, A case of mistaken identity. The Scientist. Sep. 16, 2008. Retrieved from http://www.the-scientist.com/?articles.view/articleNo/26748/title/A-case-of-mistaken-identity/ on Feburary 18, 2016.

\* cited by examiner

B.

D.

E.

F.

A.

B.

B.

C.

D.

| Mesenchymal genes | Metabolic genes | Random Metabolic genes |
|---|---|---|
| ZEB1<br>NT5E<br>SNAI2<br>SNAI1<br>CD44<br>Vim<br><br>6/12 | DPYD<br>PPAP2B<br>MICAL2<br>PPAPDC1A<br>GPX8<br>MGST1<br>PLCB4<br>COX7A1<br>EXT1<br>DSEL    16/43<br>B3GNT9<br>CA12<br>HS3ST3A1<br>MSRB3<br>SULF1<br>UAP1 | ELOVL5<br>HNMT<br><br>2/16 |

| Pathways | Metabolic Enzymes | ANTIMETABOLITE |
|---|---|---|
| Universal Signature | GART | Pemetrexed |
| | HPRT1 | Mercaptopurine |
| | TYMS | 5-FU, Capecitabine, Gemcitabine |
| | RRM1 | Gemcitabine, Clofarabine, Cladribine, Hydroxyurea, Fludarabine |
| | RRM2 | Cladribine |
| Non in Universal Signature | DHFR | Methotrexate |
| | CMPK | Gemcitabine |
| | DNMT1 | Decitabine |

Figure 10 Continued

C. Mesenchymal Derived Cluster

FDR q-value= 0

Enrichment plot :EMT

D.

B.

D.

| Control genes | Mesenchymal genes | Metabolic genes | | Random Metabolic genes |
|---|---|---|---|---|
| GFP | CD44 | AK5 | GPX8 | ACLY |
| LacZ | CDH1 | AKR1B1 | GXYLT2 | AGK |
| LUCIFERASE | FOXC2 | AOX1 | HAS2 | ALDH1L1 |
| RFP | GCG | ARSJ | HS3ST3A1 | ARG2 |
| | NT5E | B3GNT9 | MGLL | CDA |
| | SNAI1 | BCAT1 | MGST1 | DIO1 |
| | SNAI2 | CA12 | MICAL2 | ELOVL5 |
| | TGFB1 | CHI3L1 | MME | GCNT3 |
| | TWIST1 | COX7A1 | MSRB3 | GGH |
| | VIM | CYBRD1 | NNMT | GPX3 |
| | ZEB1 | CYP1B1 | PAM | HNMT |
| | ZEB2 | DDAH1 | PAPSS2 | MAOB |
| | | DPYD | PDE1C | NUDT5 |
| | | DSE | PLCB4 | RRM1 |
| | | DSEL | PPAP2B | ST6GALNAC2 |
| | | ENPP2 | PPAPDC1A | TYMS |
| | | EXT1 | PTGR1 | |
| | | GALNT10 | SPHK1 | |
| | | GBE1 | SULF1 | |
| | | GFPT2 | UAP1 | |
| | | GLT8D2 | UGCG | |
| | | | QPRT | |

METABOLIC GENE MESENCHYMAL SIGNATURES AND USES THEREOF

RELATED APPLICATIONS

This application claims priority under 35 U.S.C. §119(e) to U.S. Provisional Application Ser. No. 61/768,922, entitled "METABOLIC GENE MESENCHYMAL SIGNATURES AND USES THEREOF" filed on Feb. 25, 2013, and to U.S. Provisional Application Ser. No. 61/937,399, entitled "METABOLIC GENE MESENCHYMAL SIGNATURES AND USES THEREOF" filed on Feb. 7, 2014, which are herein incorporated by reference in their entirety.

BACKGROUND OF INVENTION

The differentiation states of cancer cells influence their malignant properties. Carcinoma cells lie along a continuum of less- and more-differentiated states. When taken from the same tumor, cancer cells in distinct states can have very different functional properties. For instance, in comparison to other cells in the same tumor, cancer stem cells (CSCs) efficiently seed new tumors, invade host tissues, and survive without cell-to-cell or cell-to-matrix attachments. However, basis for intrinsic therapeutic resistance, invasiveness, and other properties CSCs remains minimally understood.

SUMMARY OF INVENTION

Aspects of the invention relate to methods and compositions for characterizing or modulating the expression of human genes involved in various metabolic pathways. In some embodiments, it has been found that certain cancer cell lines demonstrate a gene signature (referred to herein as metabolic gene mesenchymal signature) based on the expression of human genes involved in metabolic pathways that is indicative of one or more mesenchymal characteristics in cells. In some embodiments, analysis of expression or activity of the metabolic gene signature in cancers is useful for a variety of purposes, including, for example, in cancer classification, prognosis, diagnosis, or treatment selection. According to some aspects of the invention is has been found that certain metabolic mesenchymal genes modulate epithelial to mesenchymal transitions (EMTs) in cells, including normal cells and cancer cells, and thus influence the generation of stem cells and CSCs. Accordingly, in some embodiments, agents and related methods are provided for targeting the expression or activity of metabolic mesenchymal genes to inhibit or reverse EMTs. In some embodiments, related methods for treating cancer are provided. In some embodiments, agents and related methods are provided for targeting the expression or activity of metabolic mesenchymal genes to induce EMTs. In some embodiments, related methods for producing stem cells, e.g., for regenerative medicine or research purposes, are provided.

Aspects of the invention provide methods for evaluating a cancer of non-mesenchymal origin in a subject. In some embodiments, the methods involve (a) subjecting a sample of the cancer obtained from the subject to a gene expression analysis, wherein the gene expression analysis comprises determining expression levels of one or more metabolic mesenchymal genes in the cancer using an expression level determining system; and (b) comparing the expression levels determined in (a) to reference expression levels of the one or more metabolic mesenchymal genes in appropriate reference cells. In some embodiments, the results of the comparison in (b) are indicative of the extent to which cells in the cancer have undergone a epithelial-to-mesenchymal transition. In some embodiments, the results of the comparison in (b) are indicative of the presence of cancer stem cells in the cancer. In some embodiments, the results of the comparison in (b) are indicative of the aggressiveness of the cancer.

Aspects of the invention provide methods for determining the presence of a cancer of non-mesenchymal origin in a subject. In some embodiments, the methods involve (a) obtaining a tissue sample from a region of a subject suspected of containing the cancer; and (b) subjecting the tissue sample to a gene expression analysis, wherein the gene expression analysis comprises determining expression levels of one or more metabolic mesenchymal genes in the sample using an expression level determining system, and wherein the results of the analysis are indicative of whether the subject has a cancer of non-mesenchymal origin. Aspects of the invention provide methods for diagnosing a subject as having a carcinoma. In some embodiments, the methods involve (a) subjecting a tissue sample obtained from the subject to a pathological examination, wherein the results of the pathological examination are indicative of whether the tissue sample comprises a carcinoma, optionally wherein the pathological examination is further indicative of whether the tissue sample comprises cancer stem cells; (b) subjecting the tissue sample to a gene expression analysis, wherein the gene expression analysis comprises determining expression levels of one or more metabolic mesenchymal genes in the sample using an expression level determining system, and wherein the results of the analysis are indicative of whether the tissue sample contains cancer stem cells; and (c) diagnosing the subject as having a carcinoma containing cancer stem cells based on the results of (a) and (b). In some embodiments, the pathological examination comprises performing a microscopic examination on cells of the tissue sample, and determining whether the tissue sample comprises a carcinoma, and optionally whether the tissue sample comprises cancer stem cells, based at least in part on the morphology of the cells or the expression of one or more markers by the cells as determined by the microscopic examination. In some embodiments, the results of the analysis in step (b) are further indicative of whether the subject has an aggressive or non-aggressive cancer. In some embodiments, the methods further comprise diagnosing the subject as having an aggressive or non-aggressive cancer based on the results of (a) and (b).

Aspects of the invention provide methods for evaluating aggressiveness of a cancer of non-mesenchymal origin in a subject. In some embodiments, the methods involve (a) subjecting a sample of the cancer obtained from the subject to a gene expression analysis, wherein the gene expression analysis comprises determining expression levels of one or more metabolic mesenchymal genes in the sample using an expression level determining system, and wherein the results of the analysis are indicative of whether cancer is aggressive or non-aggressive; and (b) establishing that the subject has an aggressive or non-aggressive cancer of non-mesenchymal origin based on the results of (a).

In some embodiments, an aggressive cancer is (i) a cancer associated with a poor prognosis; (ii) a highly malignant cancer; (iii) a cancer containing cancer stem cells; (iv) a cancer enriched for cancer stem cells; (v) a cancer that is resistant to one or more chemotherapeutic agents; and/or (vi) a cancer that has metastasized or is prone to metastasize.

Further aspects of the invention provide methods for treating a subject having a cancer of non-mesenchymal origin. In some embodiments, the methods involve determining that the subject has an aggressive cancer by evaluating the cancer according to a method disclosed herein; and subjecting the subject to intensive and/or prolonged monitoring for recurrence or metastasis, or subjecting the subject to intensive and/or prolonged therapy for the cancer. In some embodiments, the methods involve (a) subjecting a sample of the cancer obtained from the subject to a gene expression analysis, wherein the gene expression analysis comprises determining expression levels of one or more metabolic mesenchymal genes in the sample using an expression level determining system; and (b) comparing the expression levels determined in (a) to reference expression levels of the one or more metabolic mesenchymal genes in appropriate reference cells, wherein the results of the comparison are indicative of whether the cancer contains or is enriched for cancer stem cells (CSC); (c) determining that the cancer contains or is enriched for CSCs based on the comparison in (b); and (d) treating the subject with a CSC-selective agent after determining that the cancer contains CSCs in (c).

Further aspects of the invention provide methods of assessing non-mesenchymally derived cancer cells. In some embodiments, the methods involve (a) subjecting non-mesenchymally derived cancer cells to a gene expression analysis, wherein the gene expression analysis comprises determining expression levels of one or more metabolic mesenchymal genes in the non-mesenchymally derived cancer cells using an expression level determining system; and (b) comparing the expression levels determined in (a) to reference expression levels of the one or more metabolic mesenchymal genes in appropriate reference cells, wherein the results of the comparison are indicative of the extent to which the non-mesenchymally derived cancer cells have undergone a epithelial-to-mesenchymal transition.

Still further aspects of the invention provide method for identifying the tissue of origin of cancer cells. In some embodiments, the methods involve (a) subjecting the cancer cells to a gene expression analysis, wherein the gene expression analysis comprises determining expression levels of one or more metabolic mesenchymal genes in the cancer cells using an expression level determining system, wherein the expression levels of the metabolic mesenchymal genes are indicative of the tissue of origin of the cancer; and (b) determining the tissue of origin of the cancer cells based on the expression levels of the one or more metabolic mesenchymal genes. In some embodiments of the methods, the cancer is a carcinoma.

In some embodiments of the methods, the metabolic mesenchymal genes are selected from Table 2. In some embodiments of the methods, the metabolic mesenchymal genes are selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. In some embodiments of the methods, the metabolic mesenchymal genes are selected from: QPRT, CYBA, PTER, MFNG, TM7SF2, PLCG2, ST6GAL1, CA2, GLB1L2, PIK3C2B, GCH1, ALDH1A1, GPX2, and GALNT3. In some embodiments of the methods, the metabolic mesenchymal genes are selected from a gene in a pathway selected from: a sulfatase pathway, heparan sulfate biosynthesis pathway, nicotine degradation pathway, prostaglandin pathway, methionine pathway, branched-chain-amino-acid aminotransferase, pathway, glycan pathway, monoxygenase pathway, peptidylamidoglycan pathway, melatonin degradation pathway, phosphatidate phosphatase pathway, hyaluronan synthase pathway, nitric oxide pathway, extracellular sulfatase pathway, dermatan sulfate biosynthesis pathway, phosphodiesterase pathway, neprilysin pathway, glutathione pathway, lipid phosphate phosphohydrolase pathway, glycogen biosynthesis pathway, cytochrome c pathway, UDP-N-acetyl-D-glucosamine biosynthesis pathway, glucosylceramide synthasis pathway, nucleotide pathway, triacylglycerol degradation pathway, amino sugar pathway, sphingosine kinase 1 pathway, carbonic acid pathway, UDP pathway, adenylate kinase pathway, aldoketoreductase pathway, NAD pathway, cytochrome pathway, cholesterol biosynthesis pathway, phospholipase pathway, Beta-galactoside pathway, lactose degradation pathway, tetrahydrobiopterin biosynthesis pathway, retinoate biosynthesis pathway, glutathione peroxidase pathway, and O-glycan pathway.

In some embodiments of the methods, each expression level is a level of a RNA encoded by a metabolic mesenchymal gene of the one or more metabolic mesenchymal genes. In certain embodiments, the expression level determining system comprises a hybridization-based assay for determining the RNA levels. In some embodiments, the hybridization-based assay is an oligonucleotide array assay, an oligonucleotide conjugated bead assay, a molecular inversion probe assay, a serial analysis of gene expression (SAGE) assay, or an RT-PCR assay.

In some embodiments of the methods, each expression level is a level of a protein encoded by a metabolic mesenchymal gene of one or more metabolic mesenchymal genes. In certain embodiments, the expression level determining system comprises an antibody-based assay for determining the protein levels. In certain embodiments, the antibody-based assay is an antibody array assay, an antibody conjugated-bead assay, an enzyme-linked immuno-sorbent (ELISA) assay, an immunohistochemistry assay, or an immunoblot assay.

In some embodiments of the methods, the appropriate reference cells are mesenchymal cells. In some embodiments of the methods, the appropriate reference cells are non-mesenchymal cells. In some embodiments, the gene expression analysis comprises determining expression levels of at least 1, at least 2, at least 3, at least 4, at least 5, at least 10 or more metabolic mesenchymal genes in the cancer using an expression level determining system.

According to some aspects of the invention, methods are provided for inducing an epithelial to mesenchymal transition in a cell of epithelial origin. In some embodiments, the methods involve forcing expression in the cell of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, thereby inducing the cell to undergo an epithelial to mesenchymal transition. However, in some embodiments, the metabolic mesenchymal gene is selected from: DPYD, DPYSL2, DPYSL3, PPAP2B, MICAL2, PPAPDC1A, GPX8, MGST1, PLCB4, COX7A1, EXT1, DSEL, B3GNT9, CA12, HS3STSA1, MSRB3, SULF1, and UAP1. In some embodiments, the methods involve inhibiting expression in the cell of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3, thereby inducing the cell to undergo an epithelial to mesenchymal transition. In some embodiments, the methods involve forcing expression in the cell of ELOVL5 or HNMT, thereby inducing the cell to undergo an epithelial to mesenchymal transition. According to some aspects of the invention, isolated cells are provided that result from the foregoing methods. In some embodiments, kits are provided that comprise a container housing the cells. In certain embodiments, the container further comprises a cryopreservation agent.

In other aspects of the invention, methods are provided for inhibiting or reversing an epithelial to mesenchymal transition in a cell of epithelial origin. In some embodiments, the methods involve inhibiting expression in the cell of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, and thereby inhibiting or reversing an epithelial to mesenchymal transition in the cell. However, in some embodiments, the metabolic mesenchymal gene is selected from: DPYD, DPYSL2, DPYSL3, PPAP2B, MICAL2, PPAPDC1A, GPX8, MGST1, PLCB4, COX7A1, EXT1, DSEL, B3GNT9, CA12, HS3STSA1, MSRB3, SULF1, and UAP1. In some embodiments, the methods involve inhibiting expression in the cell of ELOVL5 or HNMT, and thereby inhibiting or reversing an epithelial to mesenchymal transition in the cell. In some embodiments, the methods involve forcing expression in the cell of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3, and thereby inhibiting or reversing an epithelial to mesenchymal transition in the cell. According to some aspects of the invention, isolated cells are provided that result from the foregoing methods. In some embodiments, kits are provided that comprise a container housing the cells. In certain embodiments, the container further comprises a cryopreservation agent.

In some embodiments of the methods the step of inhibiting expression comprises accumulating in the cell an exogenous inhibitory RNA that inhibits the metabolic mesenchymal gene. In some embodiments of the methods, the cell of epithelial origin is a cancer cell, optionally which is a carcinoma cell. In some embodiments of the methods, the cell of epithelial origin is a non-cancer cell. In some embodiments of the methods, the cell of epithelial origin is in vivo. In some embodiments of the methods, the cell of epithelial origin is in vitro.

According to some aspects of the invention, kits are provided that comprise one or more containers housing reagents for forcing expression in a cell of epithelial origin a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, wherein at least one reagent comprises a nucleic acid encoding the metabolic mesenchymal gene. In some embodiments, the kits further comprise instructions for forcing expression of the metabolic mesenchymal gene to induce the cell to undergo an epithelial to mesenchymal transition.

According to some aspects of the invention, kits are provided that comprise one or more containers housing reagents for inhibiting expression or activity in the cell of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3, wherein at least one reagent comprises an inhibitory agent that inhibits expression or activity of the metabolic mesenchymal gene. In some embodiments, the kits further comprise instructions for inhibiting expression or activity in the cell of a metabolic mesenchymal gene to induce the cell to undergo an epithelial to mesenchymal transition.

According to some aspects of the invention, kits are provided that comprise one or more containers housing reagents for forcing expression in a cell of epithelial origin a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3, wherein at least one reagent comprises a nucleic acid encoding the metabolic mesenchymal gene. In some embodiments, the kits further comprise instructions for forcing expression of the metabolic mesenchymal gene to inhibit or reverse an epithelial to mesenchymal transition in the cell.

According to some aspects of the invention, kits are provided that comprise one or more containers housing reagents for inhibiting expression in the cell of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, wherein at least one reagent comprises an inhibitory agent that inhibits expression or activity of the metabolic mesenchymal gene. In some embodiments, the kits further comprise instructions for inhibiting expression or activity in the cell of a metabolic mesenchymal gene to inhibit or reverse an epithelial to mesenchymal transition in the cell.

In some embodiments of the foregoing kits, the inhibitory agent is an inhibitory oligonucleotide or a nucleic acid encoding an inhibitory RNA.

According to some aspects of the invention, methods are provided for treating a cancer in a subject. In some embodiments, the methods involve administering an agent to the subject that forces expression of a metabolic mesenchymal gene, in cells of the cancer, wherein the metabolic mesenchymal gene is selected from: QPRT, CYBA, PTER, MFNG, TM7SF2, PLCG2, ST6GAL1, CA2, GLB1L2, PIK3C2B, GCH1, ALDH1A1, GPX2, and GALNT3. Thus, in certain embodiments, the agent comprises a nucleic acid engineered to express the metabolic mesenchymal gene. In some embodiments, the methods involve administering an agent to the subject that inhibits expression of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. However, in certain embodiments, the metabolic mesenchymal gene is selected from: DPYD, DPYSL2, DPYSL3, PPAP2B, MICAL2, PPAPDC1A, GPX8, MGST1, PLCB4, COX7A1, EXT1, DSEL, B3GNT9, CA12, HS3STSA1, MSRB3, SULF1, and UAP1. In some embodiments, the methods involve administering an agent to the subject that inhibits expression of ELOVL5 or HNMT. Thus, in certain embodiments, the agent comprises a nucleic acid engineered to express an inhibitory RNA that selectively inhibits expression of the gene.

According to some aspects of the invention, methods are provided for treating a subject having or at risk of having cancer. In some embodiments, the methods involve administering to the subject an agent that: (a) selectively inhibits activity of the product of a metabolic mesenchymal gene (i) that is upregulated in cancer cells compared with non-cancer cells and/or (ii) that induces an EMT in cancer cells; or (b) inhibits expression of a metabolic mesenchymal gene (i) that is upregulated in cancer cells compared with non-cancer cells and/or (ii) that induces an EMT in cancer cells; or (c) selectively induces expression of a metabolic mesenchymal gene (i) that is downregulated in cancer cells compared with non-cancer cells and/or (ii) that inhibits or reverses an EMT in cancer cells. In some embodiments, the agent is administered to the subject within one year of at least one other treatment for the cancer in the subject. In some embodiments, the at least one other treatment is (i) a surgery to remove malignant or premalignant cells from the subject; or (ii) radiation therapy directed at eradicating malignant or premalignant cells from the subject; or (iii) a conventional chemotherapy treatment. In some embodiments, the agent is administered after the at least one other treatment. In some embodiments, the agent is administered before the at least one other treatment. In some embodiments, the methods further comprise determining that subject has the cancer. In some embodiments, the methods further comprise determining that the cancer contains cells that exhibit mesenchymal properties. In some embodiments, the methods further comprise determining that the cancer contains cells that exhibit a metabolic gene mesenchymal signature. In some embodiments, the metabolic mesenchymal gene is selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. In some embodiments, the metabolic mesenchymal gene is selected from: DPYD, DPYSL2, DPYSL3, PPAP2B, MICAL2, PPAPDC1A, GPX8, MGST1, PLCB4, COX7A1, EXT1, DSEL, B3GNT9, CA12, HS3STSA1, MSRB3, SULF1, and UAP1. In some embodiments, the metabolic mesenchymal gene is selected from: QPRT, CYBA, PTER, MFNG, TM7SF2, PLCG2, ST6GAL1, CA2, GLB1L2, PIK3C2B, GCH1, ALDH1A1, GPX2, and GALNT3.

In some embodiments, the metabolic mesenchymal gene is HAS2 and the agent is 4-methylumbelliferone or an analog thereof. In some embodiments, the metabolic mesenchymal gene is CA12 and the agent is coumarin or an analog thereof. In some embodiments, the metabolic mesenchymal gene is BCAT1 and the agent is gabapentin, pregabalin, atagabalin or analog of any one of these agents. In some embodiments, the metabolic mesenchymal gene is DPYD, DPYSL2, DPYSL3, DPYSL2 and/or DPYSL3 and the agent is gimeracil or an analog thereof. In some embodiments, the method further comprises administering to 5-FU to the subject. In some embodiments, the gimeracil or an analog thereof in the absence of treatment with 5-FU (e.g., in the absence of a treatment with 5-FU within 1 year, 6 months or less of the treatment with gimeracil or an analog thereof). In some embodiments, the metabolic mesenchymal gene is MGLL and the agent is JZL184 or an analog thereof. In some embodiments, the metabolic mesenchymal gene is UGCG and the agent is miglustat or an analog thereof. In some embodiments, the metabolic mesenchymal gene is MME and the agent is phosphoramidon or an analog thereof. In some embodiments, the metabolic mesenchymal gene is AOX1 and the agent is raloxifene or an analog thereof. In some embodiments, the metabolic mesenchymal gene is ENPP1 and the agent is ribavirin or an analog thereof. In some embodiments, the metabolic mesenchymal gene is ENPP2 and the agent is 53826 or an analog thereof. In some embodiments, the metabolic mesenchymal gene is SPHK1 and the agent is SK1-I (BML-258) or an analog thereof. In some embodiments, the metabolic mesenchymal gene is AKR1B1 and the agent is sorbinil, epalrestat, ranirestat, fidarestat, zopolrestat or an analog of any one of these agents. In some embodiments, the metabolic mesenchymal gene is CYP1B1 and the agent is TMS or an analog thereof. In some embodiments, the cancer is a mesenchymally-derived cancer. In some embodiments, the cancer is a non-mesenchymally-derived cancer. In some embodiments, the cancer is a carcinoma. In some embodiments, the metabolic mesenchymal gene mesenchymal signature is based on the expression of a plurality of genes listed in Table 2. In some embodiments, the cancer is a CSC-enriched or CSC-dependent cancer.

According to some aspects of the invention, kits (e.g., pharmaceutical kits) are provided. In some embodiments, the kits comprise a nucleic acid engineered to express a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3. The nucleic acid may be provided in a container, spotted on a membrane, or in another suitable form. In some embodiments, the kits further comprise instructions for administering the nucleic acid to a subject to inhibit or reverse an epithelial to mesenchymal transition in a cancer cell of epithelial origin in the subject and thereby treat cancer in the subject. In some embodiments, the kits comprise an inhibitory agent that inhibits expression or activity of the metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. The inhibitory agent may be provided in a container or in another suitable form. In some embodiments, the kits further comprise instructions for administering the inhibitory agent to a subject to inhibit or reverse an epithelial to mesenchymal transition in a cancer cell of epithelial origin in the subject and thereby treat cancer in the subject. In some embodiments, the inhibitory agent is an inhibitory oligonucleotide or a nucleic acid encoding an inhibitory RNA. In some embodiments, the instructions indicate that the cancer exhibits a metabolic gene mesenchymal signature.

According to some aspects of the invention, methods for identifying a cancer stem cell targeting agent are provided. In some embodiments, the methods involve (a) obtaining test cells that have been determined to exhibit a metabolic gene mesenchymal signature; (b) exposing the test cells to a test agent; (c) determining the extent to which the test agent inhibits growth or invasiveness of the test cells; and (d) identifying the test agent as a cancer stem cell targeting agent if the test agent inhibits growth or invasiveness of the test cells. In some embodiments, the test cells are cells derived from a carcinoma. In some embodiments, the test cells are engineered to express an inhibitory RNA that selectively inhibits expression of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3. In some embodiments, the test cells are engineered to express a metabolic mesenchymal gene selected from the group consisting of: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1.

According to some aspects of the invention, methods for identifying metabolic mesenchymal genes that inhibit an epithelial to mesenchymal transition (EMT) are provided. In some embodiments, the method comprise: (a) obtaining a test cell of epithelial origin; (b) forcing expression of a metabolic mesenchymal gene in the test cell; (c) subjecting the test cell to a condition suitable for inducing an EMT in an epithelial cell, while the metabolic mesenchymal gene is expressed in the test cell; and (d) determining the expression of one or more biomarkers in the test cell that are indicative of an EMT in the test cell, wherein if the one or more biomarkers indicates that the EMT has not occurred in the test cell, then the metabolic mesenchymal gene is identified as a metabolic mesenchymal gene that inhibits EMT. In some embodiments, the methods comprise: (a) obtaining test cells of epithelial origin; (b) forcing expression of metabolic mesenchymal genes in the test cells such that each test cell expresses one metabolic mesenchymal gene; (c) subjecting the test cells to a condition suitable for inducing an EMT in an epithelial cell, while the metabolic mesenchymal genes are expressed in the test cells; (d) evaluating one or more biomarkers in the test cells that are indicative the presence or absence of an EMT in the test cells; (e) collecting a test cell in which the one or more biomarkers indicates absence of an EMT; and (d) identifying the metabolic mesenchymal gene expressed in the collected test cell, wherein the identified metabolic mesenchymal gene is a gene that inhibits EMT. In some embodiments, the condition suitable for inducing an EMT is selected from: (i) inducing the activity of a transcription factor in the test cell(s), wherein the transcription factor is selected from: Snail1, Snail2, Goosecoid, FoxC2, TWIST, E2A, SIP-1/Zeb-2, dEF1/ZEb1, LEF1, Myc, HMGA2, TAZ, Klf8, HIF-1, HOXB7, SIM2s, and Fos; or (ii) inducing the activity of TWIST in the test cell(s); or (iii) contacting the test cell(s) with a growth factor selected from: a TGF-β/BMP superfamily member, a Wnt-family member, an FGF family member, a Notch Ligand, an EGF family member, an IGF family member, PDGF, and HGF; or (iv) modulating the activity of a signaling pathway in the test cell(s), wherein the signaling pathway is selected from TGF-β, Wnt, BMP, Notch, HGF-Met, EGF, IGF, PDGF, FGF, P38-mapk, Ras, PI3Kinase-Akt, Src, and NF-kB; or (v) subjecting the test cell(s) to a stress selected from: hypoxia, irradiation, and chronic chemotherapy treatment; or (vi) subjecting the test cell(s) to treatment with nicotine, nAChR agonists, hydrogen peroxide, C3a, or MFG-E8; or (vii) inducing the expression of dysadherin in the test cell(s); or (viii) interfering with cell-polarity genes in the test cell(s).

According to some aspects of the invention, methods are provided for identifying a candidate agent for inhibiting EMT and/or for treatment of cancer. In some embodiments, the methods involve (a) contacting a cell with a test agent; and (b) determining whether the test agent: (i) inhibits expression of a metabolic mesenchymal gene, or (ii) inhibits the activity of a gene product of the metabolic mesenchymal gene, wherein if the test agent inhibits expression of the metabolic mesenchymal gene or the activity of the gene product, the test agent is identified as a candidate agent for inhibiting EMT and/or for treatment of cancer. In some embodiments, the methods involve exposing the gene product of a metabolic mesenchymal gene to a test agent under conditions suitable for assessing the activity of the gene product; and determining whether the test agent inhibits the activity of the gene product, wherein if the test agent inhibits the activity of the gene product, the test agent is identified as a candidate agent for inhibiting EMT and/or for treatment of cancer.

In some embodiments, the metabolic mesenchymal gene is selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. In some embodiments, the metabolic mesenchymal gene is selected from: DPYD, DPYSL2, DPYSL3, PPAP2B, MICAL2, PPAPDC1A, GPX8, MGST1, PLCB4, COX7A1, EXT1, DSEL, B3GNT9, CA12, HS3STSA1, MSRB3, SULF1, and UAP1. In some embodiments, the methods further comprise determining whether the test agent or an analog of the test agent: (i) inhibits or reverses an EMT in a cell of epithelial origin, optionally wherein the cell is a cancer cell; (ii) inhibits cell invasion, metastasis or proliferation; (iii) induces cell death; and/or (iv) exhibits in vivo toxicity. In some embodiments, the methods further comprise administering the test agent to a test animal having or at risk of a cancer and determining the effect of the test agent on cancer development, cancer cell EMT, invasion, metastasis, or other event associated with EMT in the test animal.

In some embodiments, kits are provided that comprise one or more containers housing at least two oligonucleotides, each of which oligonucleotides hybridizes to a different nucleic acid, wherein each nucleic acid has a nucleotide sequence of a metabolic mesenchymal gene selected from Table 2. According to some aspects of the invention a solid support is provided having immobilized thereto oligonucleotide probes consisting essentially of: (i) at least two different oligonucleotide probes each of which hybridizes to a different nucleic acid, wherein each different nucleic acid has a nucleotide sequence of a metabolic mesenchymal gene selected from Table 2; and, optionally, (ii) at least one control oligonucleotide probe that hybridizes to a control nucleic acid, optionally wherein the control nucleic acid has a nucleotide sequence of a housekeeping gene.

In some embodiments, kits are provided that comprise one or more containers housing at least two different antigen binding agents, each of which different antigen binding agents binds specifically to a protein product of a metabolic mesenchymal gene selected from Table 2. According to some aspects of the invention a solid support is provided having immobilized thereto antigen binding agents consisting essentially of: (i) at least two different antigen binding agents each of which binds specifically to a protein product of a metabolic mesenchymal gene selected from Table 2; and, optionally, (ii) at least one control antigen binding agent that binds specifically to a control protein, optionally wherein the control protein is the product of a house keeping gene. In some embodiments, the antigen binding agents are antibodies or antigen-binding fragments thereof.

According to some aspects of the invention, methods are provided for identifying a candidate agent for dihydropyrimidine dehydrogenase (DPD) dependent inhibition of an EMT. In some embodiments, the methods involve (a) assessing activity of the DPD while exposed to a test agent; (b) determining whether exposure to test agent inhibits activity of the DPD; and (c) determining whether the test agent inhibits an EMT in cells of epithelial origin in a manner that depends, at least in part, on expression of DPD in the cells. In some embodiments, the activity of DPD assessed in (a) comprises the catalytic reduction of uracil to 5,6-dihydrouracil and/or the catalytic reduction of thymine to 5,6-dihydrothymine.

According to some aspects of the invention, methods are provided for identifying a candidate agent for inhibiting an EMT. In some embodiments, the methods comprise (a) obtaining a test agent that inhibits DPD activity; and (b) determining whether the test agent inhibits an EMT in cells of epithelial origin. In some embodiments, the methods further comprise determining whether the expression or intracellular localization of a dihydropyrimidinase-related protein in the cells of epithelial origin is altered in response to being exposed to the test agent. In some embodiments, the dihydropyrimidinase-related protein is dihydropyrimidinase-related protein 2 (CRMP2) or dihydropyrimidinase-related protein 3 (CRMP4). In some embodiments, the methods further comprise determining whether the cytoskeletal organization of the cells of epithelial origin is altered in response to being exposed to the test agent. In some embodiments, the methods further comprise determining whether the test agent affects invasiveness, migration ability, and/or one or more metastatic characteristics of the cells of epithelial origin.

(B) Array distribution by types. The data generated reflect the expression in five types of tissues (number of arrays) assembled in the database (i.e., cancer cell lines, primary tumors, normal tissues, non-cancer cell lines, and metastases).

(C) Normal tissues arrays cluster based on tissue of origin. Unsupervised hierarchical clustering of normal tissues based only on expression of metabolic genes. The dendrogram reflects arrays clustering together from similar tissues. Asterisks represent tissues that did not cluster. Lung is split into two groups.

(D) Normal tissues express a unique set of metabolic genes. Heatmap representing the expression of metabolic genes throughout the different normal tissues. The gene expression for each gene was examined relative to normal tissues median of median for that gene. The boxed regions indicate increased expression. Each section of the bar across the top of the figure represents a different tissue. Normal tissues median of median for a gene was determined by first determining the median of that gene's expression in each normal tissue type from the arrays for that tissue type. Then the median of these medians was obtained. Median of median was used to account for the fact that different tissues were represented in different numbers of arrays. It avoids giving more weight to those tissues for which more arrays were available.

(E) Most metabolic genes in normal tissue demonstrate a tissue specific expression pattern.

(F) Cancer cell lines and primary tumors array demonstrate higher correlation then normal tissues. All arrays by type were isolated and the Pearson correlation calculated. The distribution of the arrays correlation is demonstrated as histogram. Histograms for normal tissues, cancer cell lines and primary tumors are noted by arrows.

(G) Heat map demonstrating the expression of all the arrays relative to normal tissues median of median. The arrays were subjected to unsupervised hierarchical clustering. The normal tissues represent a tissues enriched pattern, as demonstrated by the three leftmost boxes. The primary tumors and cancer cell lines demonstrated a strip of metabolic genes that is down regulated and over expressed (Indicated with the horizontal rectangular boxes and arrows on the right side of the panel). The intensity bar represents the distribution by type. Interestingly, normal proliferating cells cluster with the cell lines. Metabolic genes that were either downregulated or overexpressed in all or almost or cancers were designated as the "universal metabolic gene set".

Figure 2:
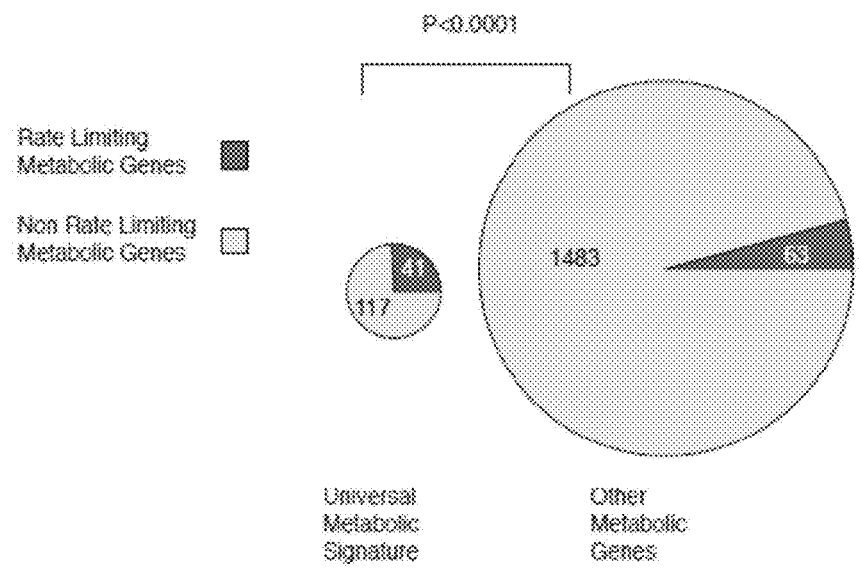
Figure 2:
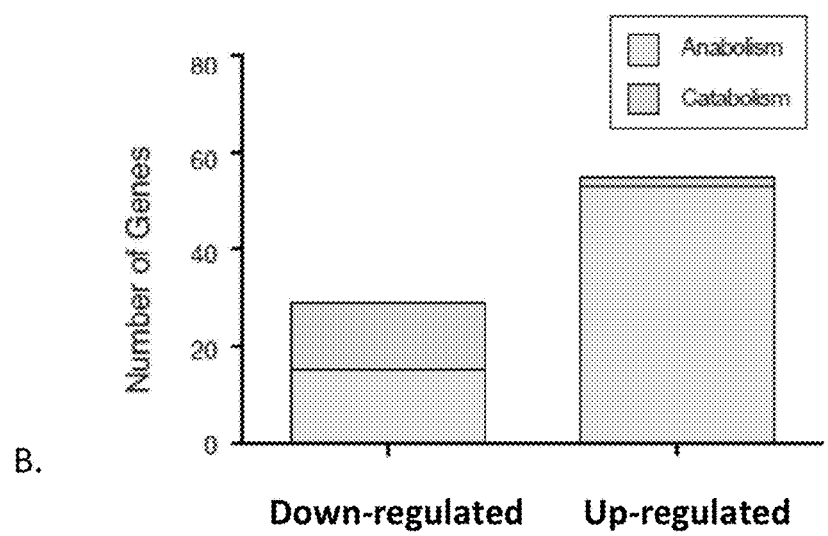

FIG. 2: Characterization of the universal metabolic gene set (A) Universal metabolic gene set is enriched with rate limiting genes. The universal metabolic gene set is composed of 158 genes; among them 41 encode rate-limiting enzymes. The other genes are composed of 1546 genes and among them 6 encode rate-limiting enzymes. Each pie chart size represents the relative number of genes. The enrichment of genes exhibiting a proliferation-driven signature was quantified using a Fisher's exact test.

(B) The up-regulated genes are mainly composed of genes encoding anabolic enzymes. A stacked bar representing the relative number of genes encoding products involved in anabolism or catabolism, in the up-regulated and down-regulated genes.

Figure 3:
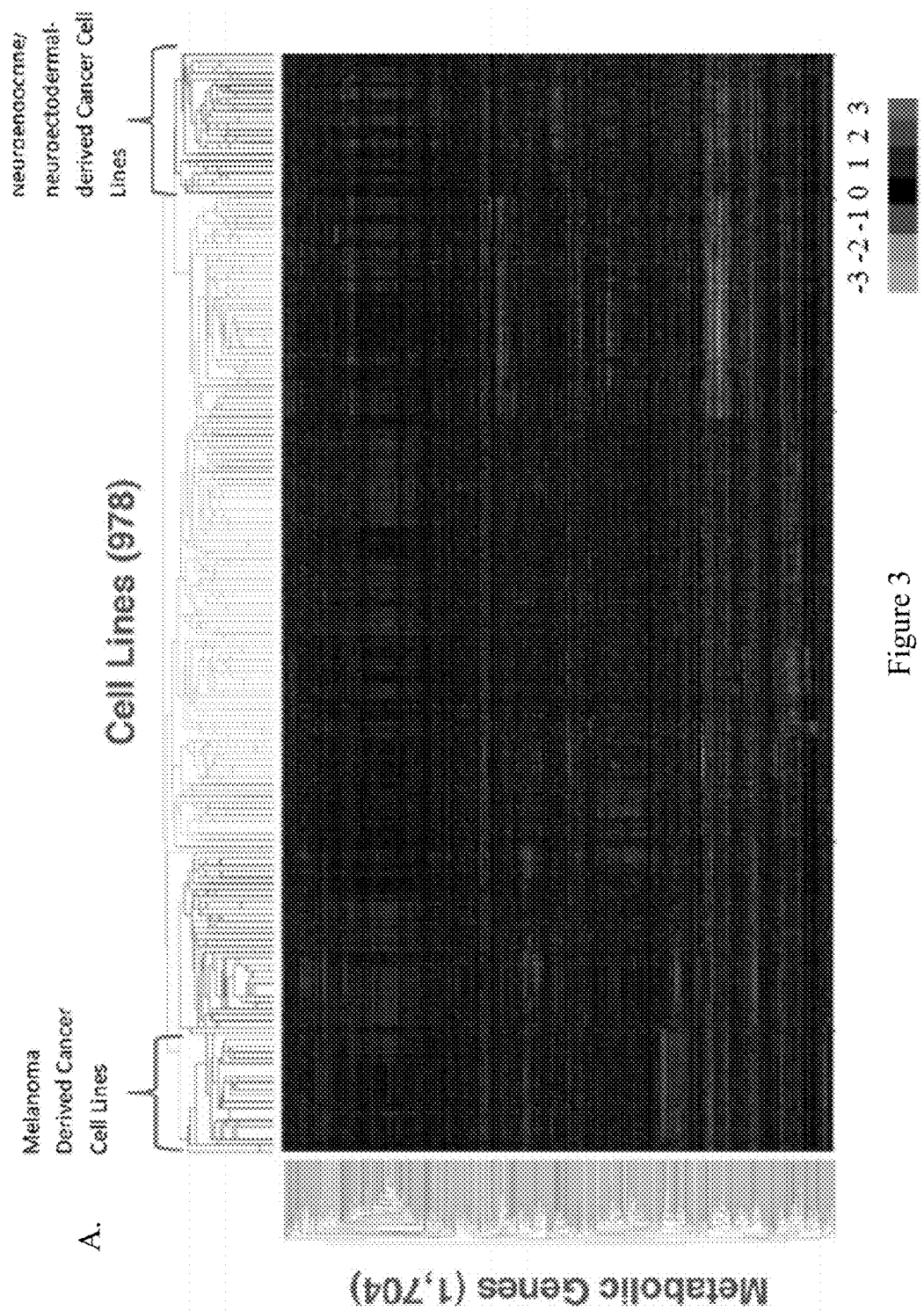
Figure 3:
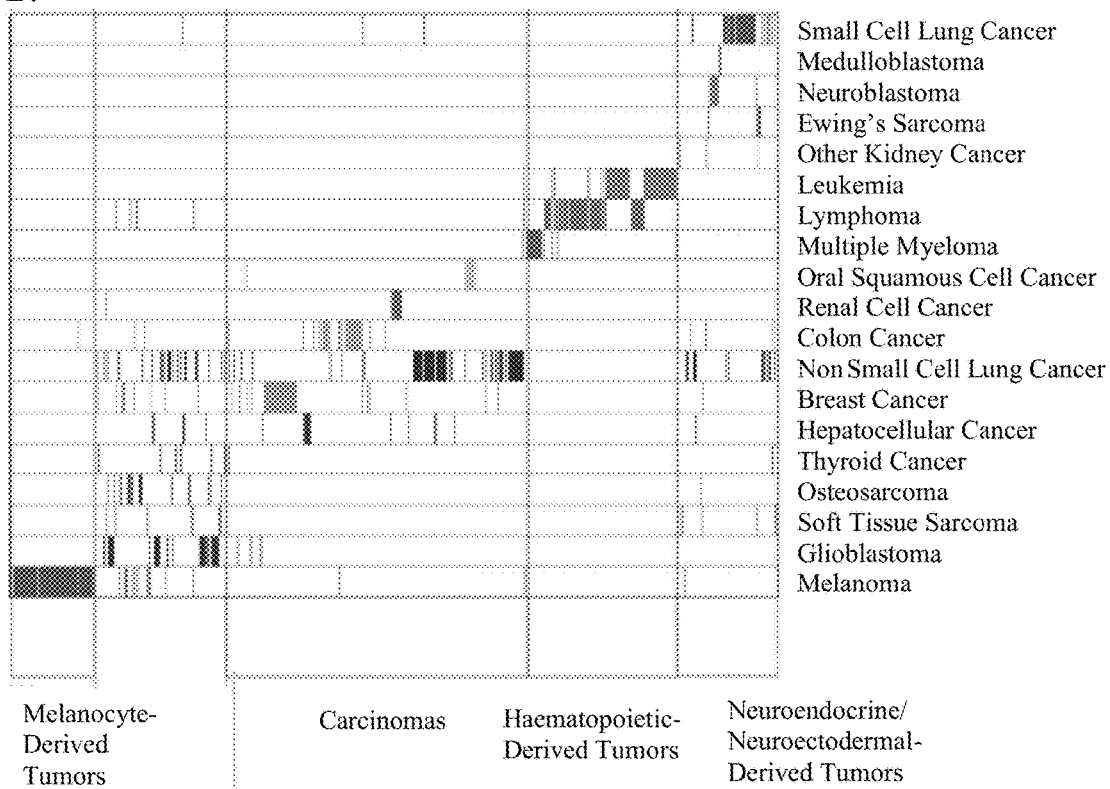
Figure 3:
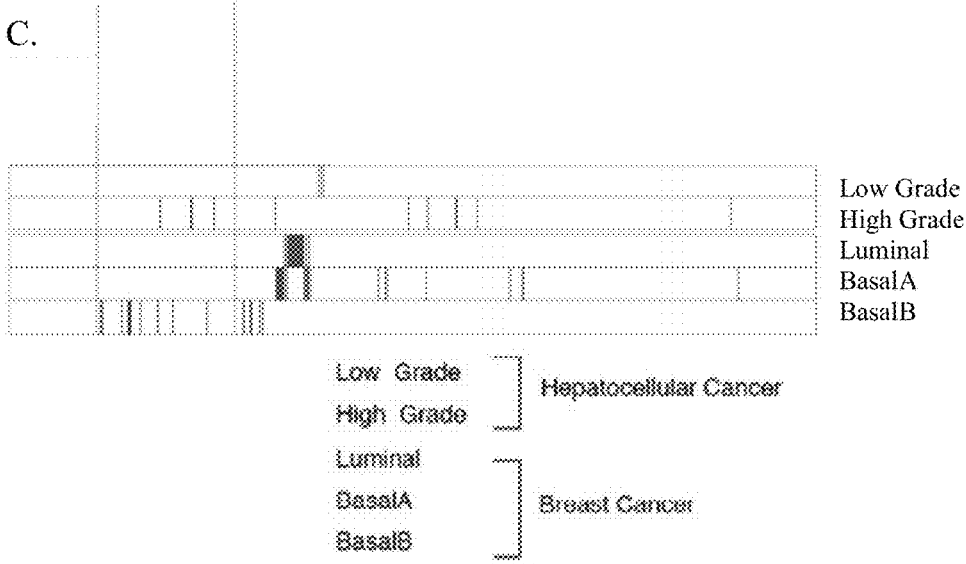
Figure 3:
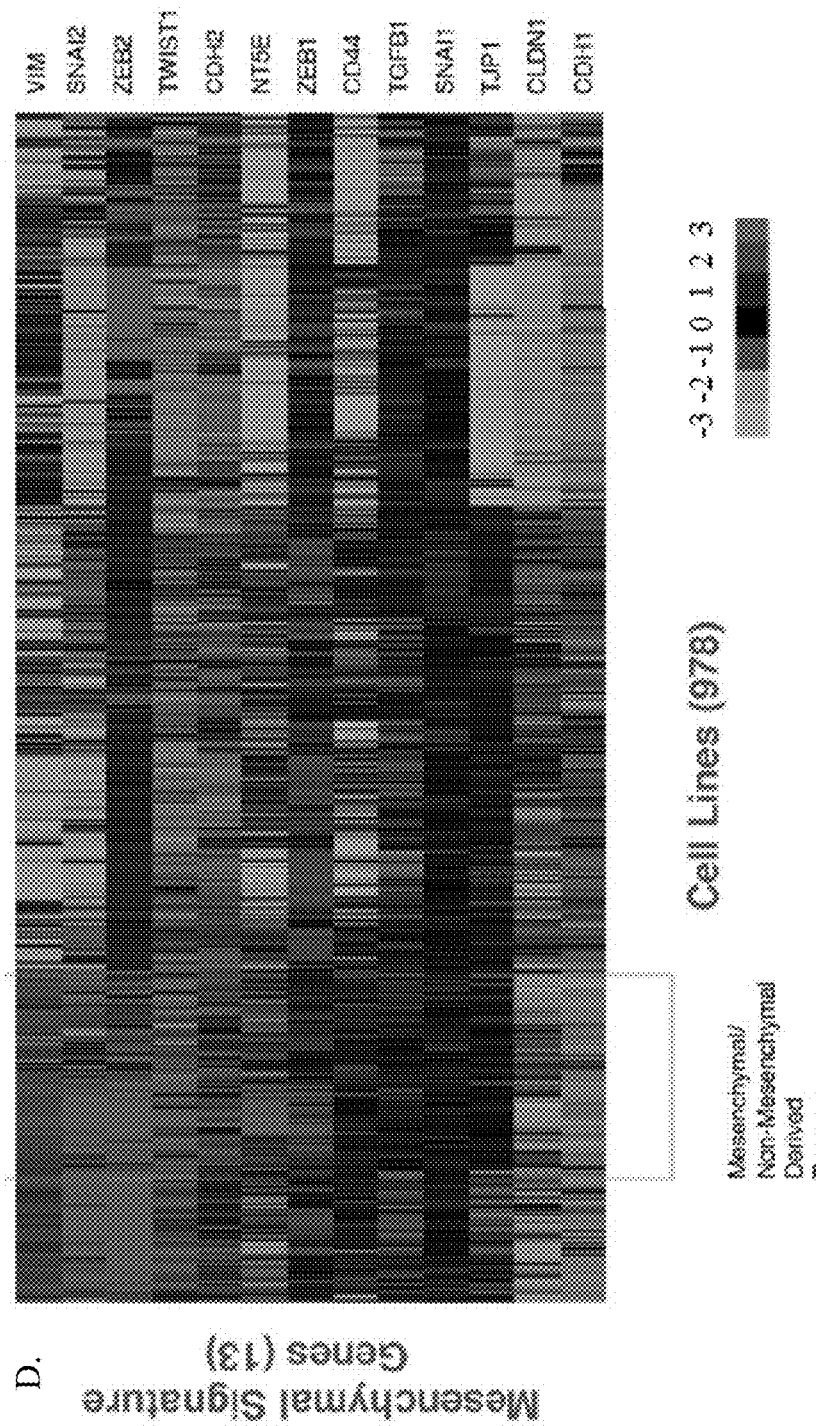

FIG. 3: Metabolic gene mesenchymal signature is found in a number of carcinoma cell lines originating from different tissues.

(A) Cancer cell lines demonstrate a cancer specific metabolic gene signature. Two ways hierarchical clustering of 1,704 metabolic genes, and 977 cell lines, each represented with one array. The values represent the log 2 expression level of each gene in a particular cell line over the cancer cell lines median of median for that gene (cancer cell lines median of median was determined using the method described above for normal tissues median of median). The dendrogram indicates the cluster based on common derived tumors (indicated in the lower portion of part (B) of this figure). For example, a portion of the dendrogram represents melanocyte-derived cancer cell lines, and another portion of the dendrogram represents neuroendocrine/neuroectodermal-derived cancer cell lines.

(B) Cancer cell lines cluster based on common derived tissue (tissue of origin). Each bar represents the indicated cancer location in the cluster (i.e., each tumor is represented as an individual narrow intensity bar. When many tumors cluster closely together, the individual vertical bars merge into a broader intensity zone.). The cancer cell line types were ordered based on their origin from similar tissues. "Mesenchmyal/Non-Mesenchymal Derived Tumors" represents cancer cell lines derived from mesenchymal tissues (e.g., osteosarcoma, soft tissue sarcoma) and certain non mesenchymally-derived cancer cell lines that clustered with the mesenchymally-derived cancer cell lines. These non-mesenchymally-derived cancer cell lines derive from a variety of non-mesenchymal tissues. (Other kidney cancers (see figure) are embryonal (HEK293), leiomyomatosis and renal cell cancer, rhabdoid tumor, and Wilms tumor.)

(C) High-grade hepatocellular and breast cancer basal B cell lines cluster within the mesenchymal derived cell lines cluster. The distribution of the high-grade hepatocellular and breast cancer subtype cell lines are demonstrated as a bar.

(D) Several of the carcinoma cell lines share a common mesenchymal signature. Cancer cell lines were ordered identically to (A). A heatmap representing known mesenchymal markers expression through all cancer cell lines is demonstrated. The values represent the log 2 over the cancer cell lines median of median.

Figure 4:
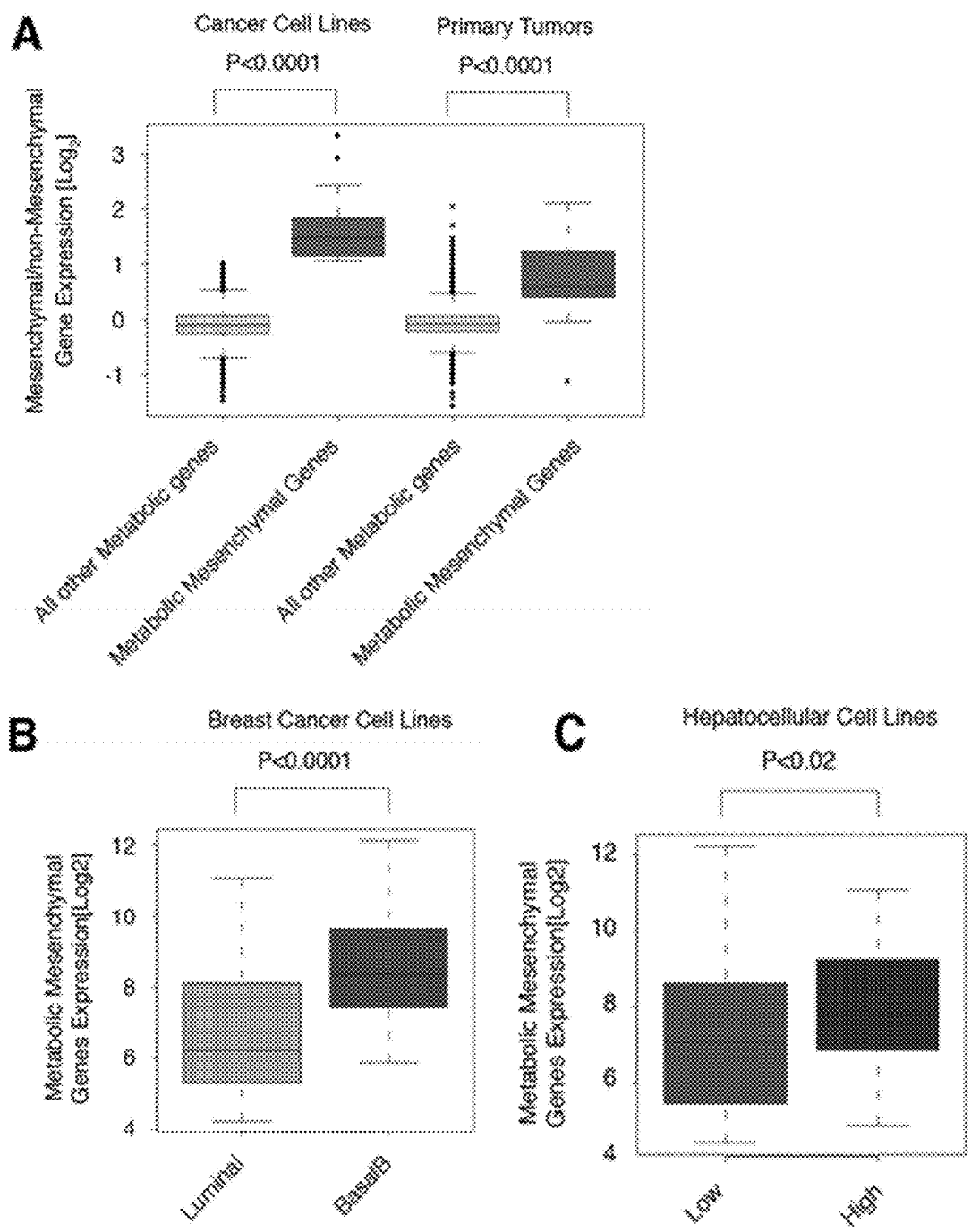
Figure 4:
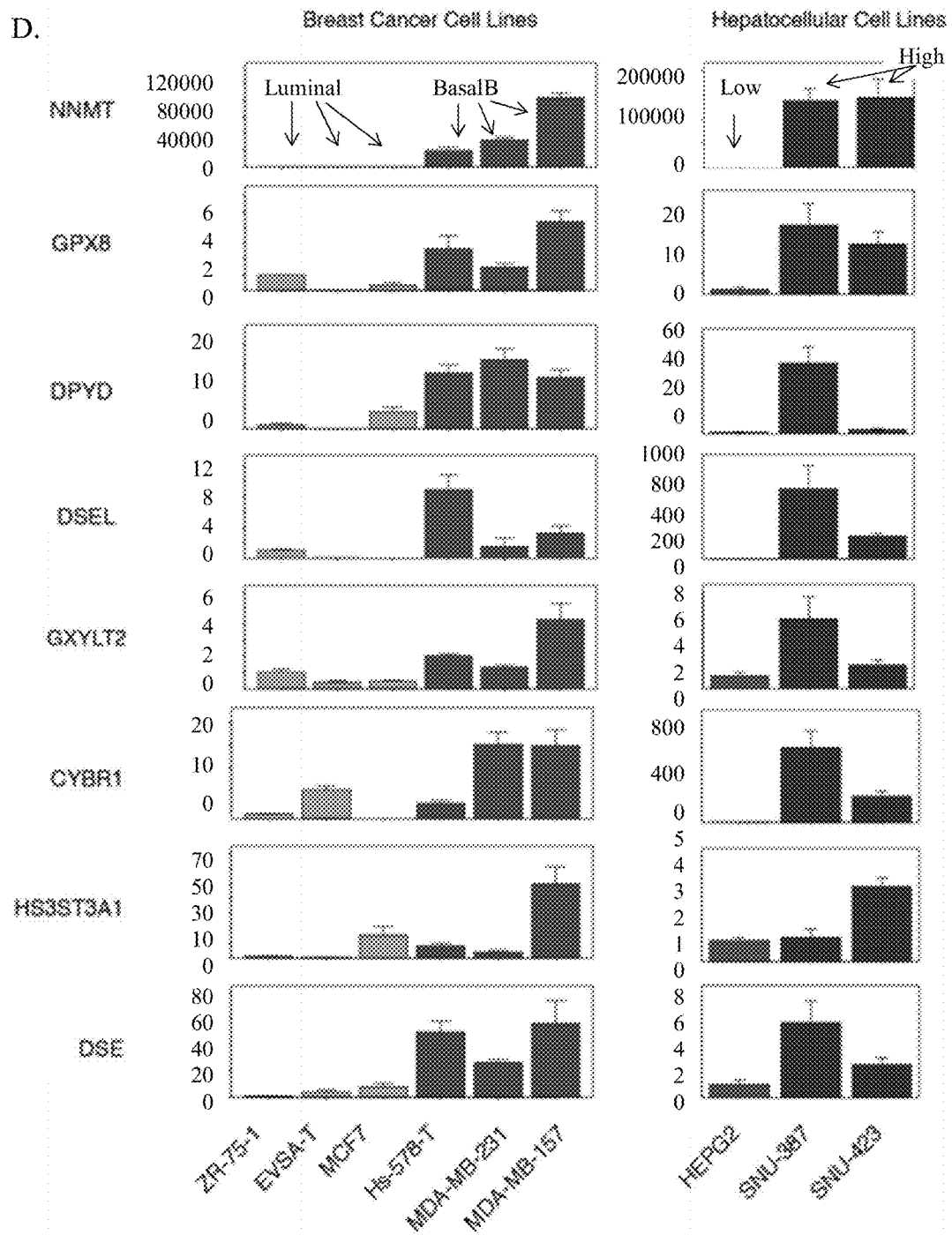
Figure 4:
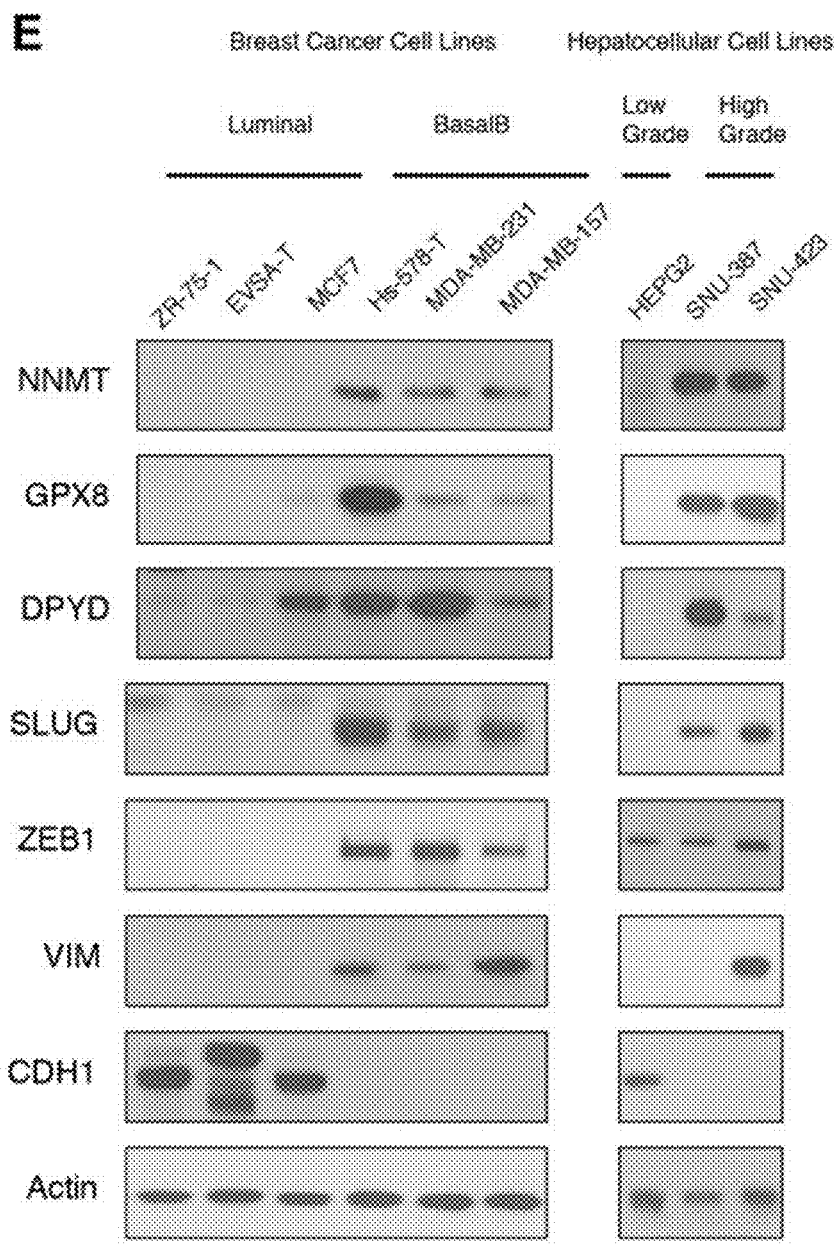

FIG. 4: Metabolic gene mesenchymal signature expression in high-grade breast and hepatocellular cell lines (A) Metabolic-gene mesenchymal signature expression in cancer cell lines and primary tumors. Cancer cell lines and primary tumors were divided into two groups, mesenchymal and non-mesenchymal. For each metabolic gene the mean expression in each group was determined, followed by ratio calculation. Boxplot represents the ratio mesenchymal/non-mesenchymal gene expression of the metabolic gene mesenchymal signature upregulated genes (MGMS-upregulated genes) vs. the other metabolic genes.

(B) Mesenchymal signature genes overexpression in BasalB breast cancer cell lines. Breast cell lines were divided by subtype (Luminal/basalB), and the expression level of the mesenchymal signature genes was determined.

(C) Metabolic mesenchymal signature genes overexpression in high-grade hepatocellular cell lines. Hepatocellular cell lines were divided by subtype (high/low grade for hepatocellular), and the expression level of the mesenchymal signature genes was determined.

(D) Metabolic mesenchymal signature genes validation in breast and hepatocellular cell lines. Quantitative RT-PCR analysis of several metabolic mesenchymal signature genes overexpression in Basal B breast cancer and high-grade hepatocellular cell lines. Error bars represent SEM.

(E) Metabolic mesenchymal signature genes validation in breast and hepatocellular cell lines Immunoblotting of selected metabolic mesenchymal genes and known mesenchymal genes.

Figure 5:
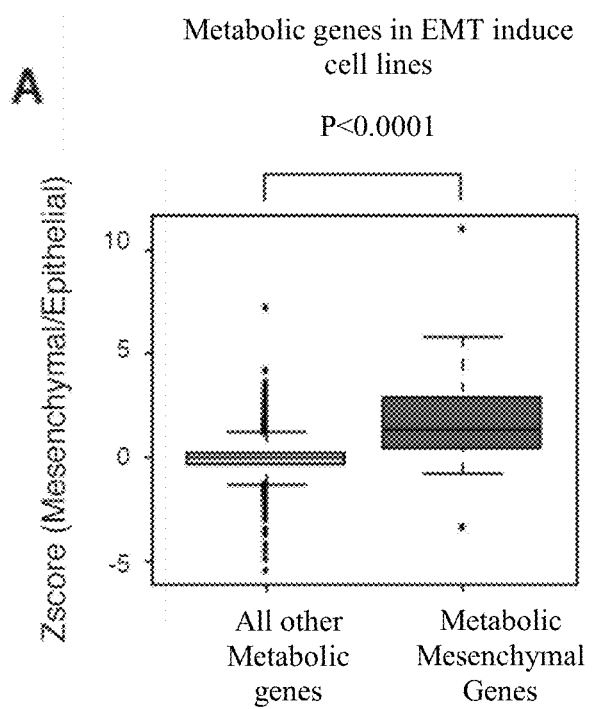
Figure 5:
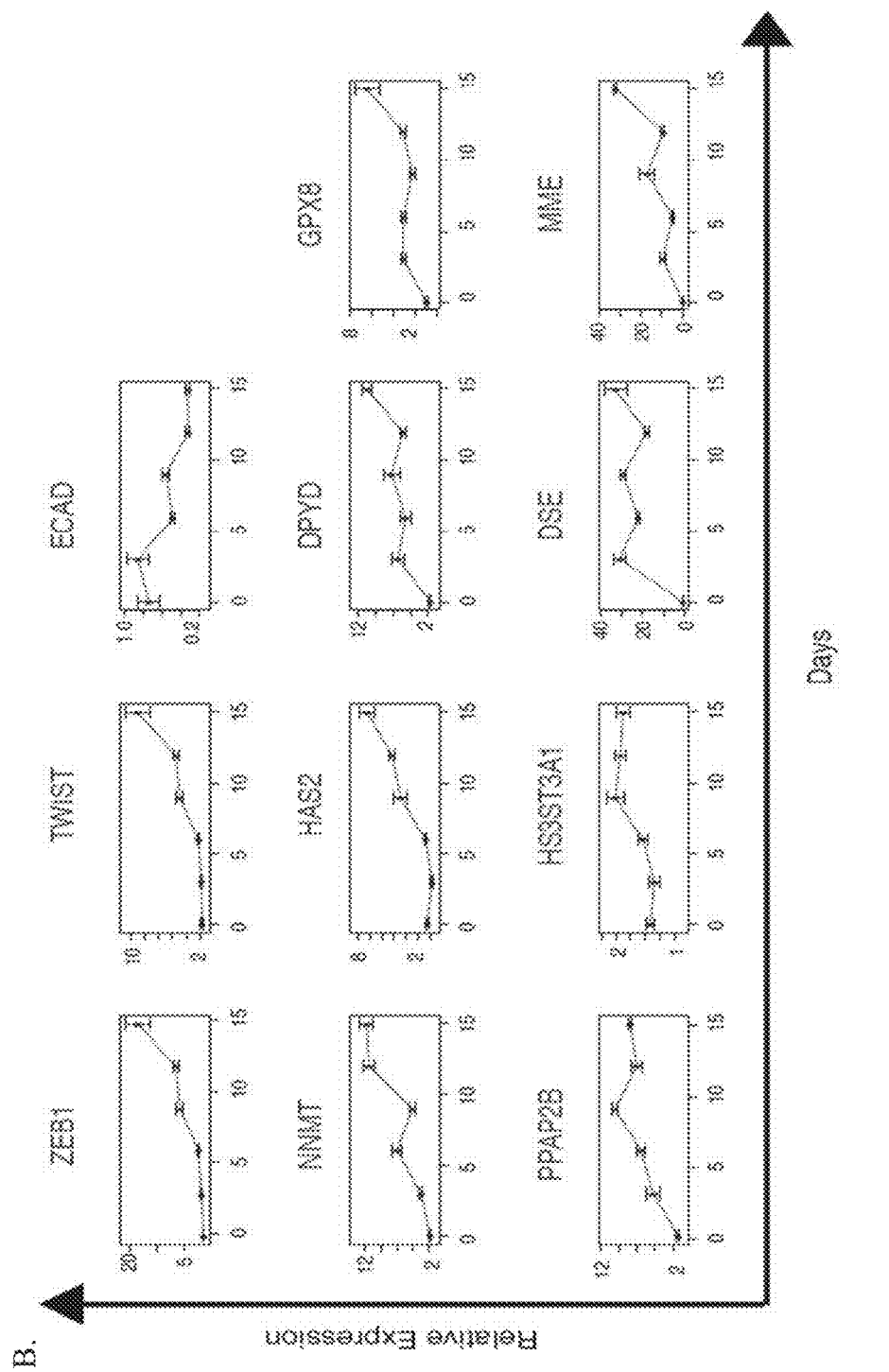
Figure 5:
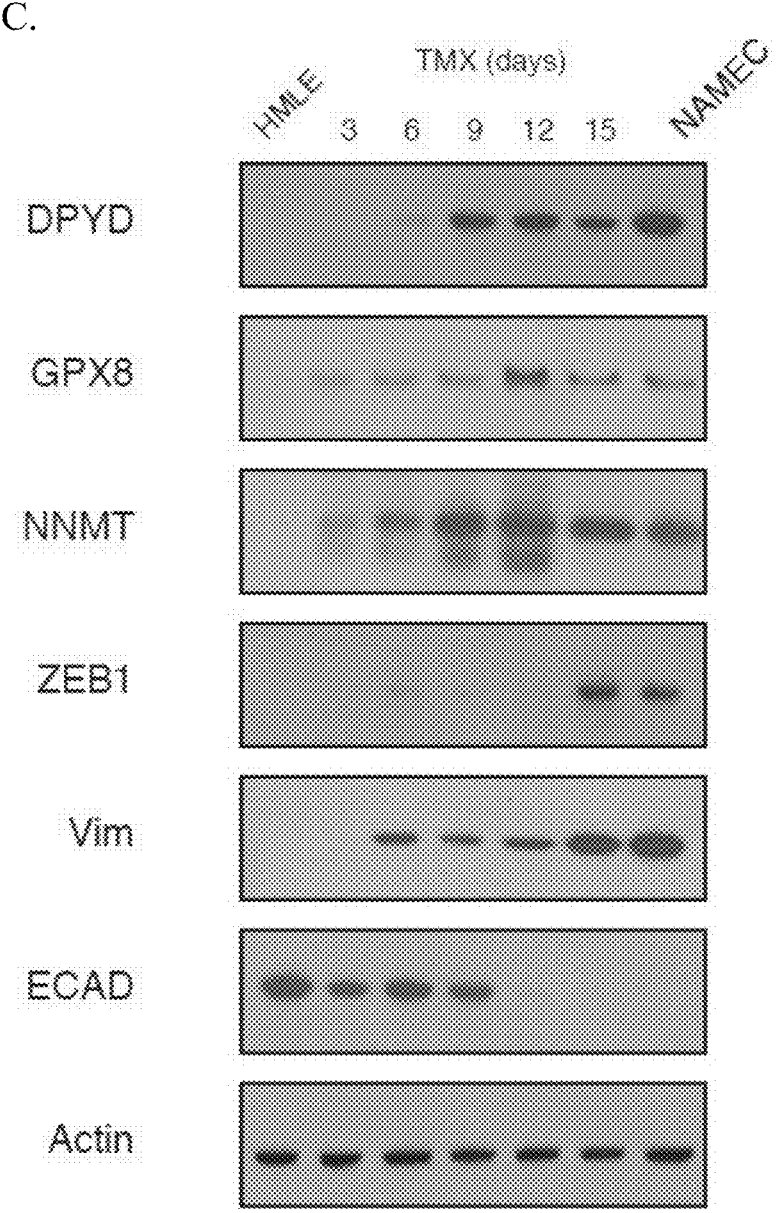
Figure 5:
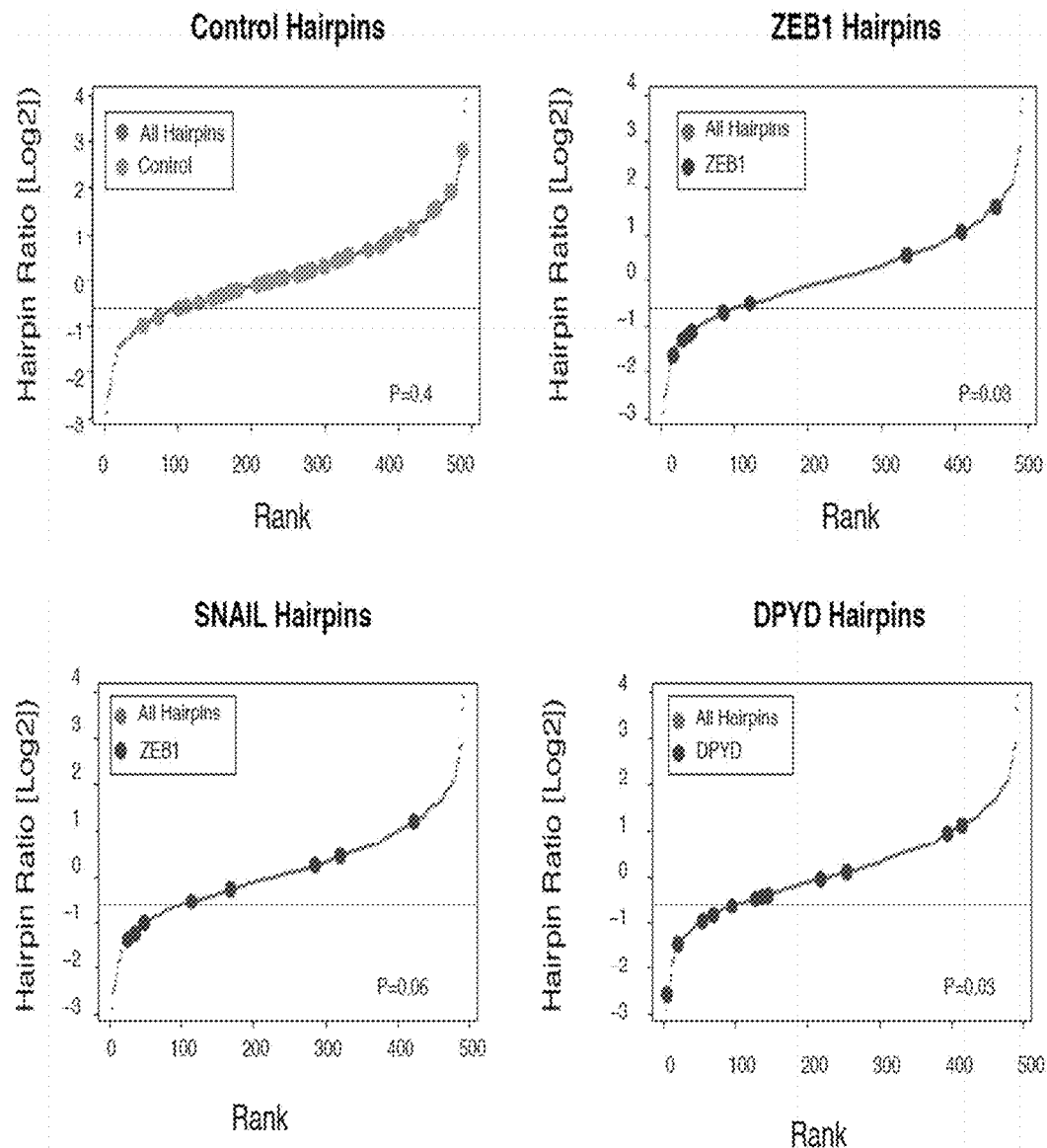
Figure 5:
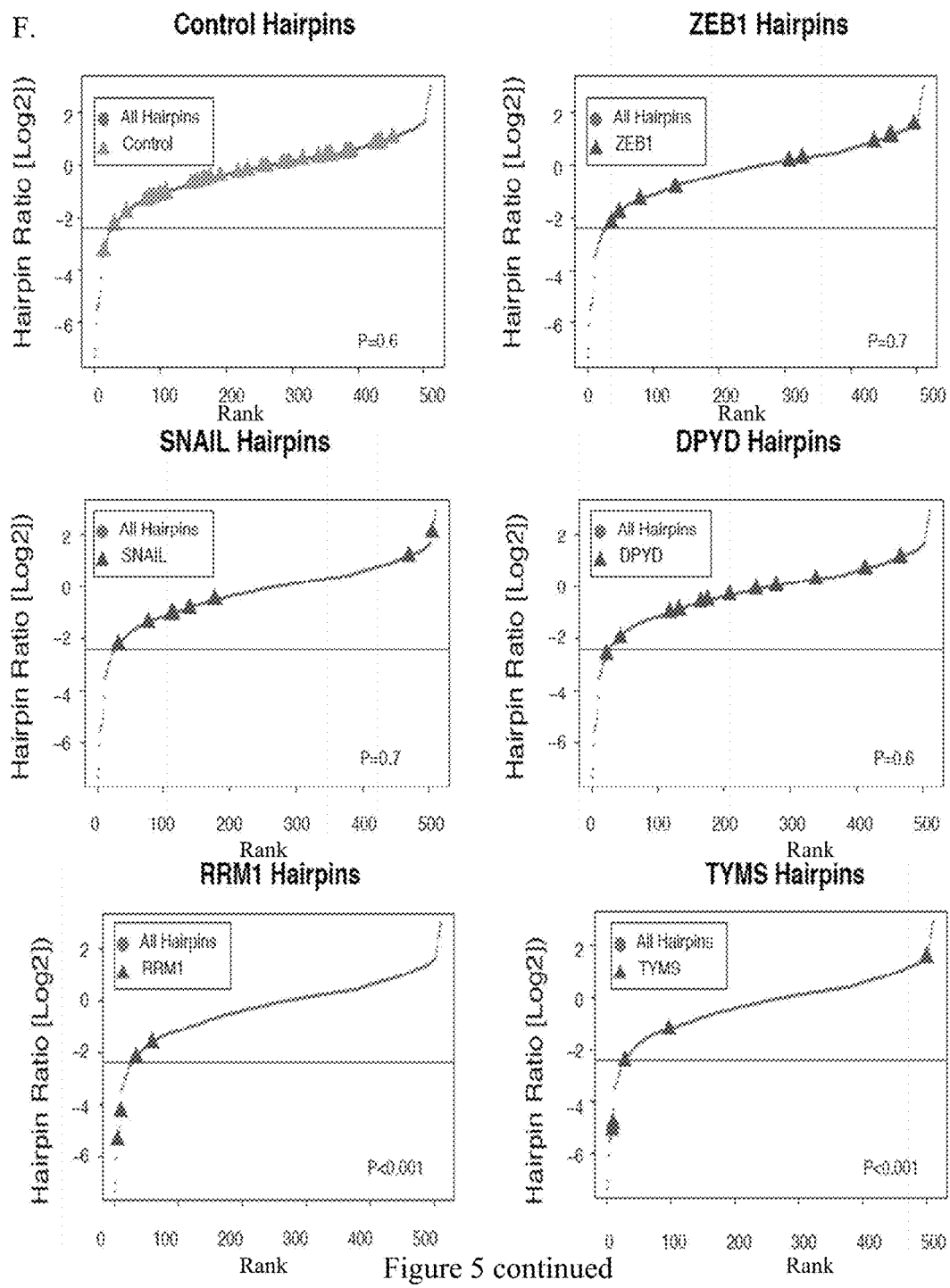

FIG. 5: Metabolic genes essentiality for EMT (A) Metabolic mesenchymal signature genes are up regulated in the inducible HMLE epithelial to mesenchymal transition. Microarray data in which HMLE cells (human, non-tumorigenic, immortalized human mammary epithelial cells) expressing tamoxifen-activatable forms of TWIST and SNAIL (Mani, S., et al., Cell. 2008 May 16; 133(4): 704-715) were induced with hydroxytamoxifen, which results in their transition from epithelial to mesenchymal phenotype were analyzed. For each gene the ratio between its expression in epithelial (uninduced) to mesenchymal (induced) cell populations was determined, and the Z-score was determined. (Note: Throughout the figures and figure legends the terms "HMLE" and "HMLE-TWIST" both refer to HMLE cells infected with a vector encoding tamoxifen-activatable TWIST. The endogenous TWIST in HMLE cells is human and the vector-encoded TWIST is mouse. Both the primers and shRNAs against TWIST used in the experiments described herein were designed against the human form and do not affect (shRNA) or detect (primers) the mouse form.)

(B) Metabolic mesenchymal signature genes up regulation in an HMLE inducible EMT system. HMLE-TWIST cells were induced with hydroxytamoxifen for 15 days. Every three days the RNA was isolated and subjected to real-time PCR using the indicated probes. The three panels in the upper row show upregulation of the known mesenchymal genes TWIST and ZEB1 and downregulation of the known epithelial gene ECAD following induction. The panels in the lower two rows show upregulation of six different metabolic mesenchymal signature genes following induction.

(C) Metabolic mesenchymal signature protein up regulation in an HMLE inducible EMT system. HMLE-TWIST cells were induced with hydroxytamoxifen for 15 days. Every three days the cellular proteins were isolated and subjected to immunoblot analysis using the corresponding antibodies. The blots show upregulation of three different metabolic mesenchymal signature proteins, upregulation of known mesenchymal proteins Zeb1 and Vim, and downregulation of the known epithelial protein E-cadherin (ECAD) following induction.

(D) A number of the metabolic mesenchymal signature genes are critical for the EMT. Functional genomics was used in order to determine the essentiality of the metabolic mesenchymal signature genes to the EMT. The pool-screen included shRNAs against each of a set of genes known to play a role in EMT (Mesenchymal genes), a set of random metabolic genes (Random Metabolic genes), all but one of the metabolic mesenchymal signature genes indicated in Table 2 as upregulated (Metabolic genes) (no shRNAs against ENPP1 were included), and one of the MGMS-downregulated genes (QPRT). The number of genes that affected EMT from the total number of genes in that particular group is indicated.

(E) DPYD knockdown (KD) affects the EMT. Cells were infected with pooled shRNAs against 75 genes. The cells were treated with tamoxifen for 15 days, followed by FACS sorting to separate the populations with mesenchymal and epithelial phenotype based on CD44/CD24 markers. The gDNA of the cells was isolated and subjected to sequencing. For each hairpin the ratio of its abundance in mesenchymal/epithelial populations was determined, and the ratios were ranked. High abundance of a hairpin in the epithelial population indicates that the gene it inhibits is important for EMT. Low abundance of a hairpin in mesechymal cells indicates that the gene it inhibits is important for EMT. (A negative ratio means that the hairpin was relatively more abundant in the epithelial population than in the mesenchymal population, indicating that the gene inhibited by the hairpin is important for EMT.) Hairpin rank distribution of control sample (39 hairpins include shRFP, shGFP, shLU- CIFERASE, shlacZ), ZEB1 (9 hairpins), SNAIL1 (SNAIL, 8 hairpins), and DPYD (12 hairpins) after 15 days treatment with tamoxifen. The horizontal grey line represents the cutoff. The significance of the distribution changes between the selected genes and the other hairpins was quantified using Student T test.

(F) DPYD KD does not affect the cellular proliferation rate. In the screen we compared the abundance of the hairpins immediately after infection and after 15 days (this was without tamoxifen treatment). The same hairpins as in (E) were tested, with the addition of RRM1 (4 hairpins) and TYMS (4 hairpins). The significance of the distribution changes between the selected genes and the other hairpins was quantified using Student T test. This data shows that shRNAs against RRM1 and TYMS, metabolic genes that affect proliferation and are not part of the MGMS, are less abundant after 15 days, whereas shRNAs against DPYD, ZEB1, and SNAIL demonstrate a similar distribution of rank as control shRNA. shRNAs against the other MGMS-upregulated genes also did not affect proliferation (data not shown).

Figure 6:
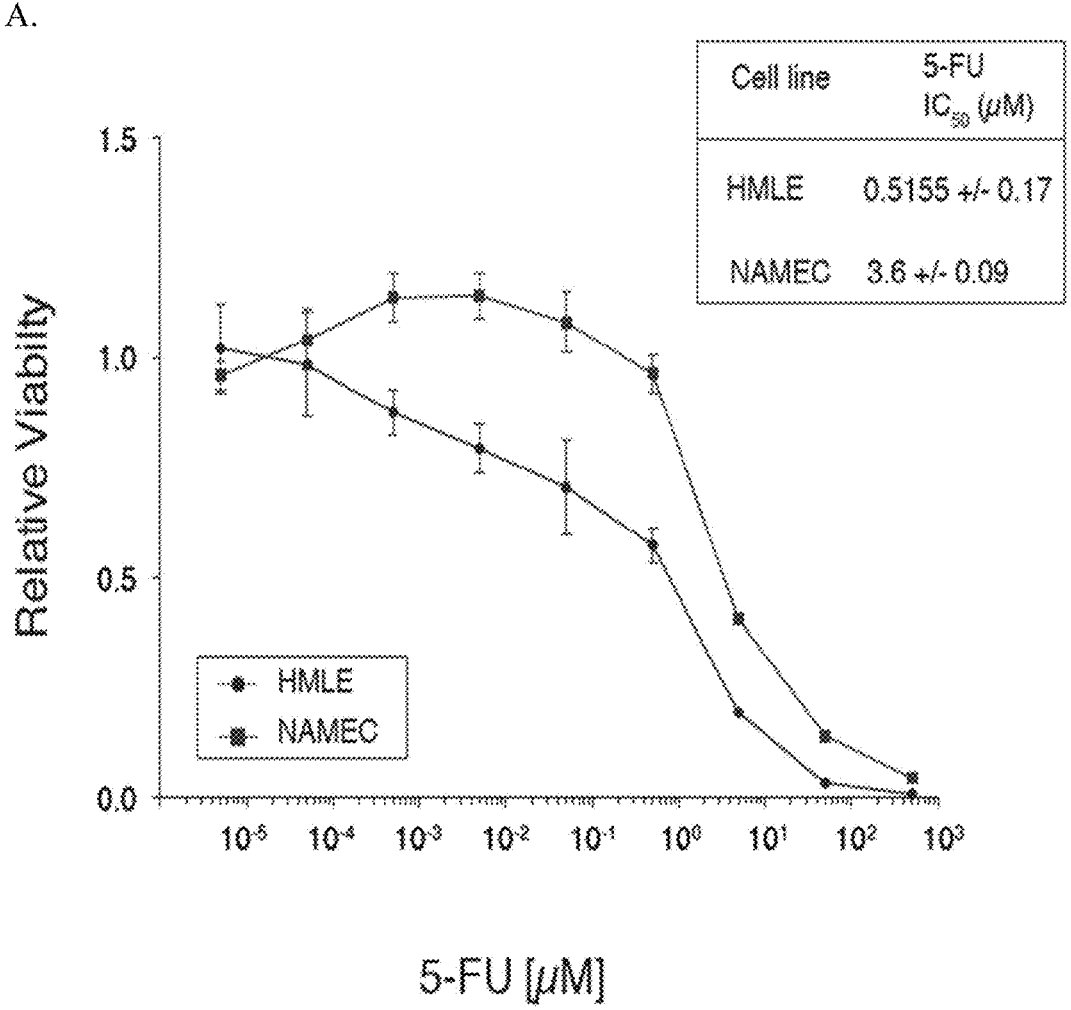
Figure 6:
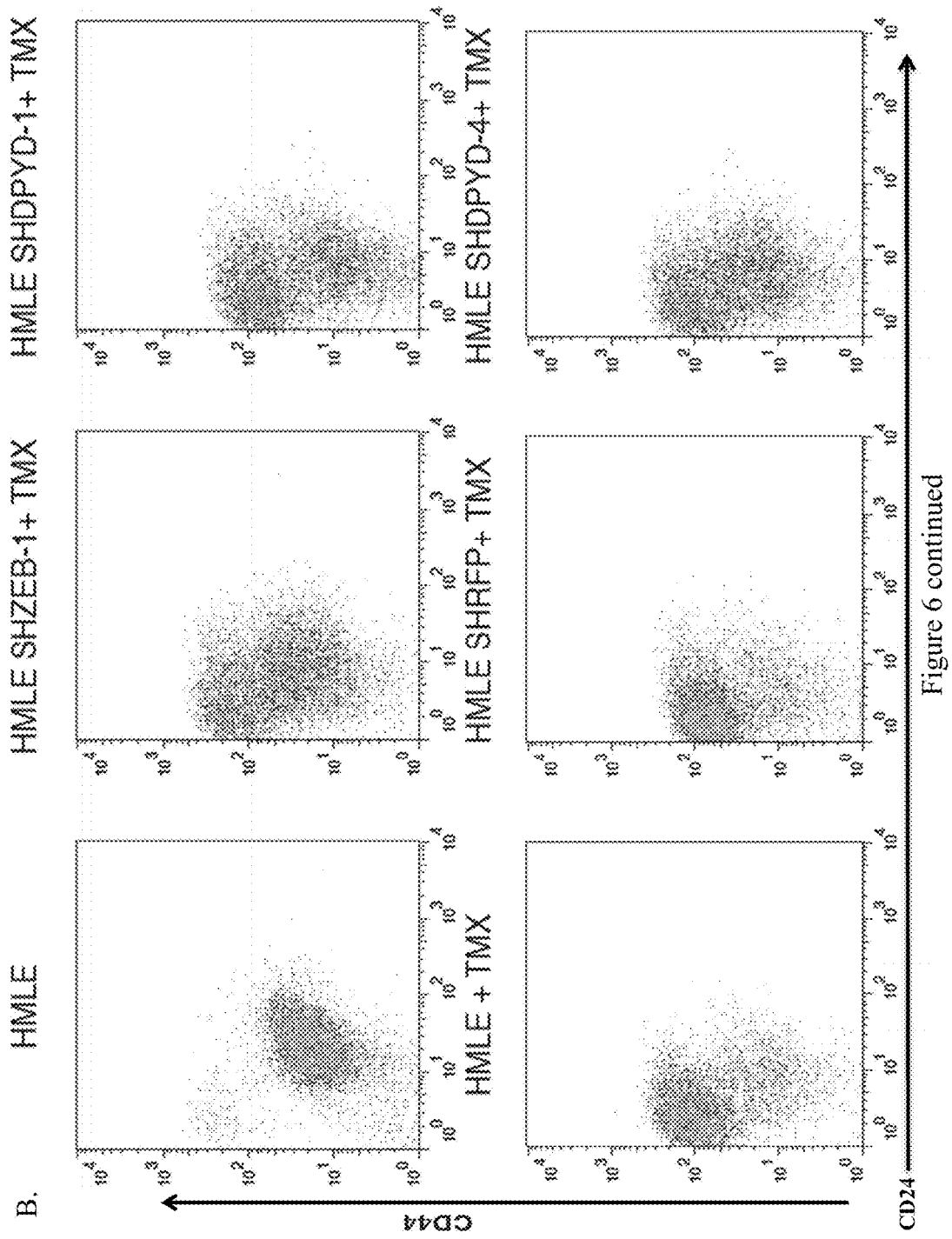
Figure 6:
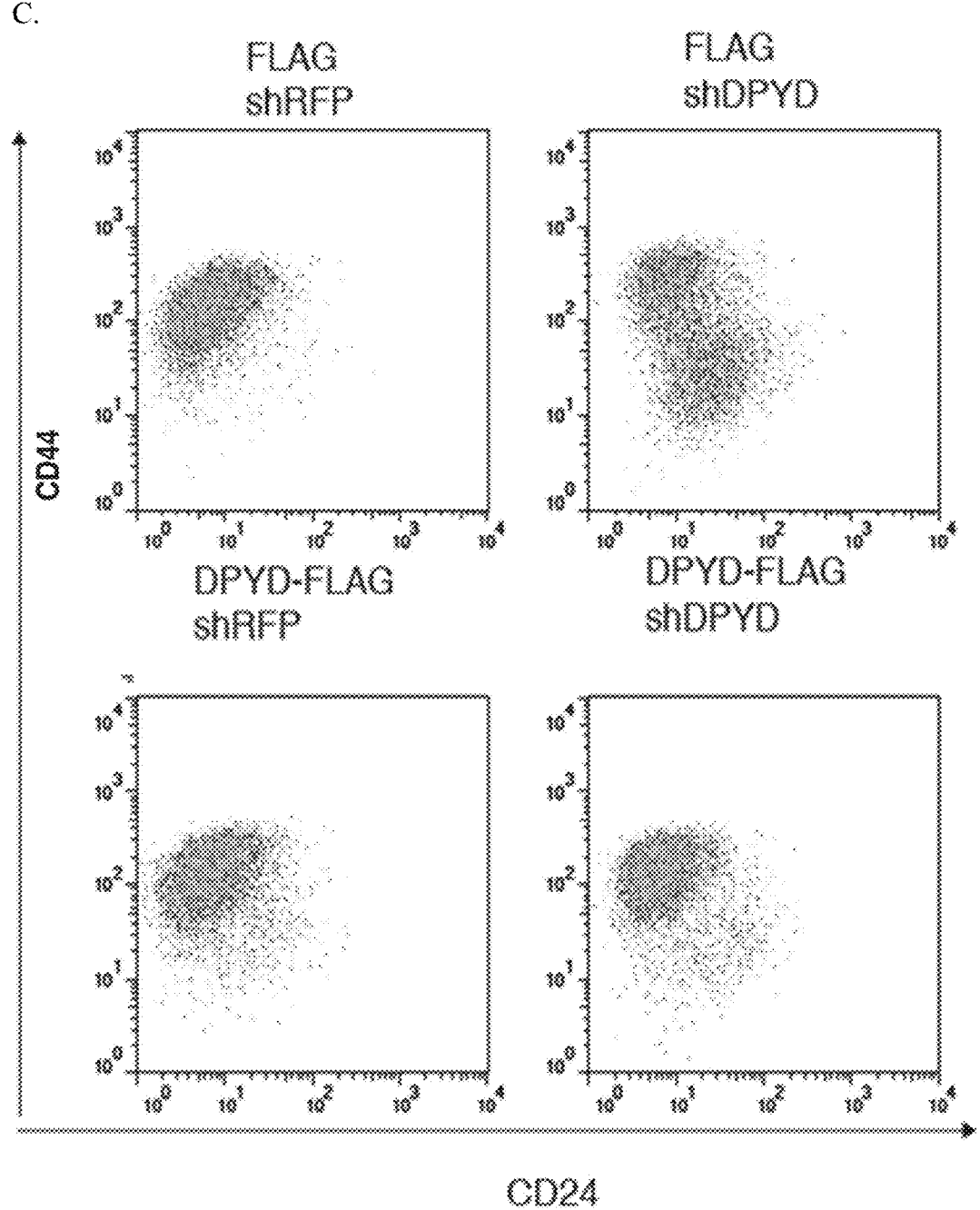
Figure 6:
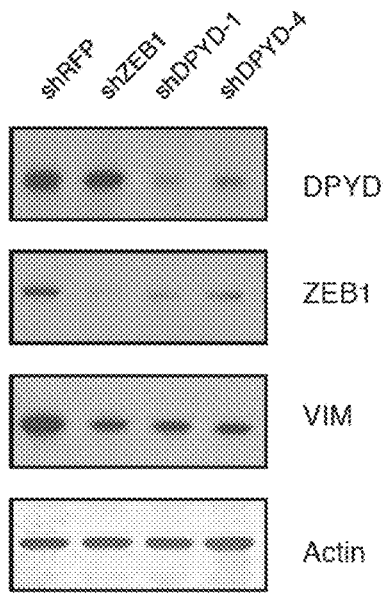
Figure 6:
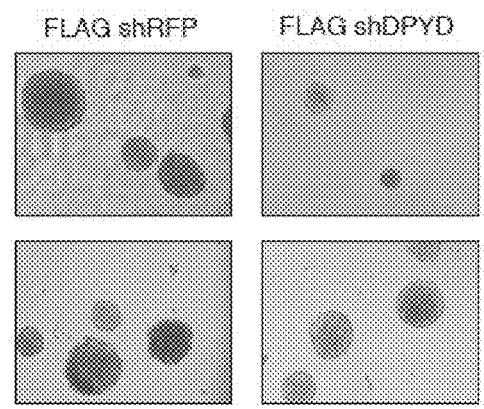
Figure 6:
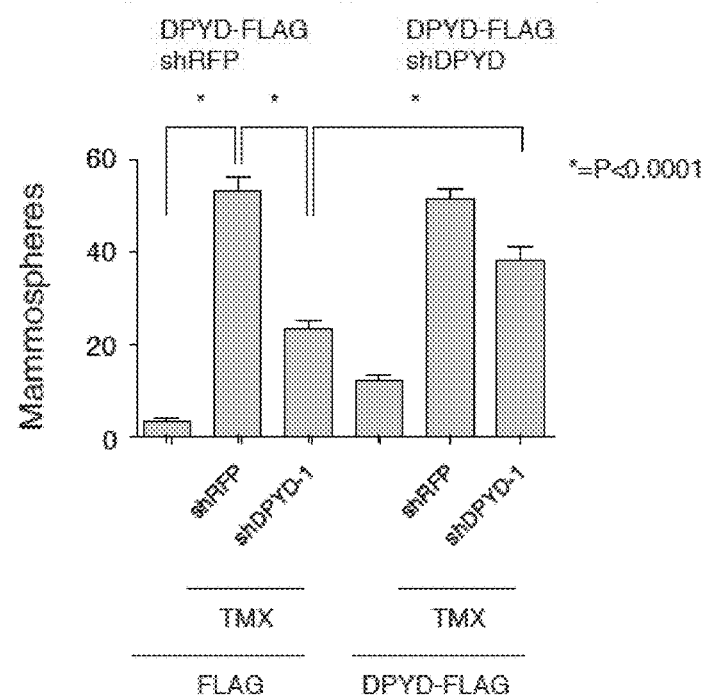
Figure 6:
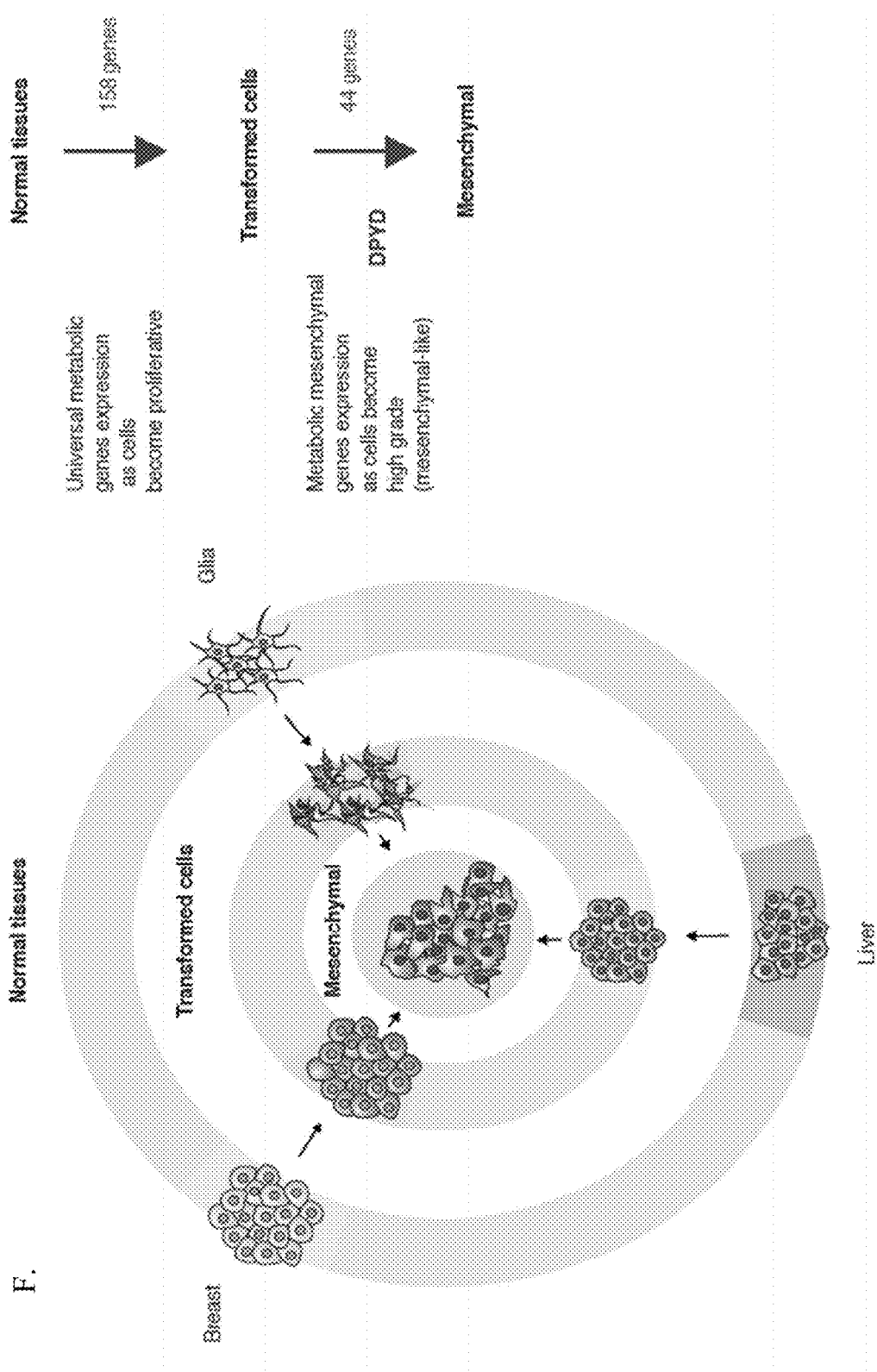

FIG. 6: DPYD influences EMT (A) DPYD is more activated in NAMEC then in HMLE cell lines. DPYD activity was measured by the ability of cells to tolerate 5-flurouracil (5-FU). Both cell lines were treated with increasing concentration of 5-FU. The IC50 was determined using PRISM software. (5-FU is a pyrimidine analog that inhibits thymidylate synthase and is used as a chemotherapeutic agent in the treatment of several cancer types (e.g., colorectal cancer, pancreatic cancer). It is toxic both to cancer cells and to normal proliferating cells. 5-FU is metabolized by DPYD. Thus cells that have high DPYD activity are more resistant to 5-FU (can tolerate higher concentrations) than cells that have lower DPYD activity.)

(B) DPYD knockdowns affect EMT. HMLE-TWIST cells were infected with viruses containing hairpins against RFP (ShRFP), ZEB1 (ShZEB1), and DPYD (ShDPYD1, ShDPYD4). HMLE-TWIST cells were induced with hydroxytamoxifen for 15 days, and subjected to FACS analysis using CD24-FITC and CD44-APC as markers. Following tamoxifen treatment HMLE-TWIST cells either containing no hairpin or containing a hairpin against RFP mainly exhibited a CD44$^{high}$/CD24$^{low}$ marker profile indicative of a mesenchymal state, whereas cells containing hairpins against ZEB1 or DPYD retained a CD44$^{low}$/CD24$^{high}$ marker profile characteristic of uninduced HMLE-TWIST cells.

(C) DPYD over expression rescues cells from the knockdown effect. HMLE cells were transfected with empty vector (FLAG) or with a vector encoding FLAG-tagged DPYD (DPYD-FLAG) followed by DPYD or RFP knockdown, and subjected to FACS analysis using CD24-FITC and CD44-APC as markers.

(D) DPYD affects ZEB1 and VIM expression. HMLE cells were infected with viruses containing hairpins against RFP (ShRFP), ZEB1 (ShZEB1), and DPYD (ShDPYD1, ShDPYD4). Cell lysates were analyzed by immunoblotting for level of indicated proteins. Reduced DPYD expression resulted in reduced ZEB1 and VIM protein levels.

(E) DPYD expression level affects mammosphere formation. HMLE cells were infected with viruses containing hairpins against RFP (ShRFP) or DPYD (ShDPYD1) together with empty vector or DPYD-FLAG and subjected to mammosphere formation assay. The samples were analyzed using bright-phase microscopy for mammosphere quantification.

(F) Model for metabolic genes function in cancer. In normal tissues metabolic genes demonstrate distinct metabolic gene expression profiles. As cells become transformed they lose most of their distinct gene expression pattern and become more similar one to the other. This is mediated by the expression changes of 158 genes that share an expression pattern in all proliferative cells. Mesenchymal cancers and certain carcinomas (mainly composed of high grade carcinomas), as well as various other cancers of non-mesenchymal origin, share a mesenchymal signature composed of 43 metabolic genes. One gene in particular that plays a role is DPYD, which functions in the cells transition from epithelial to mesenchymal phenotype.

Figure 7:
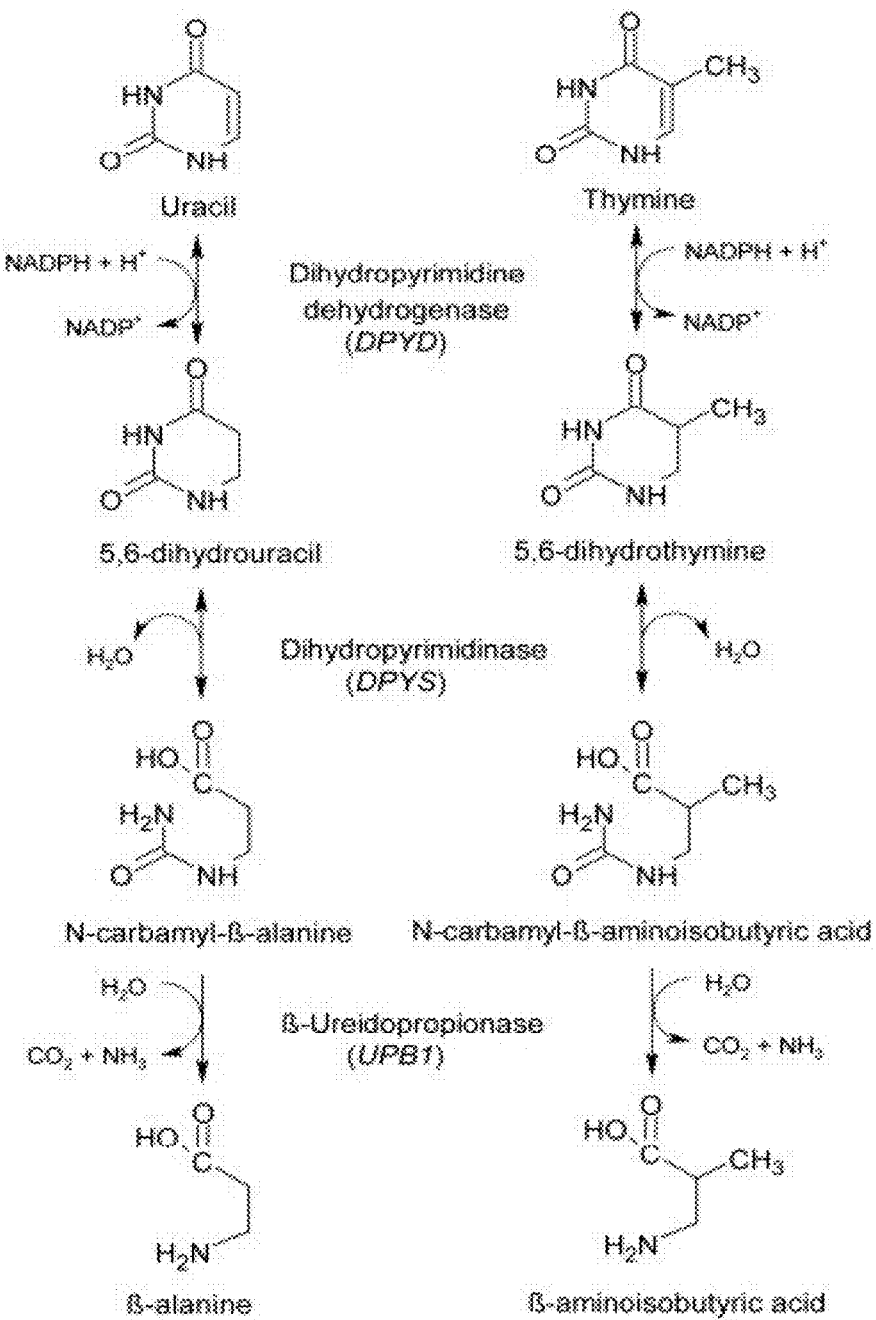

FIG. 7: Pyrimidine catabolism pathway

Dihydropyrimidine dehydrogenase (DPD, EC 1.3.1.2, encoded by the gene DYPD) is a pyrimidine catabolic enzyme and is the initial and rate-limiting enzyme in the pathway by which the pyrimidine bases uracil and thymine are degraded.

Figure 8:
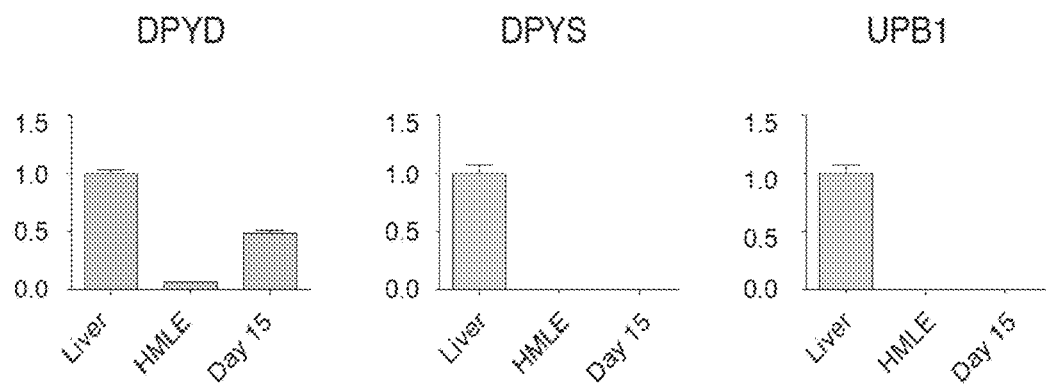
Figure 8:
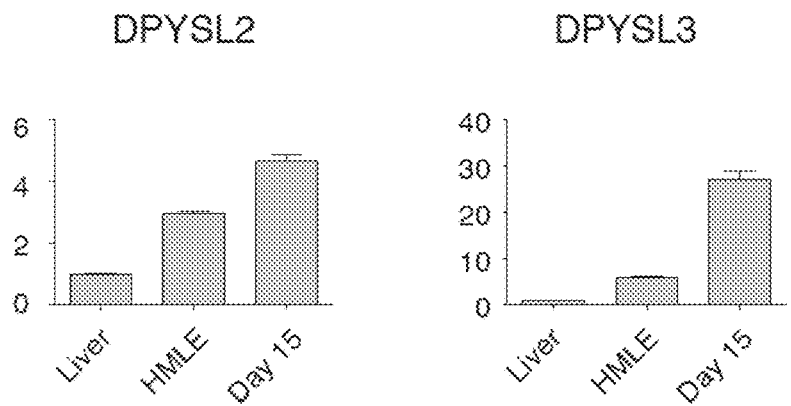
Figure 8:
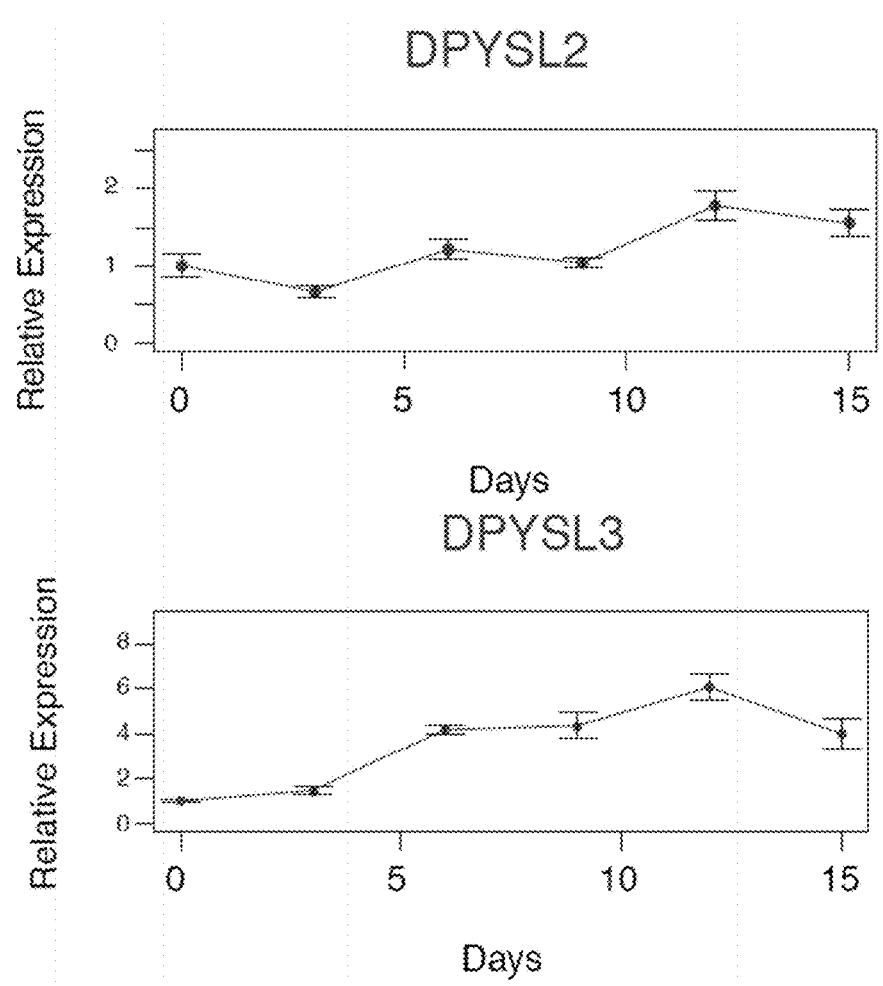

FIG. 8: Assessment of DPYD in epithelial to mesenchymal transition (A) Quantitative PCR analysis of DPYS and UBP1 expression in HMLE-TWIST cells using. Results were normalized to the expression level in human liver tissue.

(B) Expression of DPYSL2 and DPYSL3 in HMLE-TWIST cells as determined using quantitative PCR.

(C) Time course showing DPYSL2 and DPYSL3 expression in HMLE-TWIST cells during tamoxifen treatment relative to expression at time 0 (start of treatment) as determined using quantitative PCR.

Figure 9:
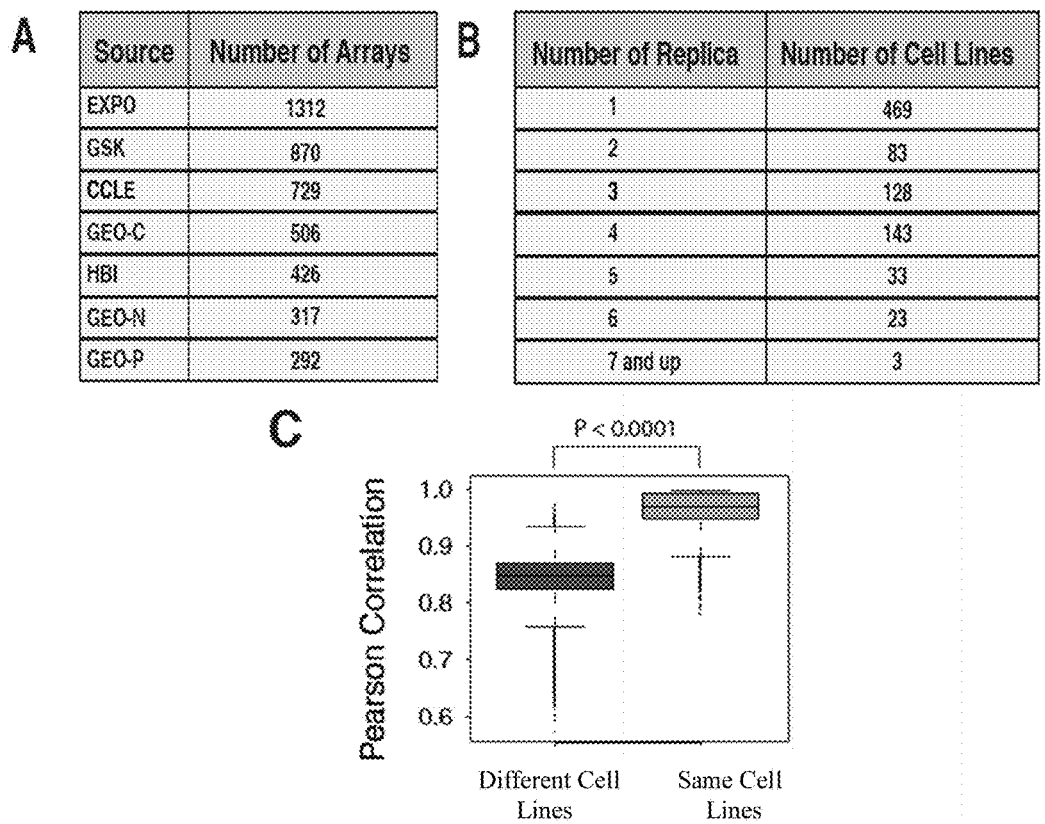
Figure 9:
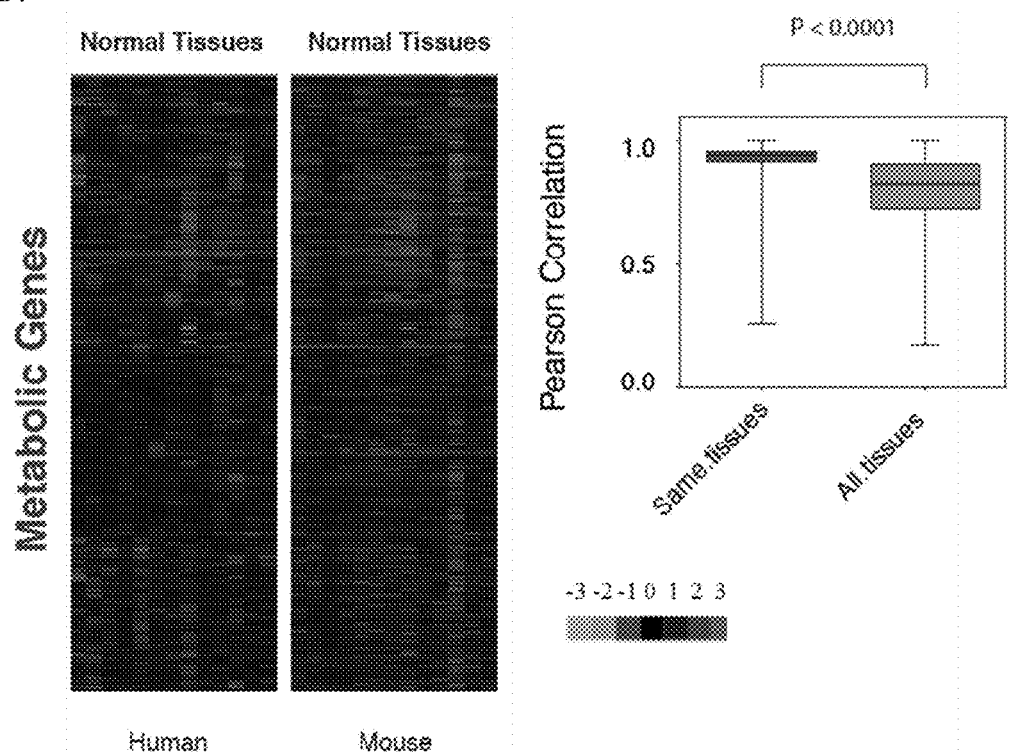
Figure 9:
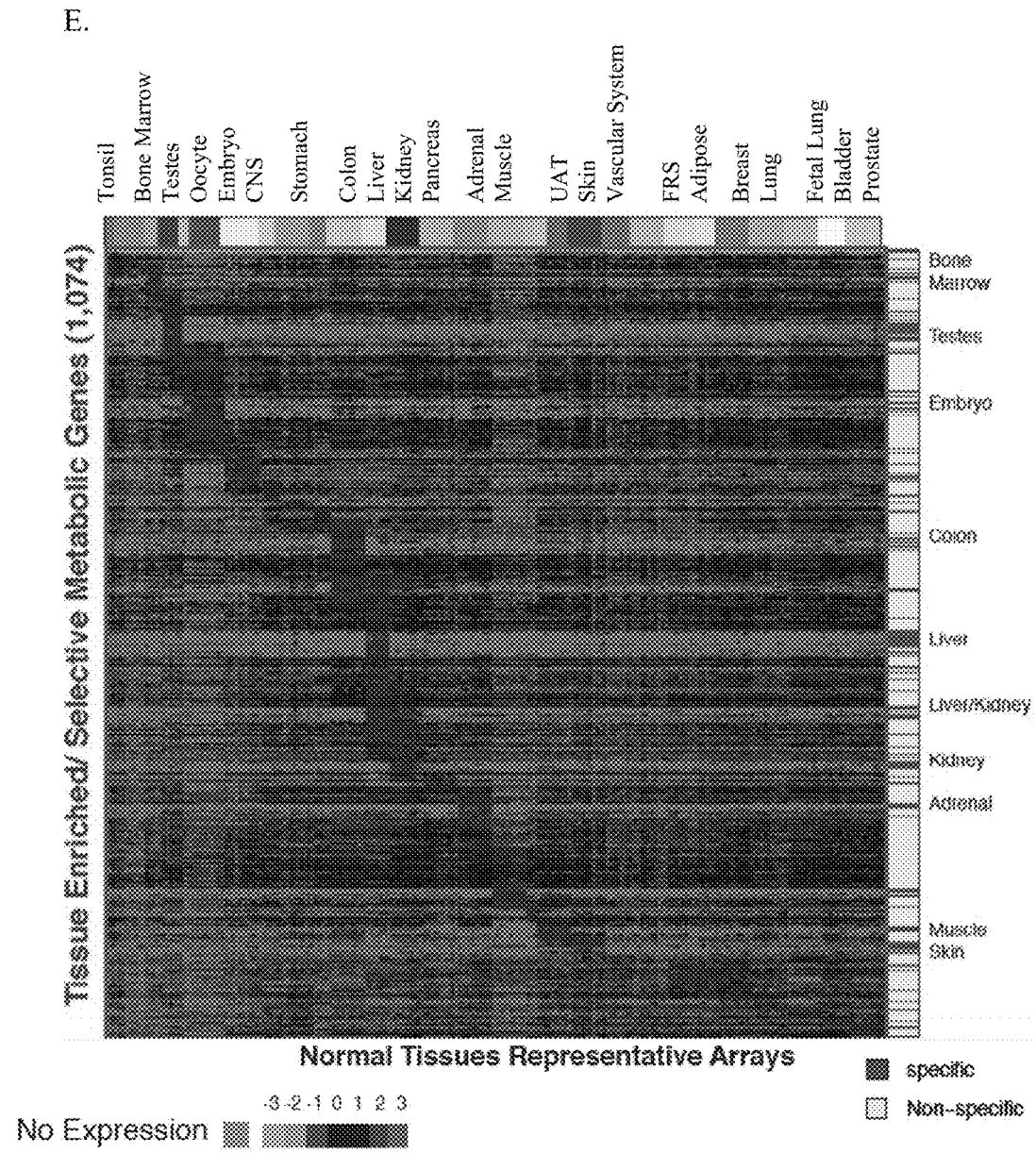
Figure 9:
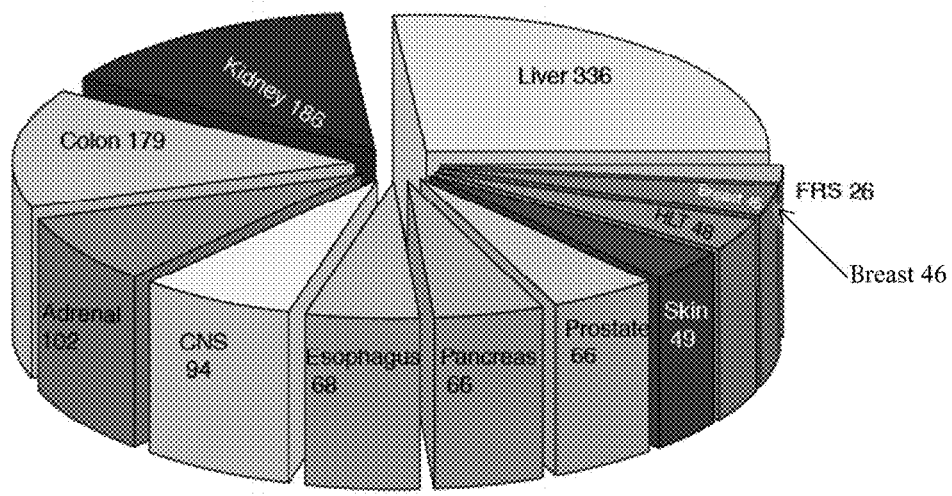
Figure 9:
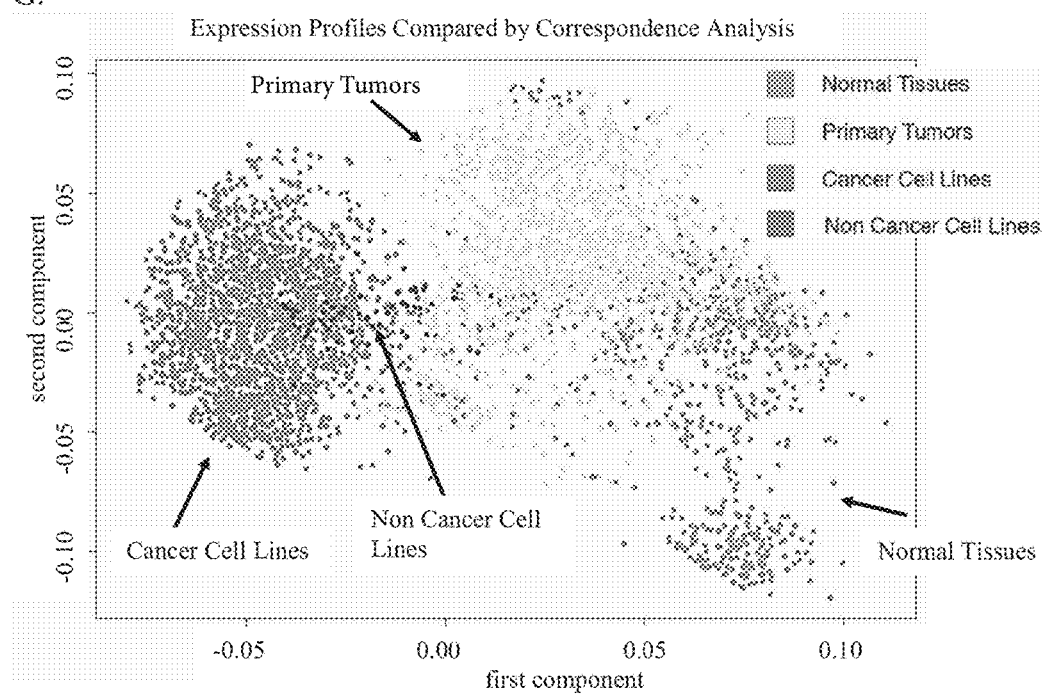
Figure 9:
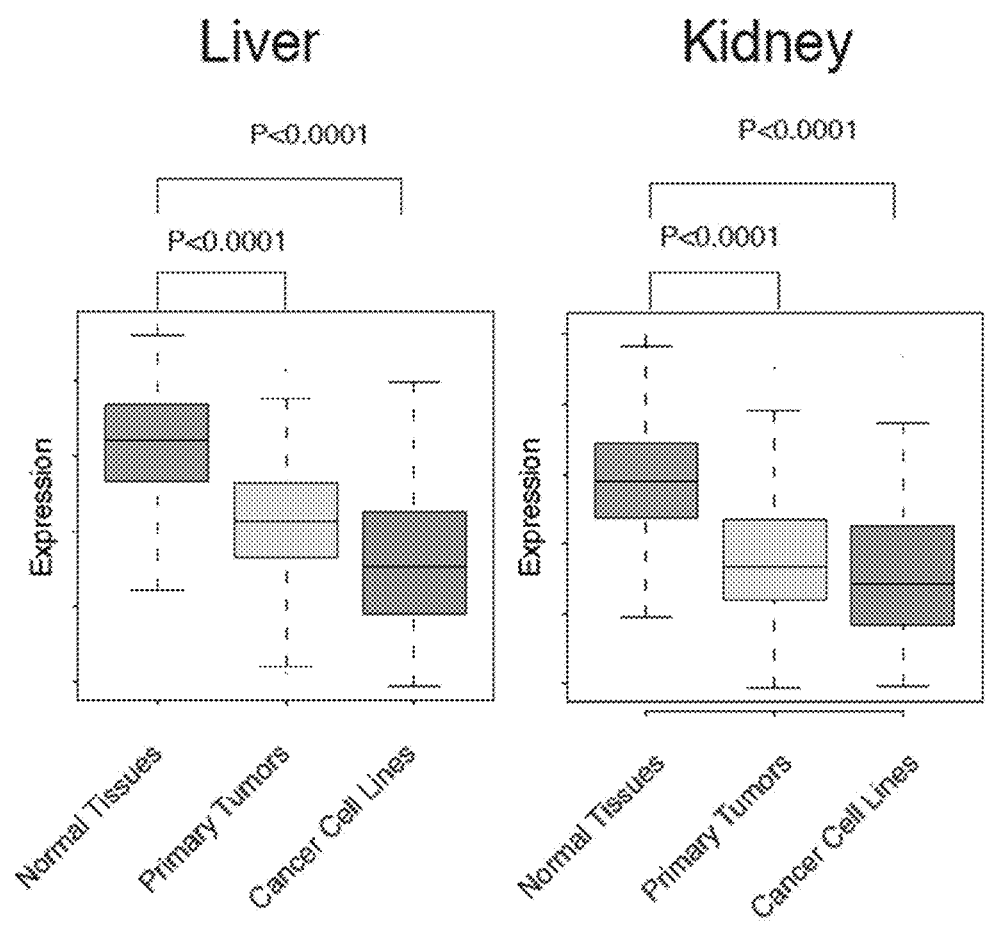

FIG. 9: Gene expression analysis demonstrates cancer-dependent metabolic remodeling (A) The "MERAV" database was generated from a variety of sources. A table representing the number of arrays from the different sources is shown.

(B) Most cell lines are represented by more than one array. A table representing the replica of cell lines arrays is shown.

(C) Same cell lines are highly similar, regardless of the source from which array data for that line was obtained. Pearson correlation was measured between the same cell lines and different cell lines. The results are presented as box plot. The enrichment for same cell line correlation was quantified using Student T test.

(D) Mouse and human normal arrays demonstrate a similar gene expression pattern. Mouse and human metabolic expression arrays were ordered by the corresponding genes and tissues. The correlation between the same tissues or different tissues was measured and represented as a box plot. The enrichment for same tissue correlation was quantified using Mann Whitney test.

(E) Isolation of the tissue selective genes. Tissue selective genes (1074 genes) were ordered based on their tissue specific expression. A heatmap was used to present the expression pattern. A light gray pixel indicates an absent value as indicated by the absent present call. The top bar represents the normal tissues. The right bar represents genes that are tissue specific.

(F) Number of enriched genes for each tissue. The tissue specific genes were determined for each tissue. Each slice in the pie chart represents the tissue and the number of tissue-specific genes.

(G) Normal tissues, primary tumors, and cancer cell lines separation. All of the database arrays were subjected to principal component analysis. Each array is noted by an arrow.

(H) Liver and kidney specific genes are down regulated in primary tumors and cancer cell lines. The expression of liver and kidney specific genes was determined in normal tissues, primary tumors, and cancer cell lines. The expression distribution of each gene set was presented as boxplot. The significance of the reduction in the gene expression in the primary tumors and cancer cell lines relative to the normal tissues was quantified using Student T test.

Figure 10:
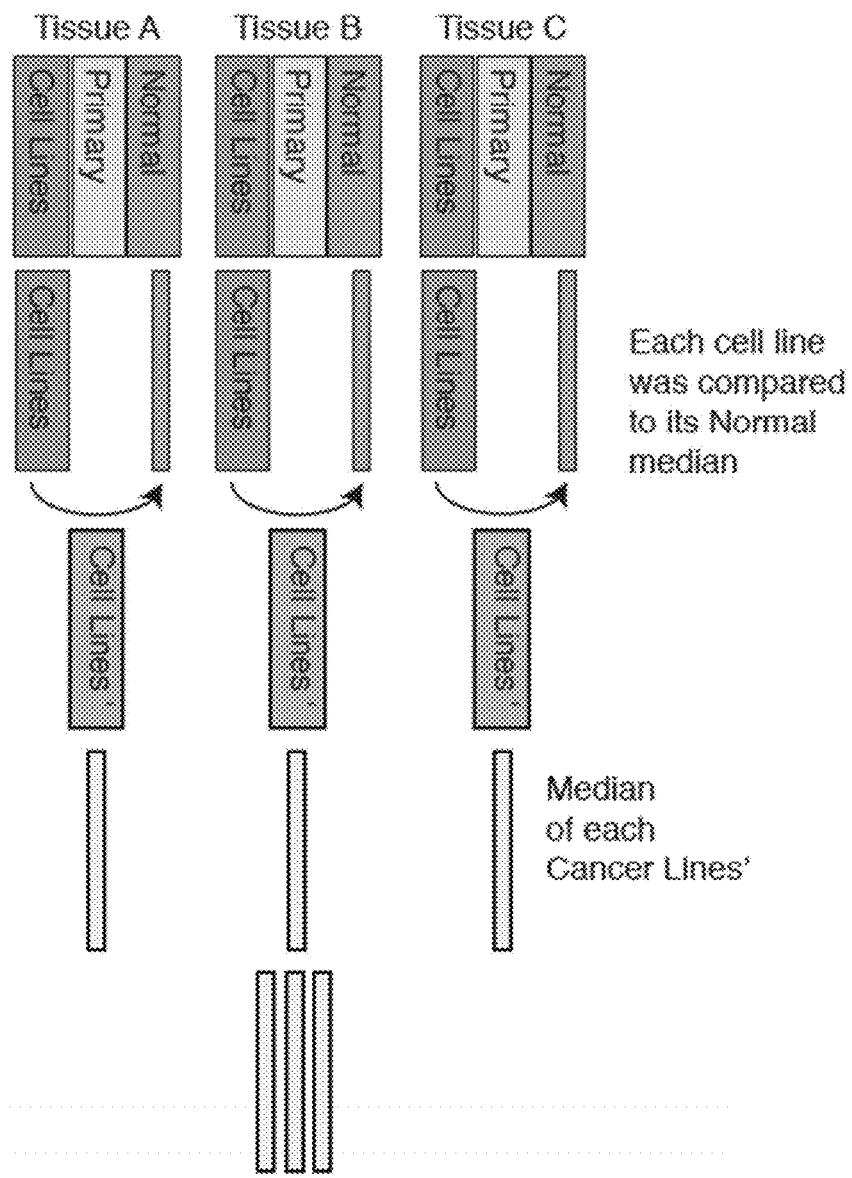
Figure 10:
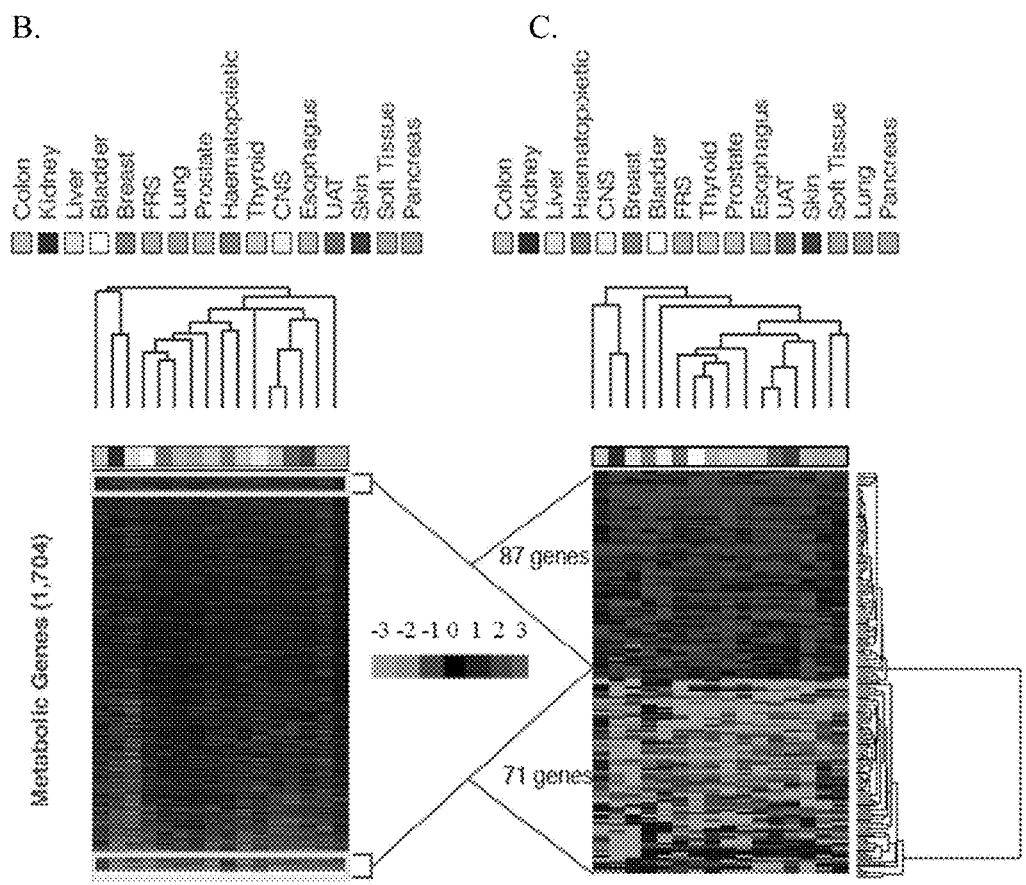
Figure 10:
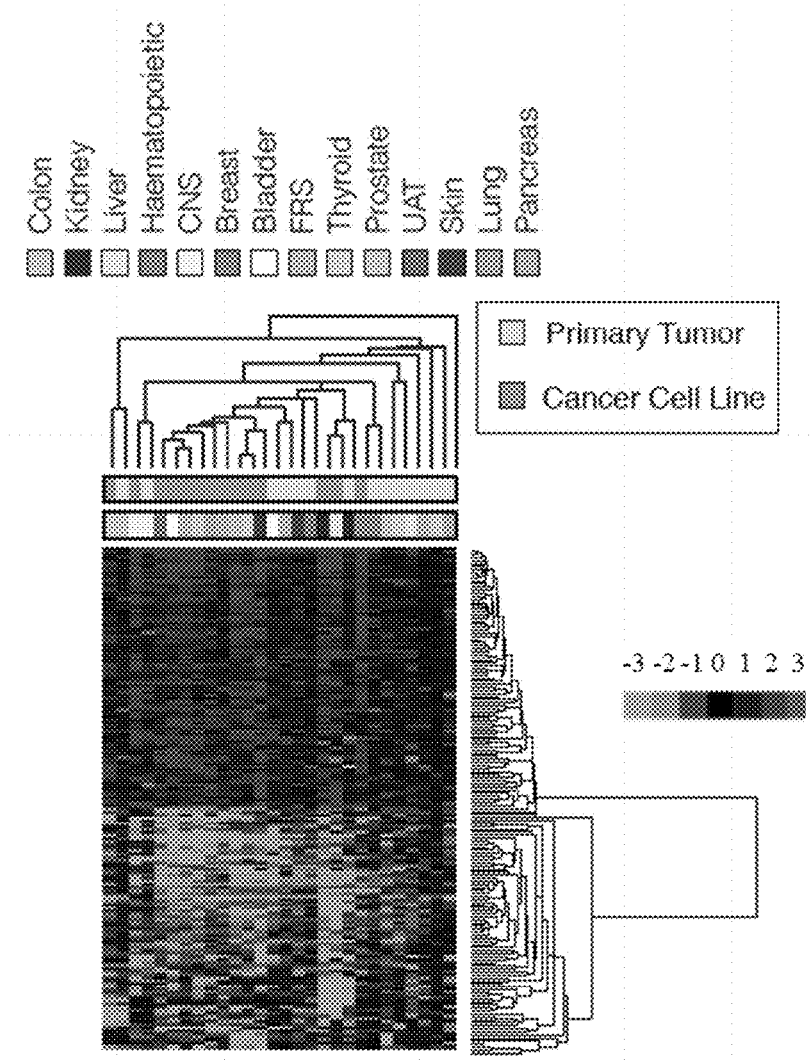
Figure 10:
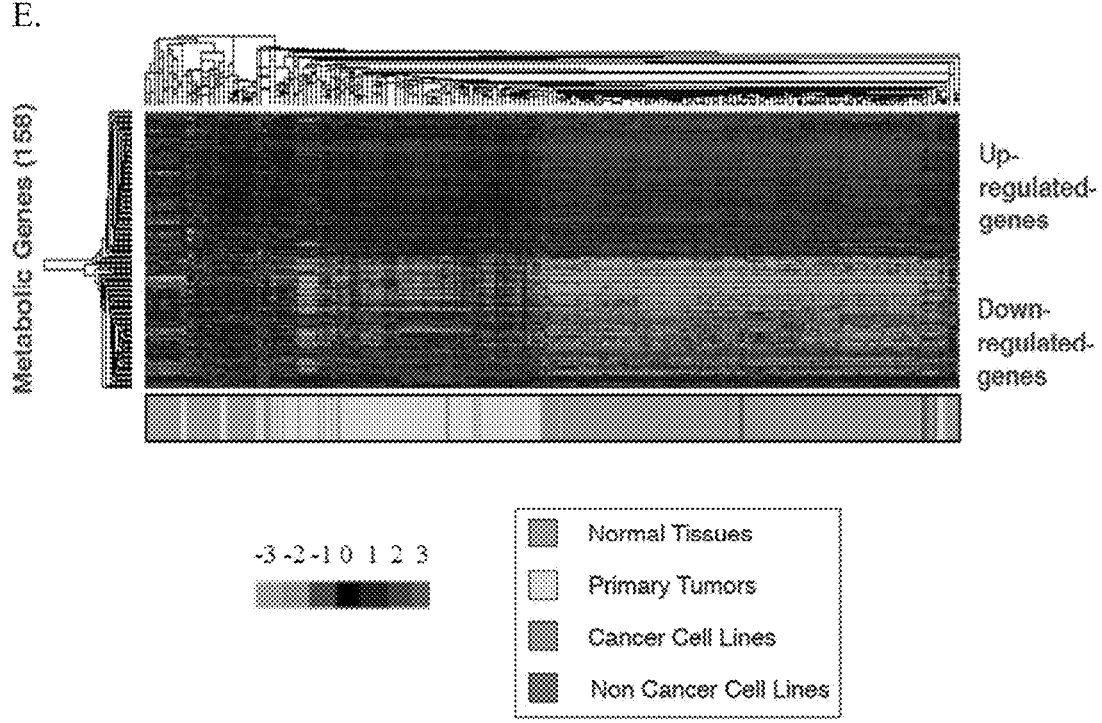
Figure 10:
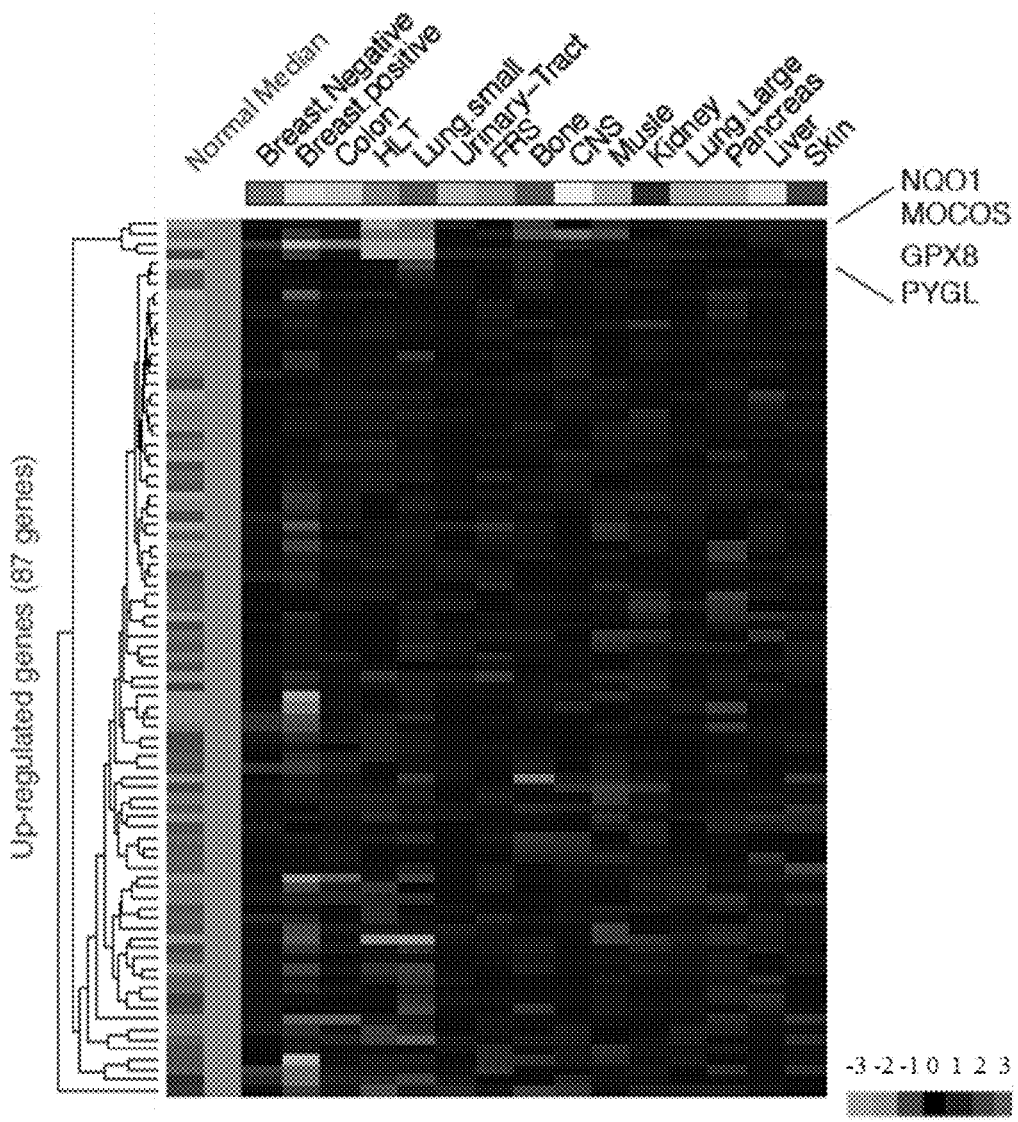

FIG. 10: Characterization of the universal metabolic gene set.

(A) A schema representing the isolation of the universal metabolic gene set. In the database there are 16 tissues that are represented by normal tissues, primary tumors, and cancer cell lines. The median expression level of each gene in each cell line from the same tissue was determined.

(B) The metabolic genes were ordered by the most expressed to the least. A heatmap representing the expression of each metabolic gene in primary tumors or cancer cell lines relative to normal tissues was generated. Each column represents the tissue median. The tissues are represented with intensity bars.

(C) Isolation of the universal metabolic gene signature. A heatmap representing the universal metabolic gene signature that is composed of 87 genes that are up regulated and 71 genes that are down-regulated throughout all or almost all the cancer cell lines. The tissues are represented with top intensity bar.

(D) Universal metabolic gene signature expression in cancer cell lines and primary tumors. A heatmap representing the expression of each metabolic gene in cancer cell lines and primary tumors relative to normal tissues. The tissues are represented with top intensity bar.

Figure 1:
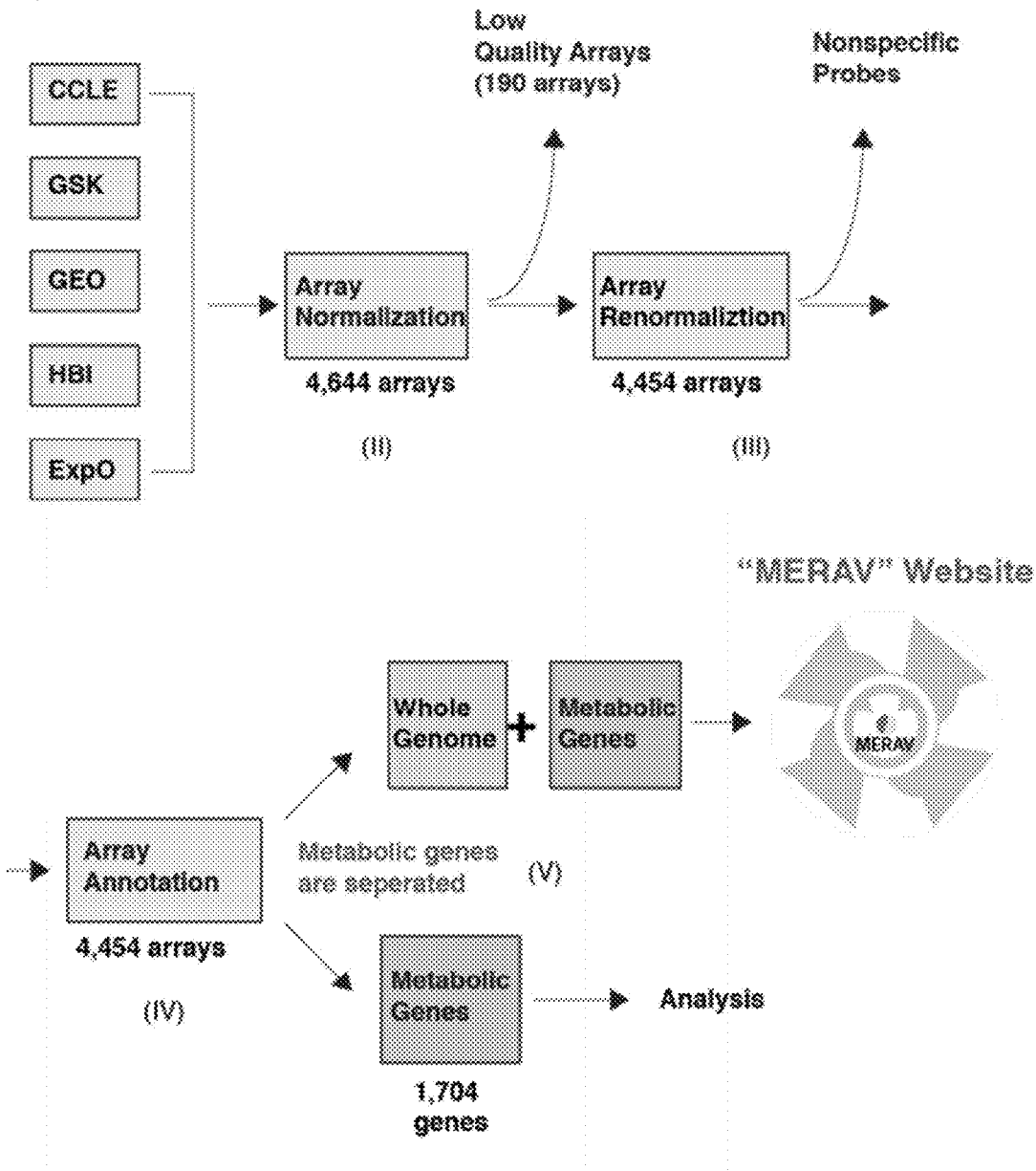
FIG. 1: Metabolic gene expression analysis demonstrates cancer-dependent metabolic remodeling (A) Scheme for generating the "MERAV" database. (I) Human gene expression data was collected from the following resources: Cancer Cell Line Encyclopedia (CCLE), GlaxoSmithKline (GSK), Gene Expression Omnibus database (GEO), Human Body Index (HBI), and Expression Project for Oncology (ExpO). (II) The data was assembled and normalized together, flowed by quality control, and low quality arrays were removed. (III) The database was renormalized, followed by the extraction of nonspecific probes. (IV) The arrays were annotated to obtain a unified annotation. (V) The data was generated as the "MERAV" website, or analyzed (Metabolic genes only).
Figure 1:
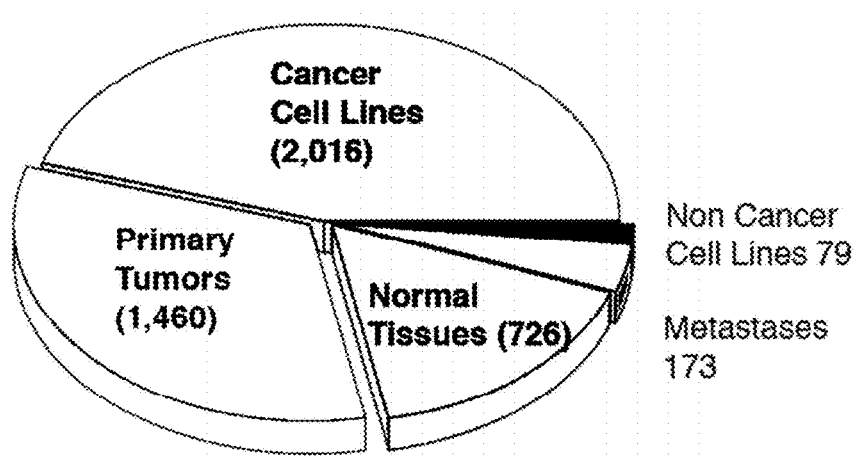
Figure 1:
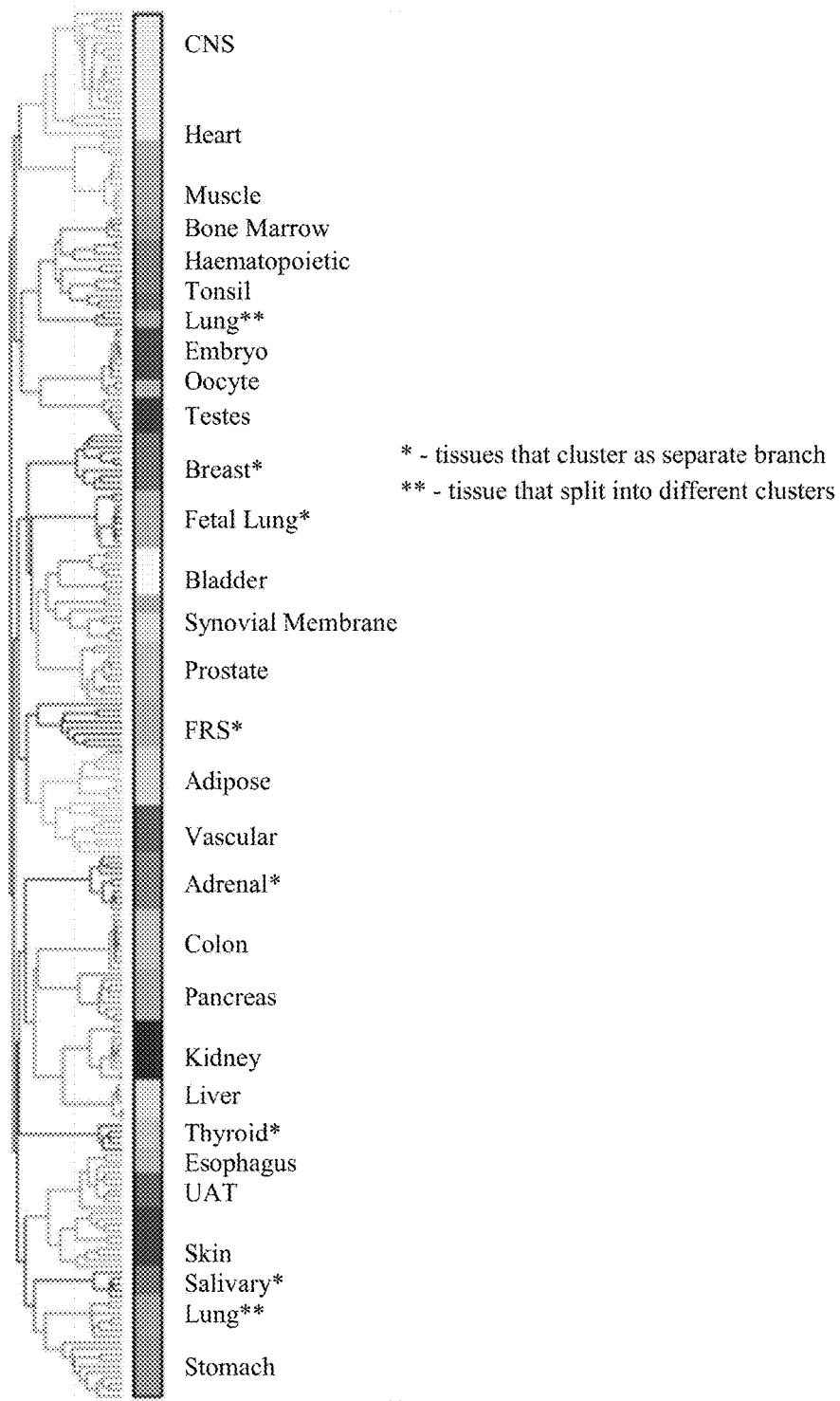
Figure 1:
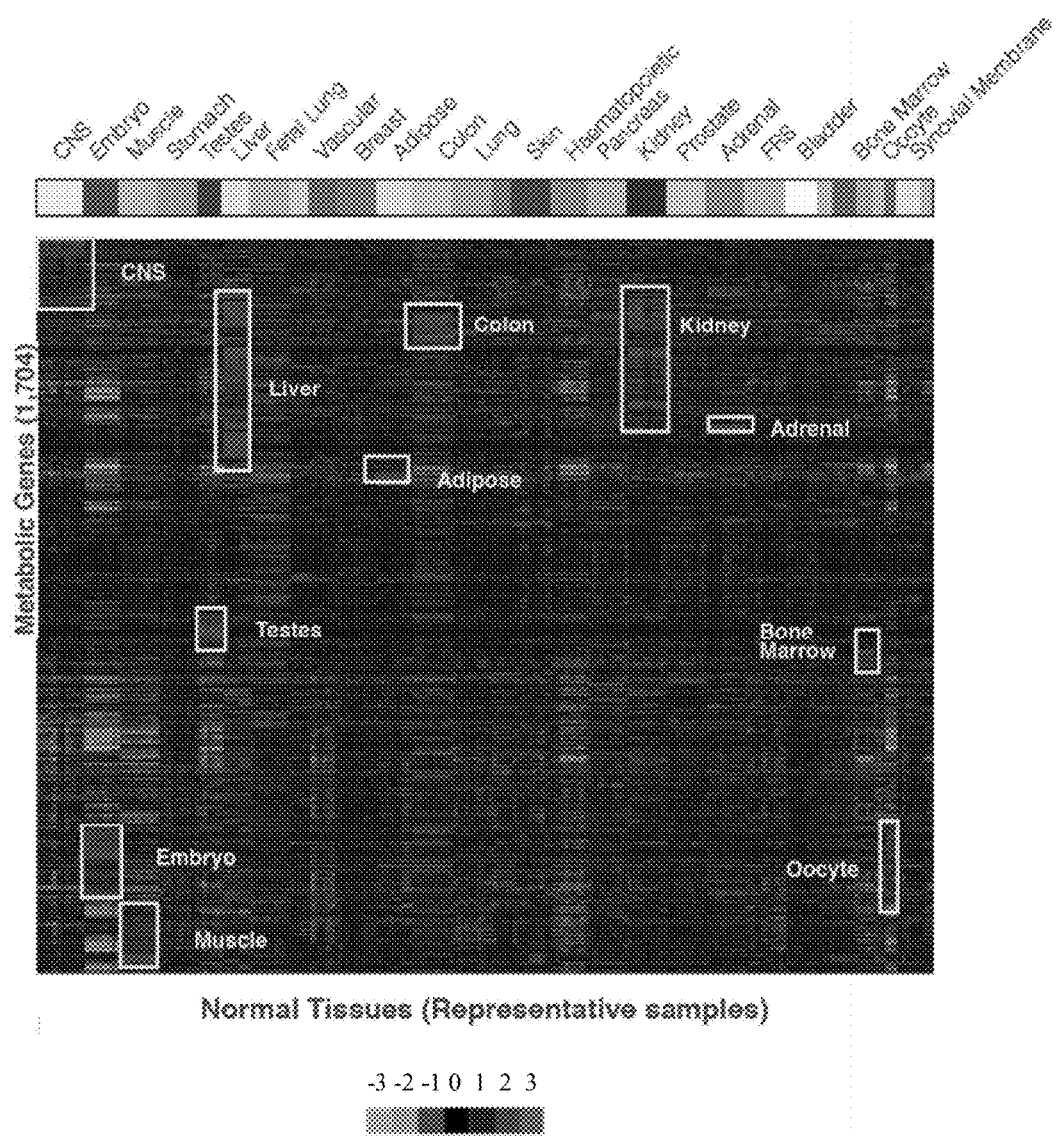
Figure 1:
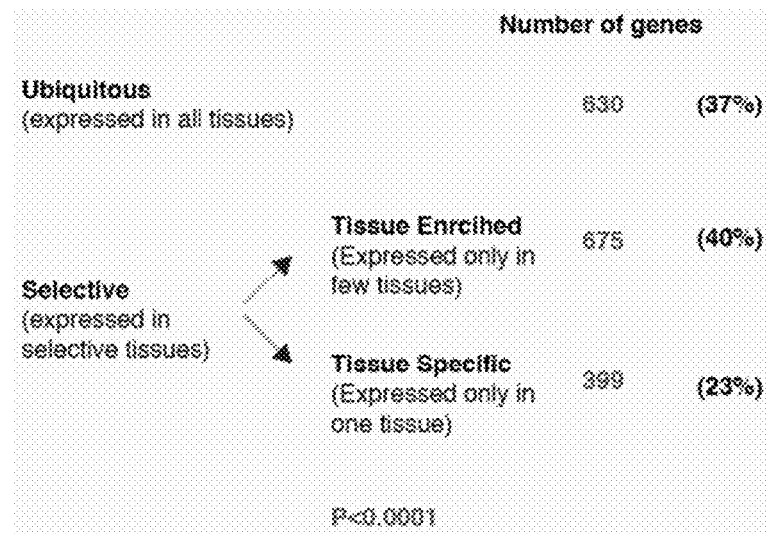
Figure 1:
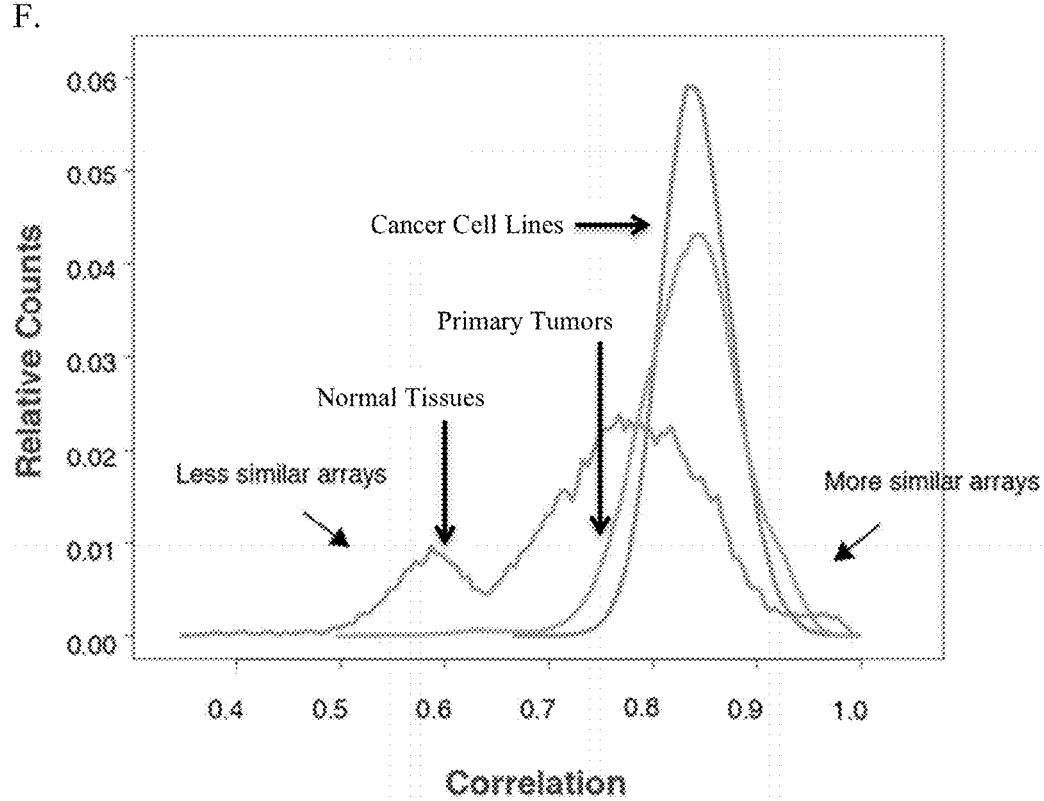
Figure 1:
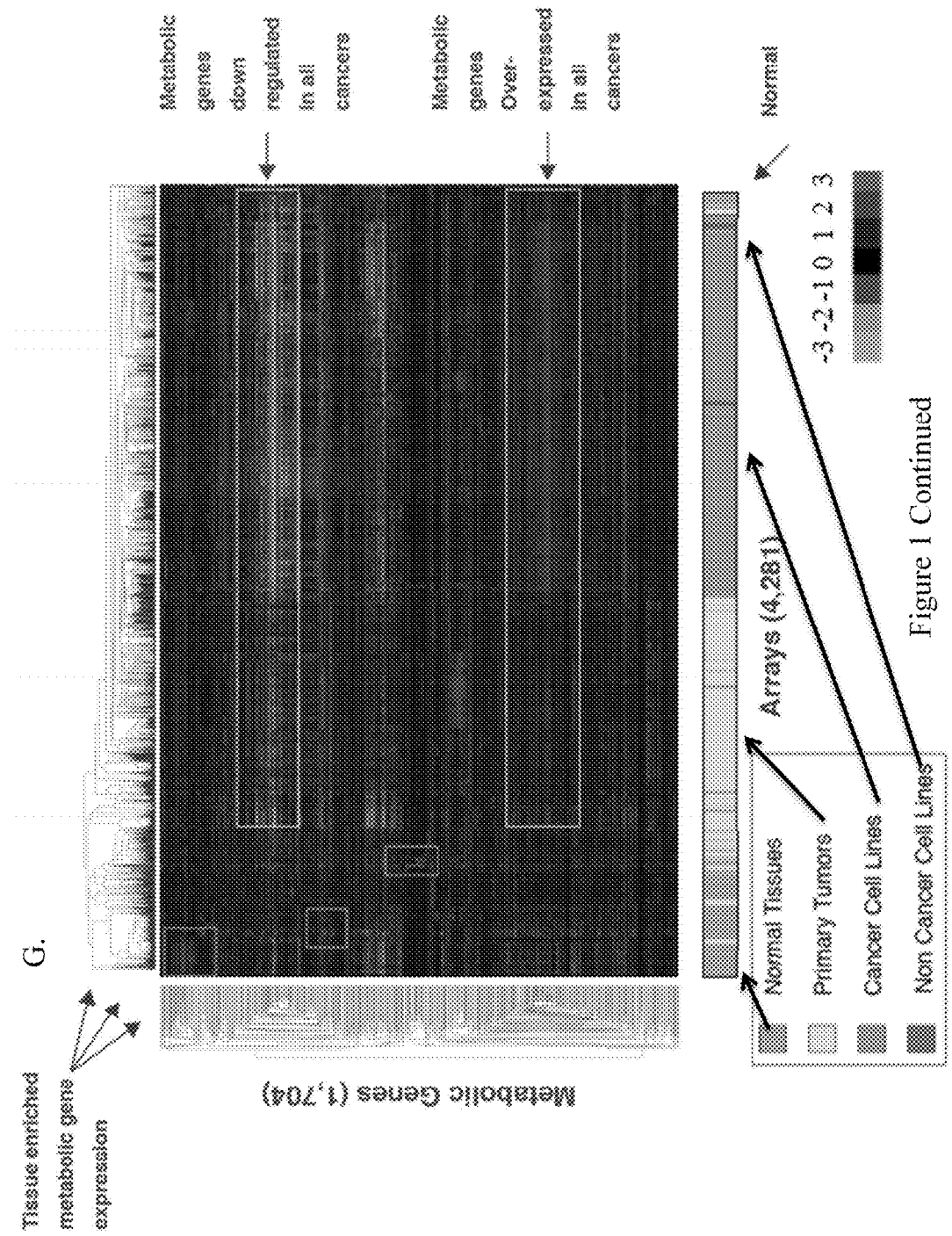

(E) Universal metabolic gene signature expression in cancer cell lines and primary tumors. A heatmap representing the relative to normal expression of each metabolic gene in all the arrays. The arrays cluster order is similar to FIG. 1G, however limited to the universal signature. The distribution of normal tissues, primary tumors, and cancer cell lines is presented by bottom intensity bar.

(F) Several of the universal up-regulated metabolic genes are not expressed in all tissues. A heatmap representing the relative to all expression of each up-regulated gene in the tissues median. The median expression of those genes in normal tissues is also presented (Normal median). The tissues are represented with top intensity bar. The names of selected genes is demonstrated.

(G) Most antimetabolite drugs targets used in cancer treatment designed against nucleotide biosynthesis are in the universal metabolic gene signature. A table demonstrating the clinically used antimetabolite drugs and their targets is presented. The targets are separated based on their presence or absence from the universal metabolic gene signature.

Figure 11:
Figure 11:
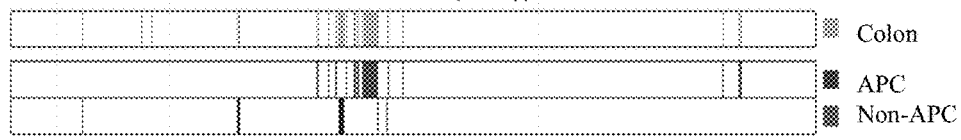
Figure 11:
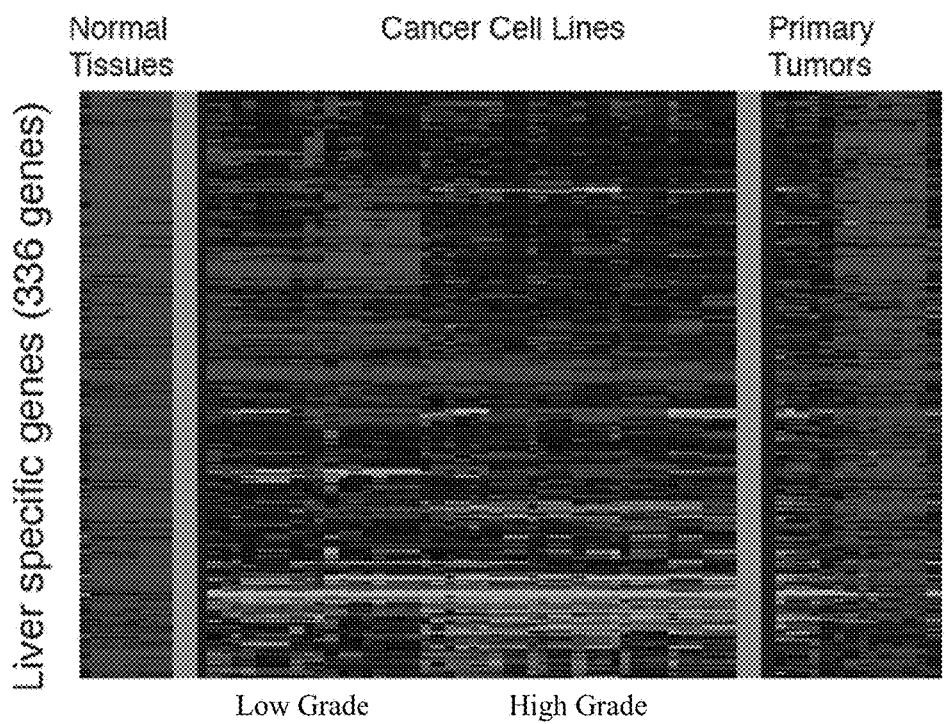
Figure 11:
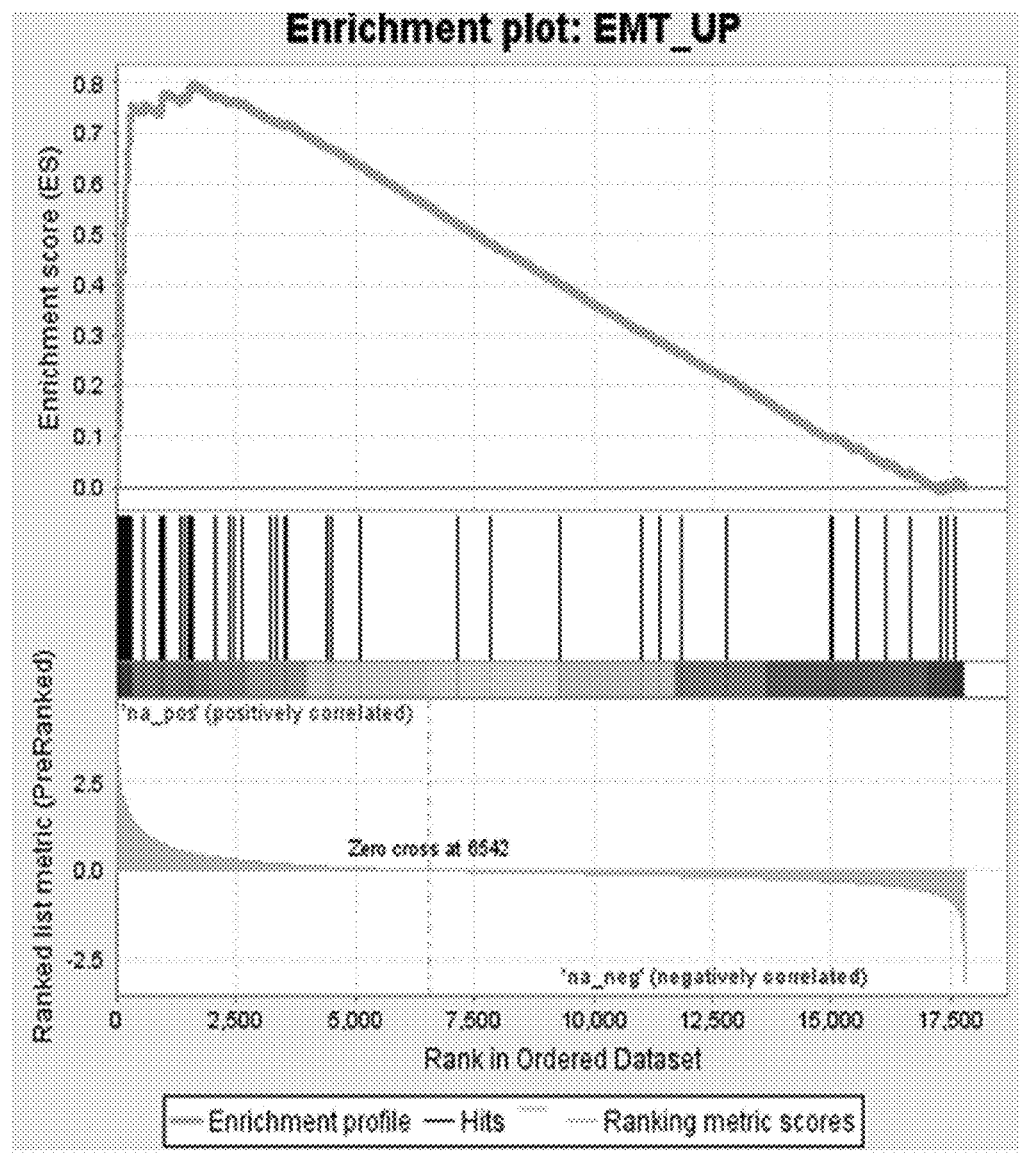
Figure 11:
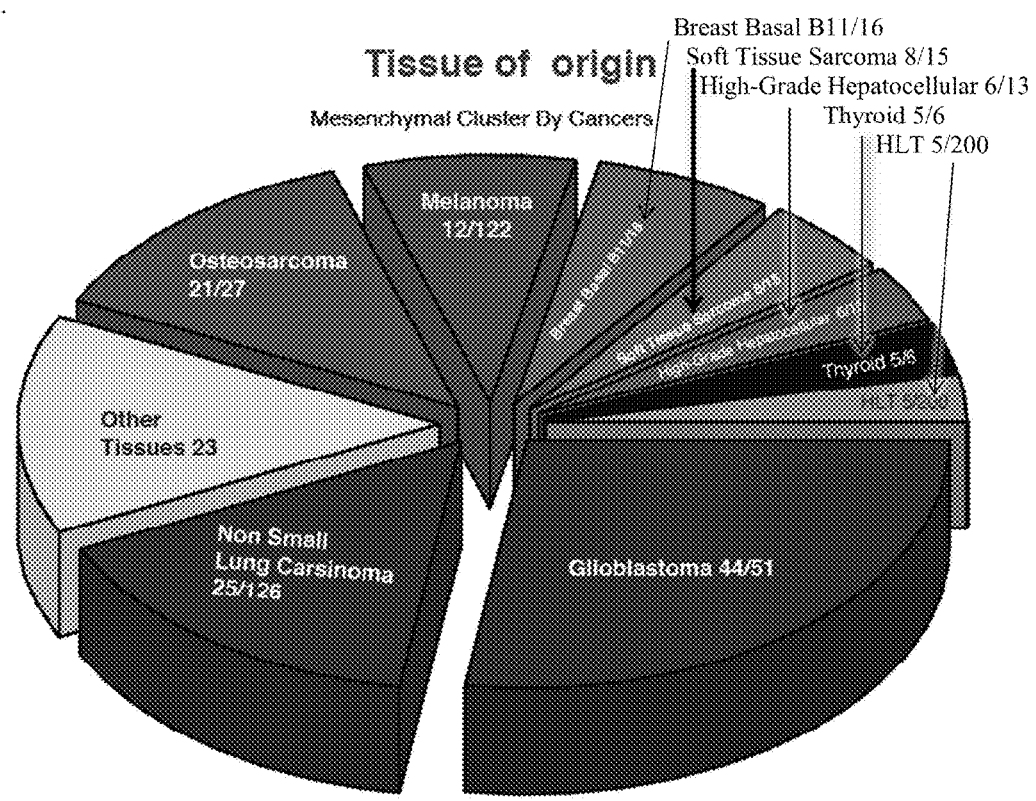

FIG. 11: Metabolic gene mesenchymal signature is found in various carcinoma cell lines originating from different tissues.

(A) Lung and colon cell lines distribution by cancer subtype. The cancer subtype of each lung and colon array was determined and is represented by the label on the right. The order of the arrays is identical to FIG. 3.

(B) Hepatocellular carcinoma cell lines can be divided between low and high grade. Liver specific gene expression in liver normal tissue, hepatocellular cell lines, and primary tumors. The arrays were analyzed to obtain the ratio to the normal tissues median of median and subjected to array-based hierarchical clustering. The arrays were separated with gray line based on the type.

(C) Gene Set Enrichment Analysis (GSEA) analysis of mesenchymal derived cell lines shows enrichment of EMT genes. For each gene the relative expression between the mesenchymal cluster to the rest of the arrays was determined. The ratio served as rank for GSEA analysis. The false discovery rate (FDR) q-values is provided by GSEA.

(D) Metabolic mesenchymal signature is derived from a diverse set of tumors. A pie chart representing the tumor of origin for each cell line located in the mesenchymal cluster is shown. The numbers represent the number of cell lines relative to all the cell lines from the same given tumor type. HLT=Haematopoietic and lymphoma tumors.

Figure 12:
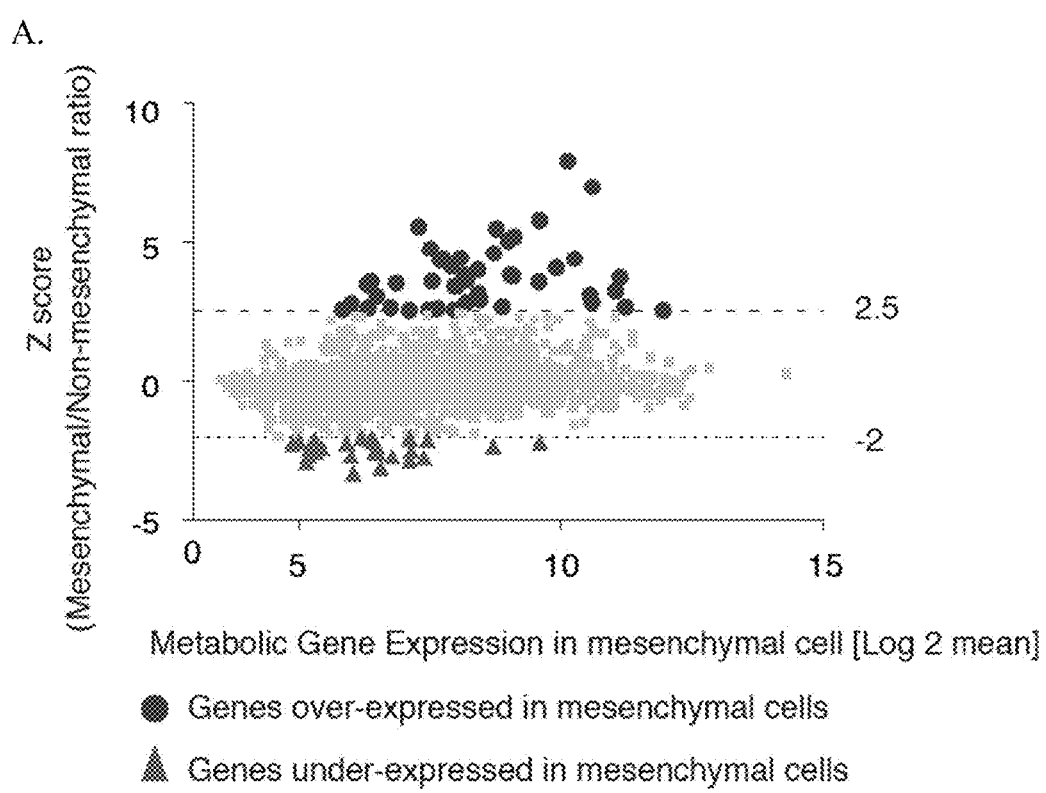
Figure 12:
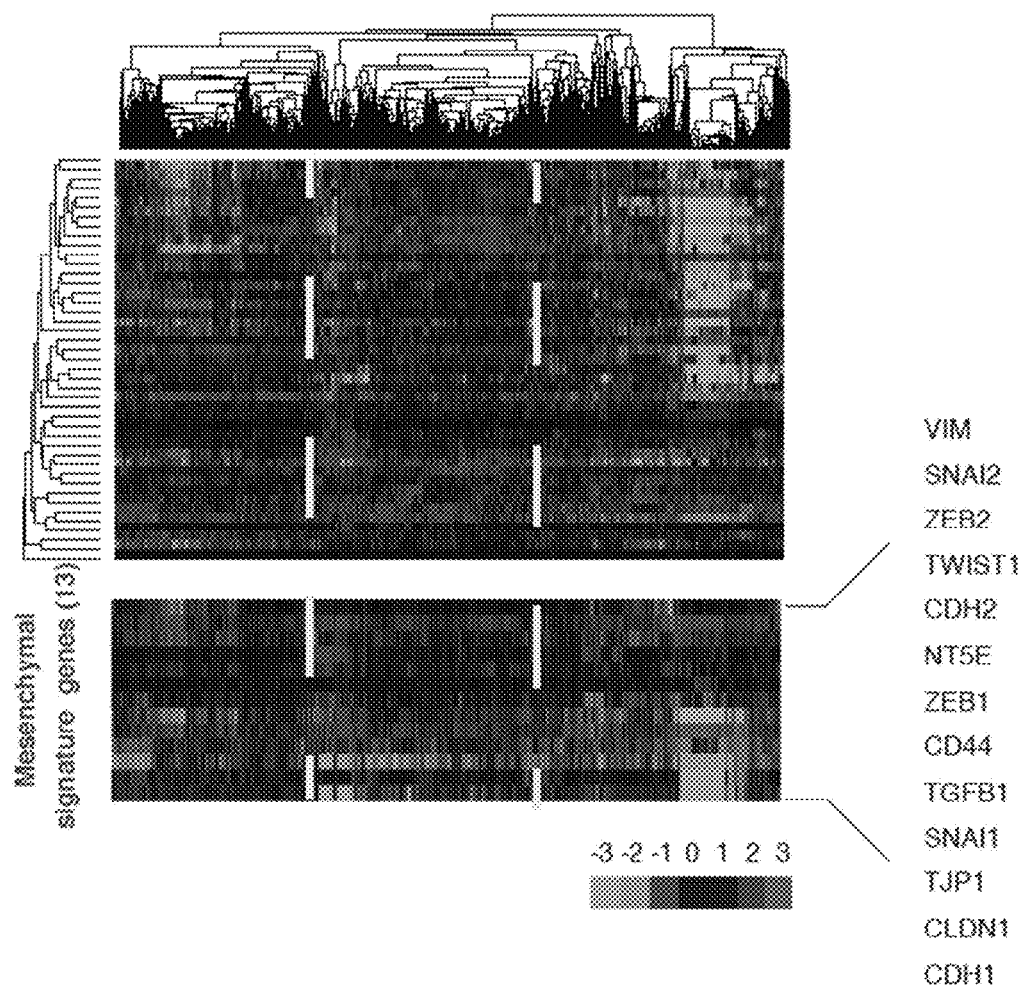
Figure 12:
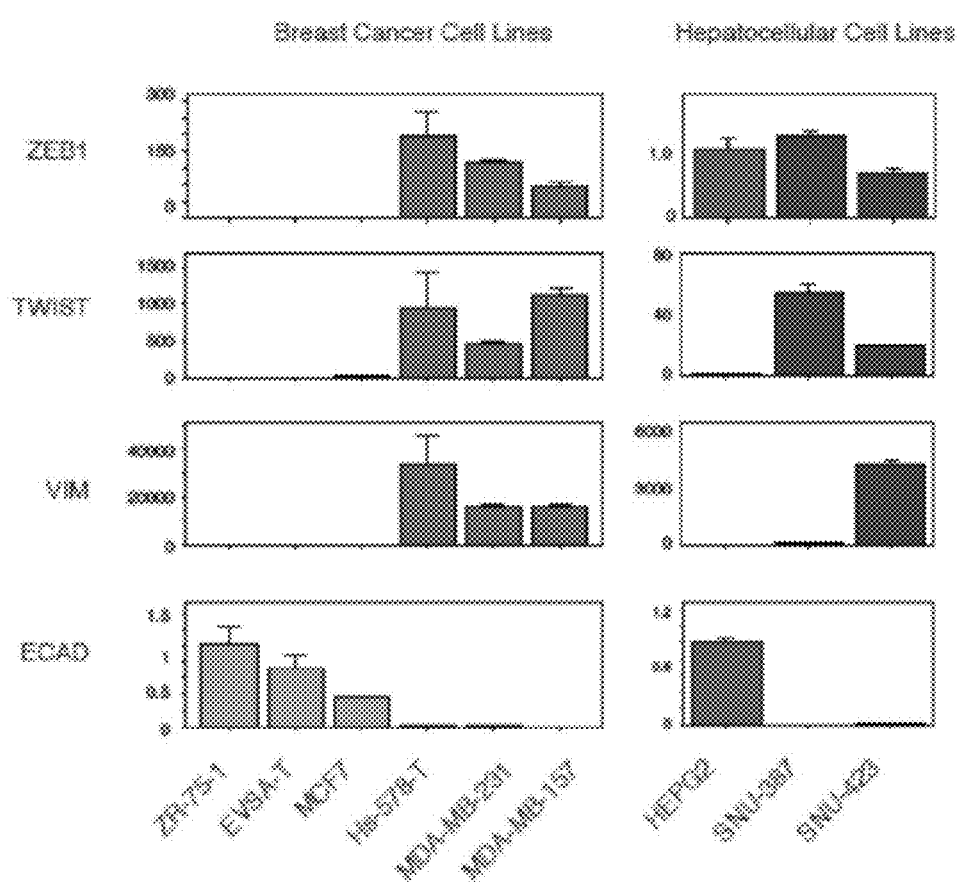

FIG. 12: High-grade carcinoma cell lines express a metabolic-gene mesenchymal signature (A) Isolation of the metabolic-gene mesenchymal signature. The cell lines (including both the cancer cell lines and non-cancer cell lines) were divided into two groups, mesenchymal and non-mesenchymal. For each metabolic gene the mean expression in each group was determined. The Z-score for each gene was calculated by determining the log 2 ratio between the two groups mean. The plot represents the Z-score (Y axis) vs. the mean expression (Log 2) of each metabolic gene in mesenchymal cell lines (X axis). Genes with Z-score higher than 2.5 (circle) or lower than −2 (triangle) were designated as the metabolic-gene mesenchymal signature 10 (MGMS), sometimes referred to as "metabolic mesenchymal signature". These genes are listed in Table 2. Table 2 also indicates, for each gene, whether it was upregulated or downregulated in mesenchymally derived cancer cell lines versus non-mesenchymally derived cancer cell lines.

(B) The metabolic mesenchymal signature is co-expressed with EMT markers. Two ways hierarchical clustering of 1,704 metabolic genes, and 1,460 primary tumors arrays. The values represent the log 2 over the primary tumors median of median. The upper panel heat map represents the metabolic genes expression in primary tumors, relative to primary tumor median of median. The lower panel heatmap representing known mesenchymal markers expression through all cancer cell lines is demonstrated.

(C) Known mesenchymal genes validation in breast and hepatocellular cancer cell lines. Quantitative RT-PCR analysis of several known mesenchymal genes expression in BasalB breast cancer and high-grade hepatocellular cancer cell lines. Error bars represent SEM.

Figure 13:
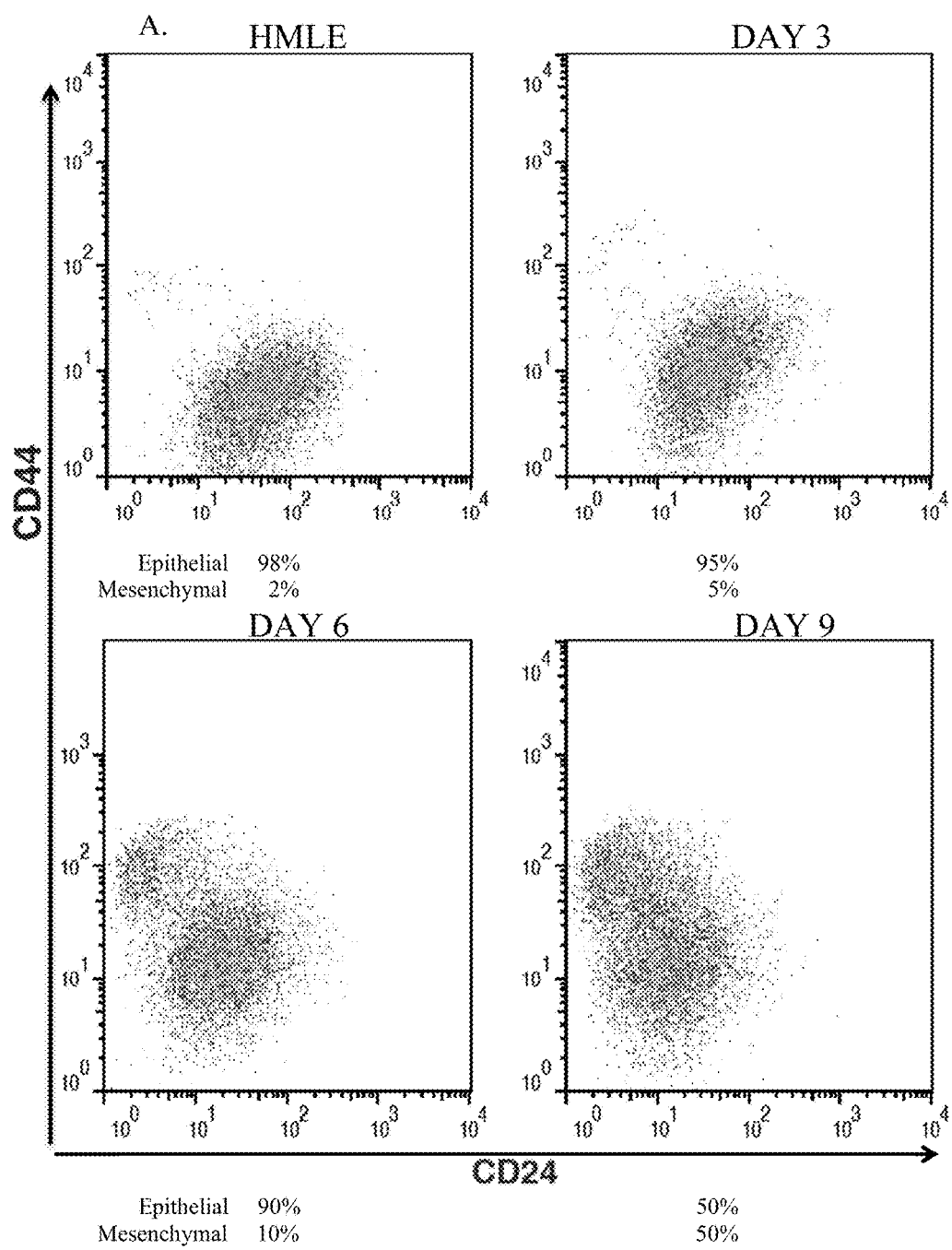
Figure 13:
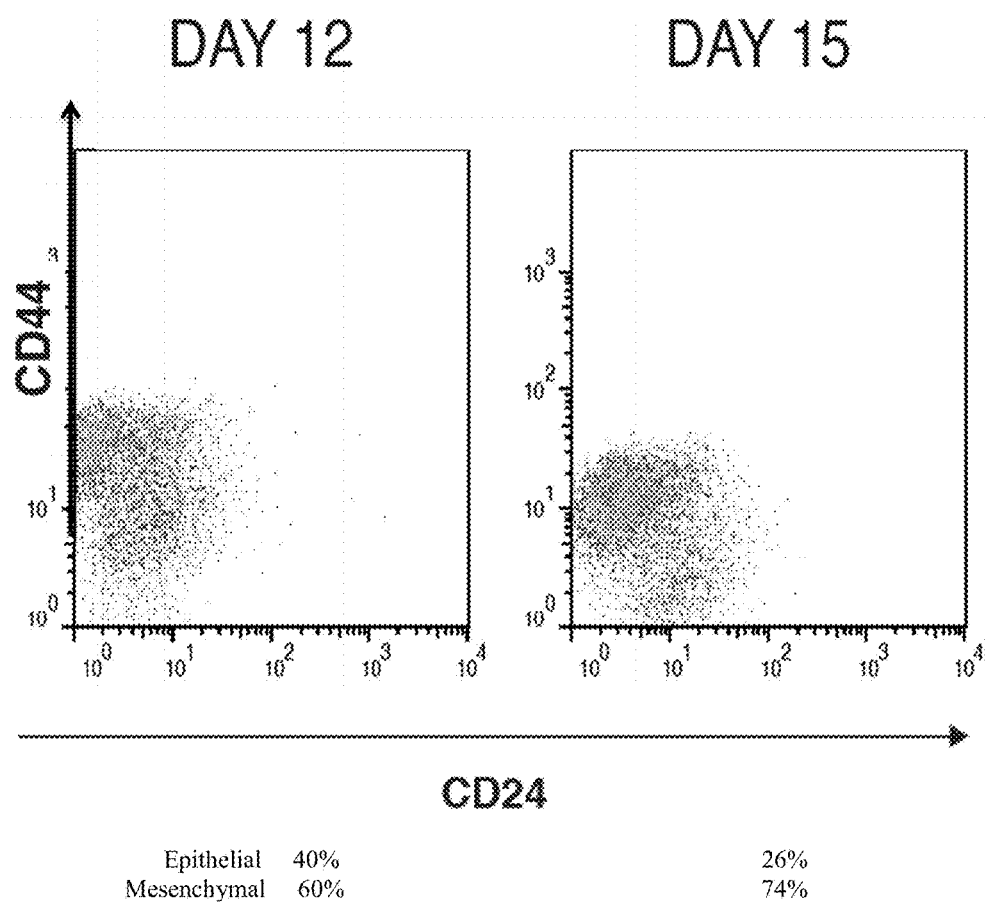
Figure 13:
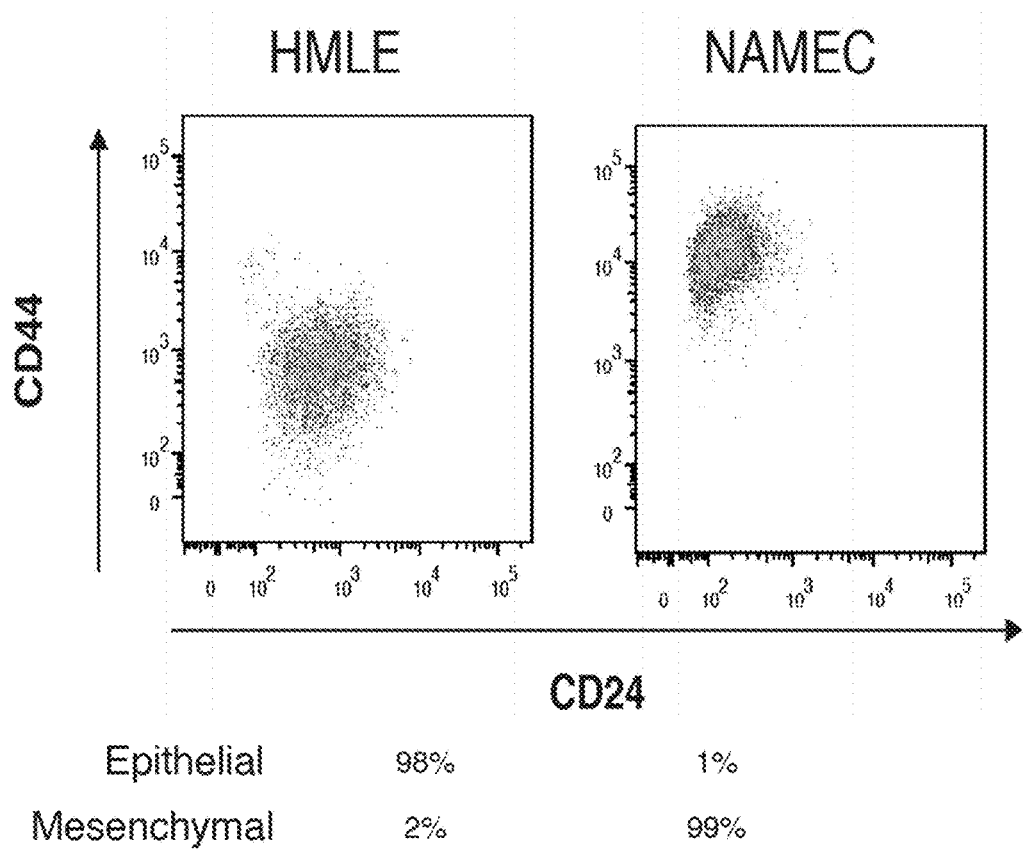
Figure 13:
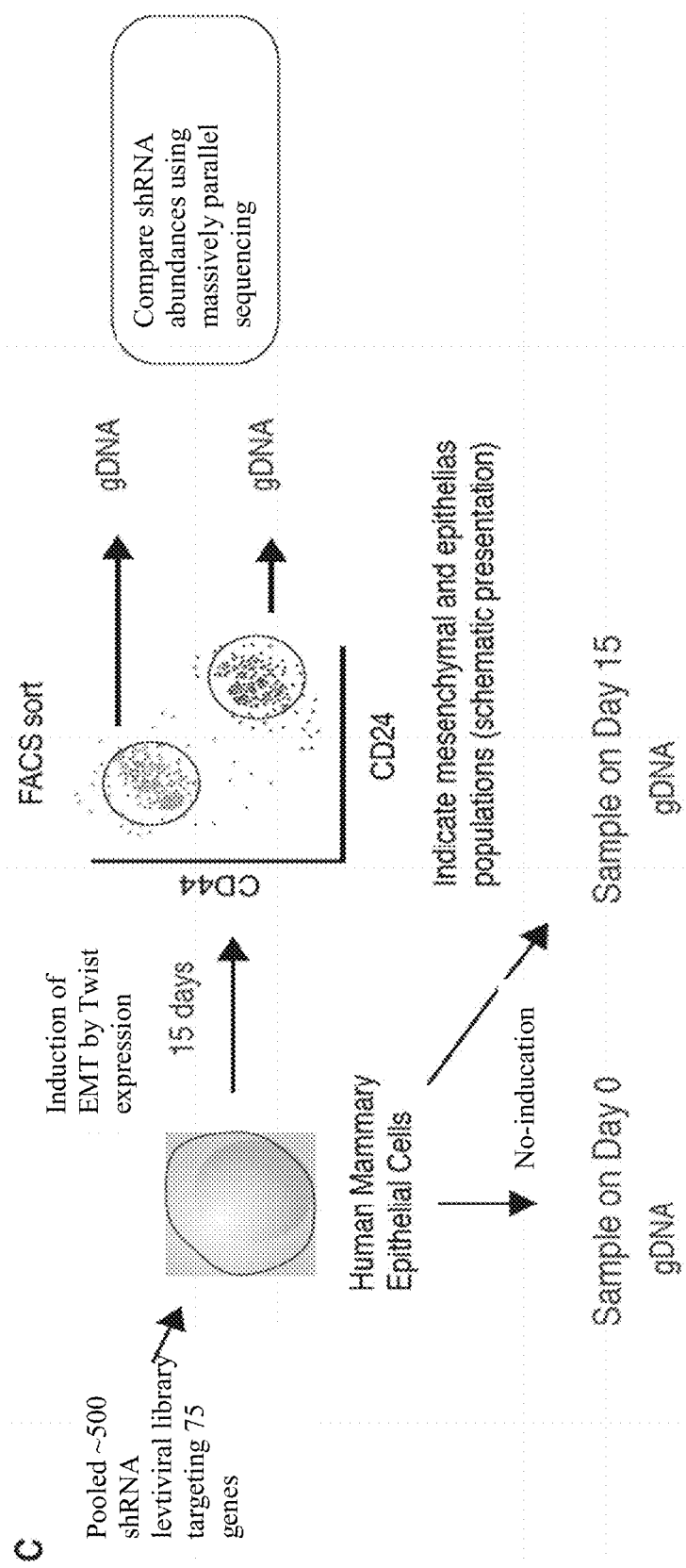

FIG. 13: Metabolic genes essentiality for epithelial to mesenchymal transition (A) HMLE EMT induction system. HMLE cells expressing a tamoxifen-activatable TWIST were treated with tamoxifen for 15 days. Every three days samples were collected and subject to FACS analysis using CD24-FITC and CD44-APC. The percentage of cells exhibiting a marker profile associated with epithelial or mesenchymal cells was determined. (Epithelial cell marker profile: $CD44^{low}/CD24^{high}$. Mesenchymal cell marker profile: $CD44^{high}/CD24^{low}$.)

(B) FACS profile of HMLE untreated cells and NAMEC cells. Both cell lines were stained with CD24-FITC and CD44-APC.

(C) Outline of the EMT FACS based pooled screen assay. Outline of experimental design. gDNA, genomic DNA.

(D) A table summarizing the shRNA vectors targeting genes targeted in the screen. The genes are separated based on their groups.

Figure 14:
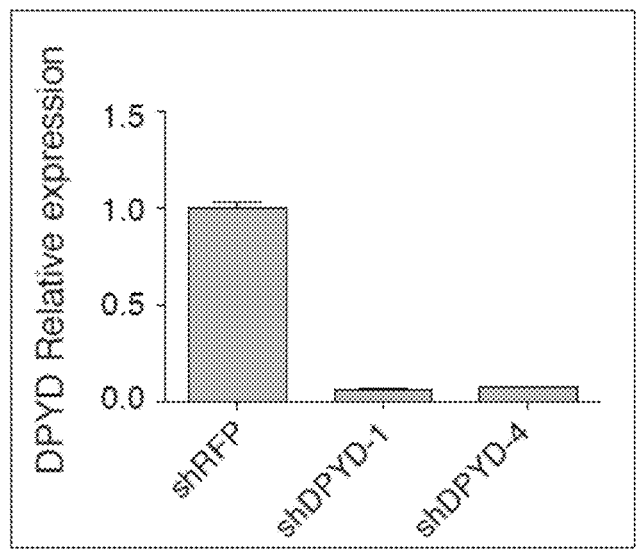
Figure 14:
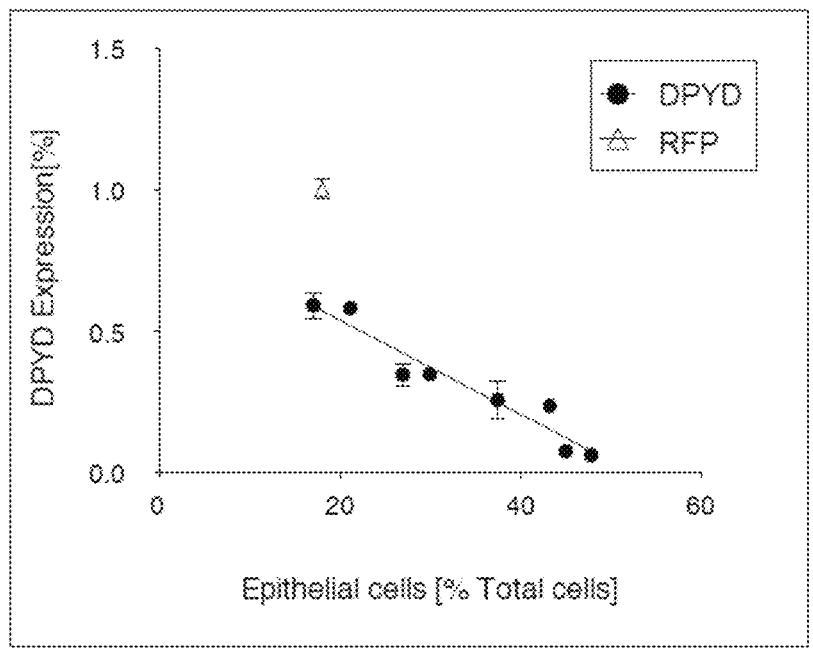
Figure 14:
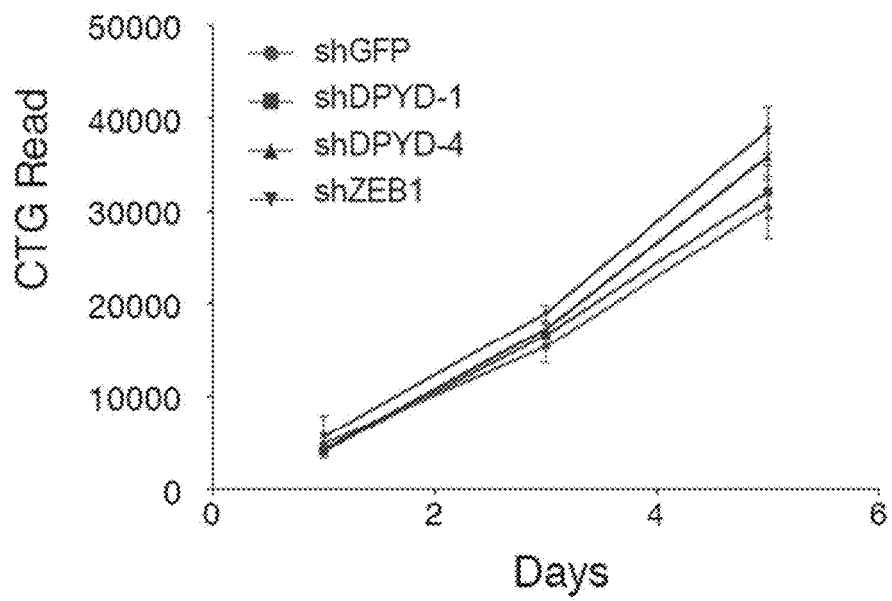
Figure 14:
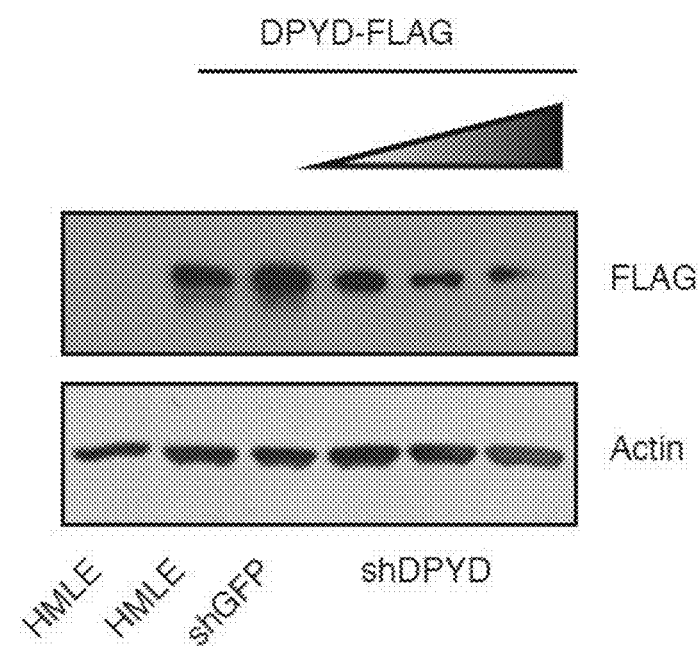
Figure 14:
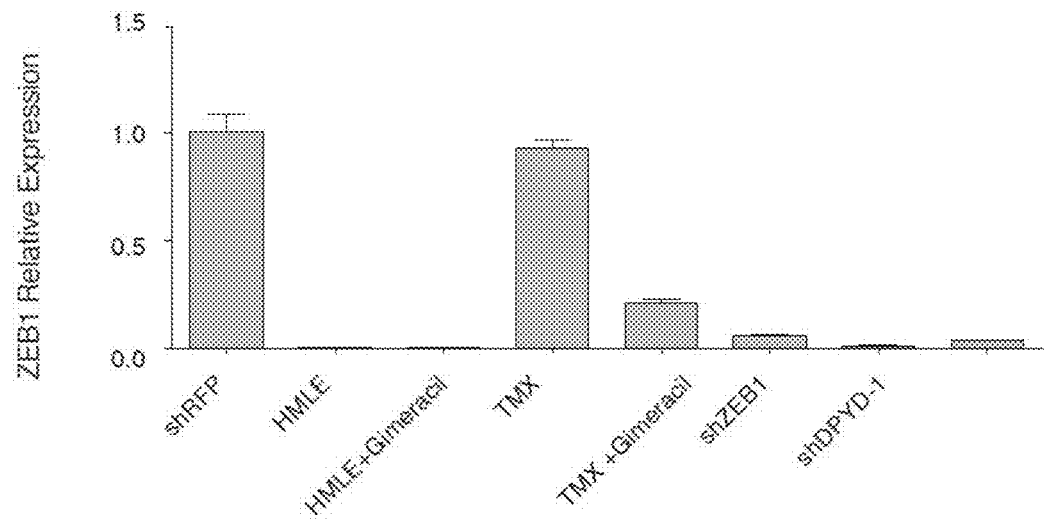
Figure 14:
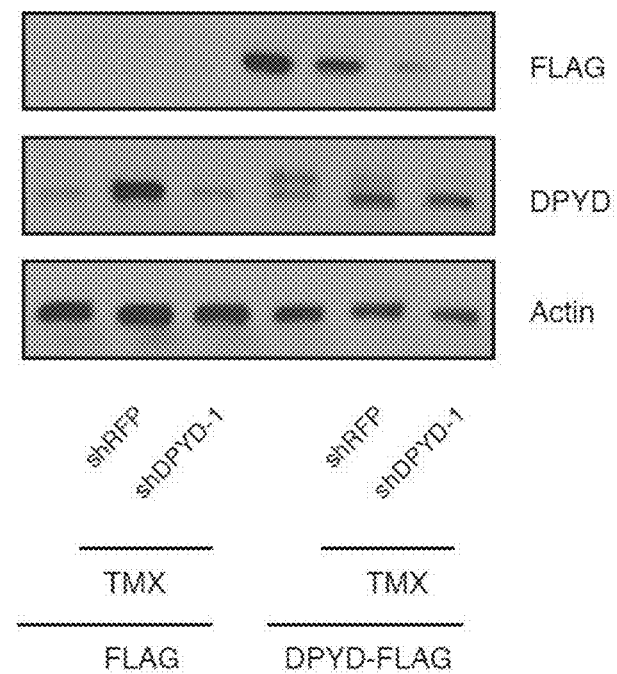

FIG. 14: Metabolic genes essentiality for epithelial to mesenchymal transition (A) Determining DPYD knockdown. HMLE cells lines were infected with the indicated hairpins. The RNA of the cells was isolated and DPYD expression level was determined by quantitative PCR.

(B) DPYD expression level correlated with epithelial cell phenotype. HMLE cells were infected with a variety of hairpins against DPYD and were treated with tamoxifen. The correlation between DPYD expression level and percent epithelial cells was determined by quantitative PCR (for expression level) and FACS analysis using CD24 and CD44 as markers ($CD44^{low}/CD24^{high}$ for epithelial cells). As evident in the figure, knockdown of DPYD expression correlated with increasing percentage of cells that retained an epithelial marker profile.

(C) DPYD knockdown does not affect proliferation. NAMEC cells were infected with the indicated hairpins. The proliferation rate was determined using Cell TiterGlo® (Promega).

(D) Determining DPYD expression level. DPYD-FLAG expression in the presence of increasing concentrations of shDPYD. Cell lysates were analyzed by immunoblotting for level of indicated proteins.

(E) DPYD knockdown affects ZEB1 expression level. HMLE cells were treated with the indicated treatment. The RNA level of ZEB1 was determined using quantitative PCR.

(F) DPYD expression level in the rescue experiments. DPYD expression level in the cells used for FIG. 6E. Cell lysates were analyzed by immunoblotting for level of indicated proteins.

Figure 15:
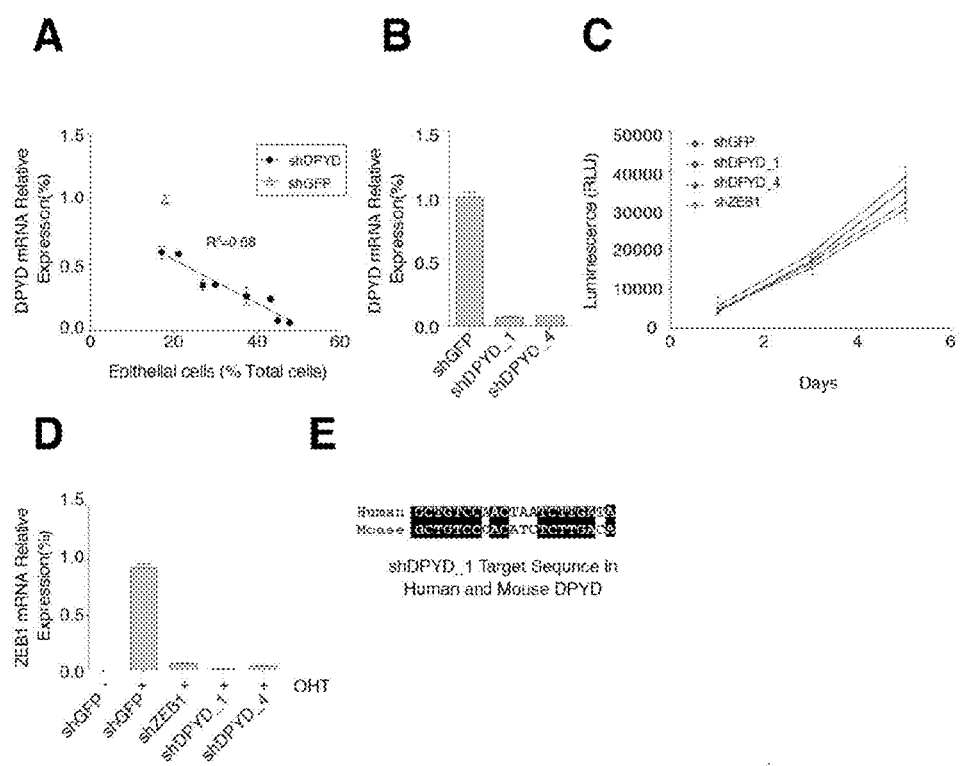

FIG. 15: DPYD expression (A) DPYD expression negatively correlates with the proportion of epithelial cells. HMLE-Twist-ER cells were infected with a variety of hairpins against DPYD and treated with OHT for 15 days. The DPYD expression level was measured by qPCR, and the percentage of cells remaining in the epithelial state was determined by FACS analysis using CD24 and CD44 as markers to separate the epithelial and mesenchymal populations.

(B) DPYD hairpins strongly reduce DPYD expression. HMLE-Twist-ER cells were infected with the indicated hairpins and DPYD expression levels were measured by qPCR.

(C) DPYD knockdown does not affect proliferation. HMLE cells were infected with the indicated hairpins and the proliferation rate was measured using CellTiterGlo. The number of cells at each time point is represented by relative light units (RLU)(Y-axis), by days (X-axis).

(D) DPYD knockdown reduces ZEB1 expression level. HMLE-Twist-ER cells were infected with the indicated hairpins and left untreated or treated with OHT. The cells were treated with OHT for 15 days and the ZEB1 expression level was measured using qPCR (E) Sequence alignment between human and mouse DPYD in the region of the human gene targeted by shDPYD 1. The sequences, from top to bottom, correspond to SEQ ID NOs.: 35 and 36.

Figure 16:
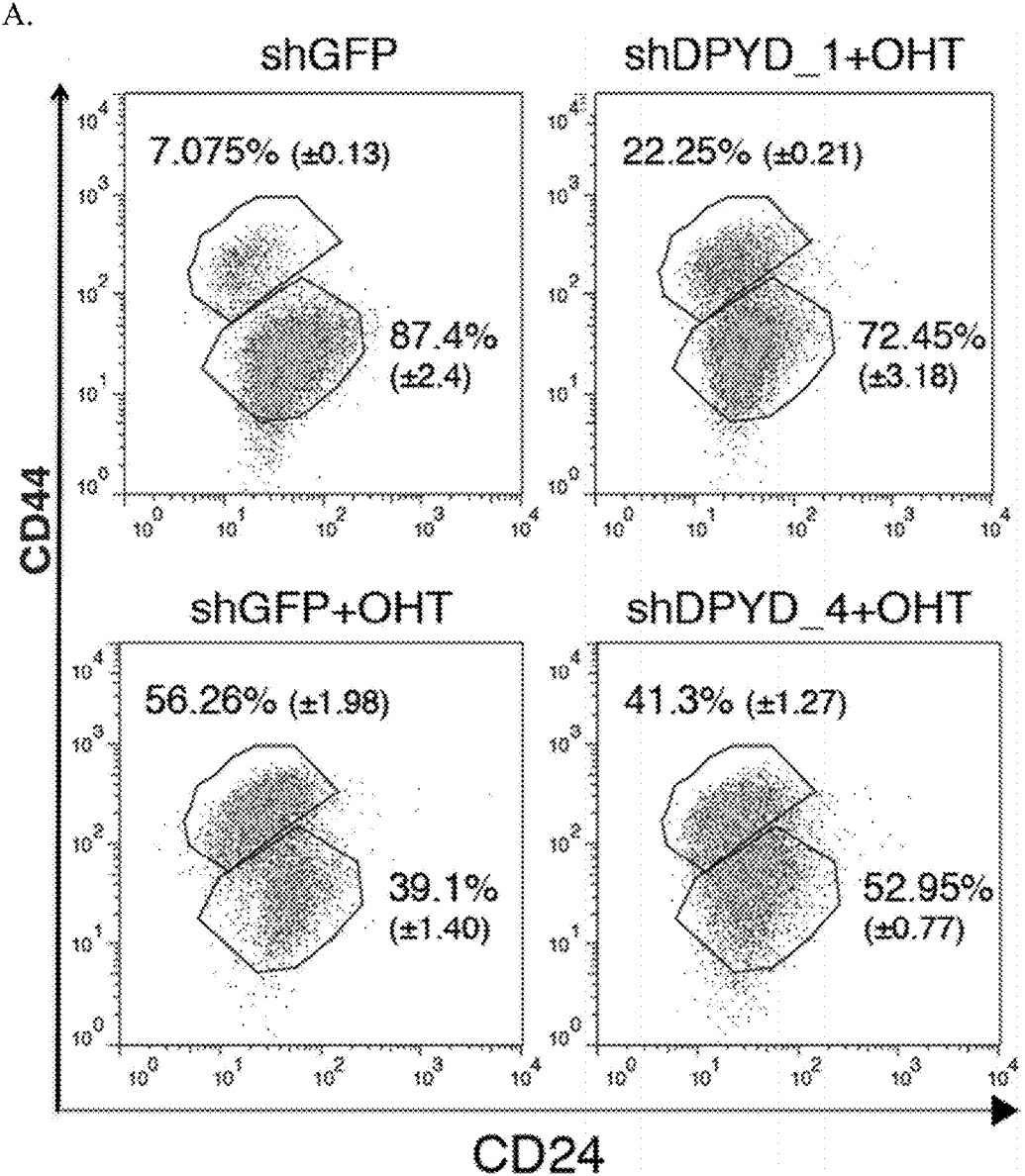
Figure 16:
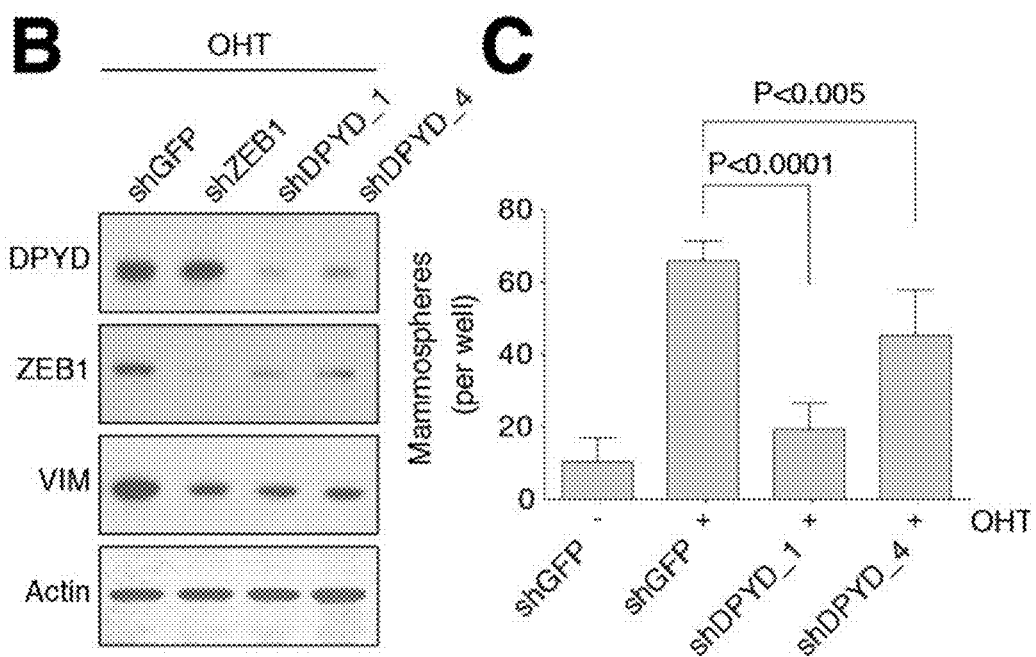
Figure 16:
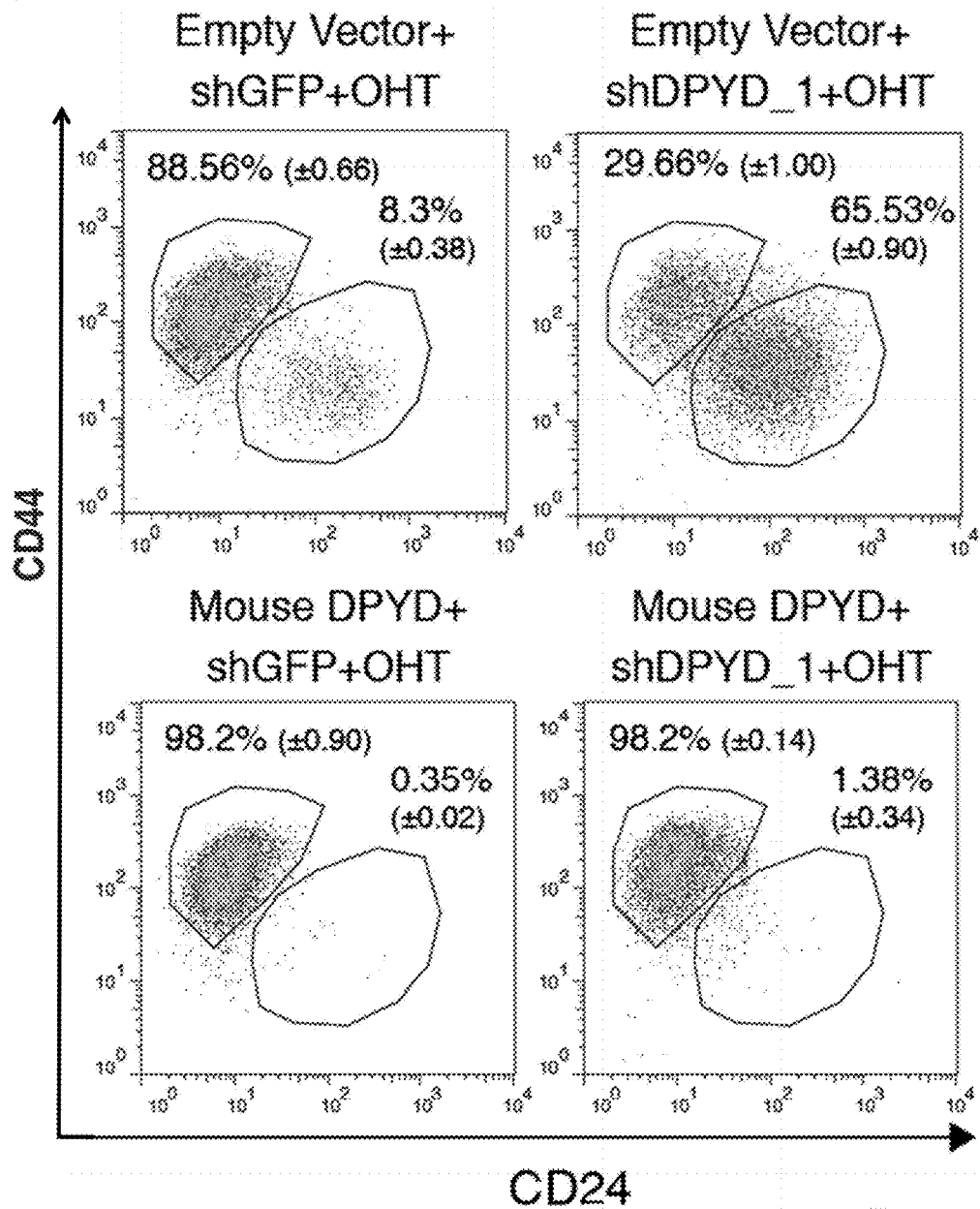
Figure 16:
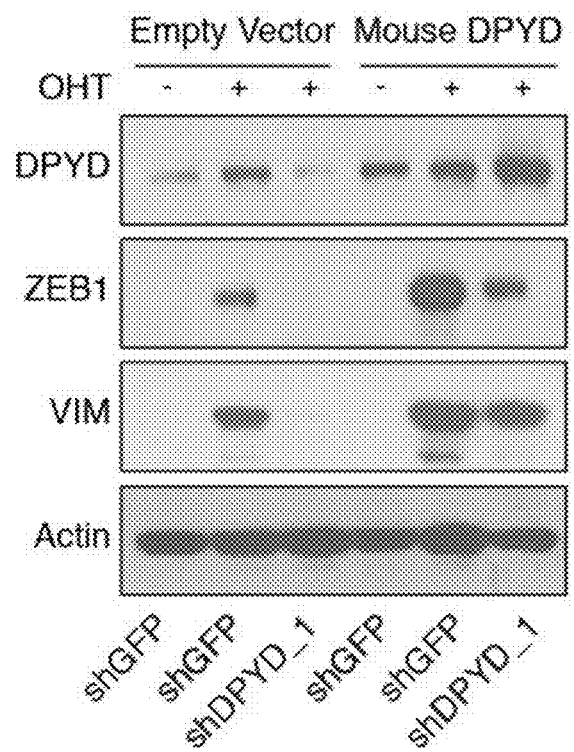
Figure 16:
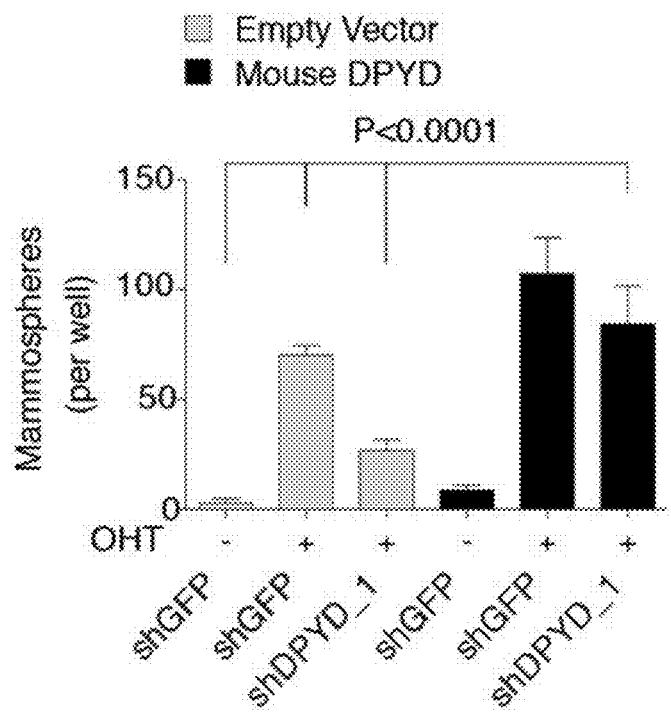

FIG. 16: DPYD expression (A) DPYD knockdown (KD) inhibits the EMT. HMLE-Twist-ER cells were infected with hairpins against GFP (shGFP) and DPYD (shDPYD_1, shDPYD_4). The cells were either left untreated or treated with OHT for 15 days, as indicated, followed by FACS analysis of the cell-surface markers CD24 and CD44 to separate the epithelial and mesenchymal populations. The percentage of cells in each gate is presented.

(B) DPYD KD down-regulates ZEB1 expression. Cells infected with the indicated hairpins were treated with OHT for 15 days and subjected to immunoblotting with the corresponding antibodies.

(C) Quantification of in vitro mammosphere formation by cells treated as in (A). The data are reported as the number of mammospheres formed per 500 seeded cells; each value represents the mean±SD for n=6. The P values for the indicated comparisons were determined using Student's T test.

(D) Mouse DPYD expression rescues the effects of DPYD KD on the EMT. HMLE-Twist-ER cells were infected with virus not expressing a cDNA (empty vector) or expressing mouse DPYD (mDPYD), together with either shGFP or shDPYD_1. The cells were either left untreated or treated with OHT for 15 days, as indicated, followed by FACS analysis of the cell-surface markers CD24 and CD44. The percentage of cells in each gate is presented.

(E) Mouse DPYD rescues the effects of DPYD KD on ZEB1 expression. HMLE-Twist-ER cells infected with the indicated hairpins and vectors were either left untreated or treated with OHT, followed by immunoblotting with the indicated antibodies.

(F) Mouse DPYD rescues the effects of DPYD KD on mammosphere formation. Quantification of in vitro mammosphere formation by cells treated as in (D). The data are reported as the number of mammospheres formed per 500 seeded cells; each value represents the mean±SD for n=6. The P value measured between the indicated samples was quantified using Student's T test.

Figure 17:
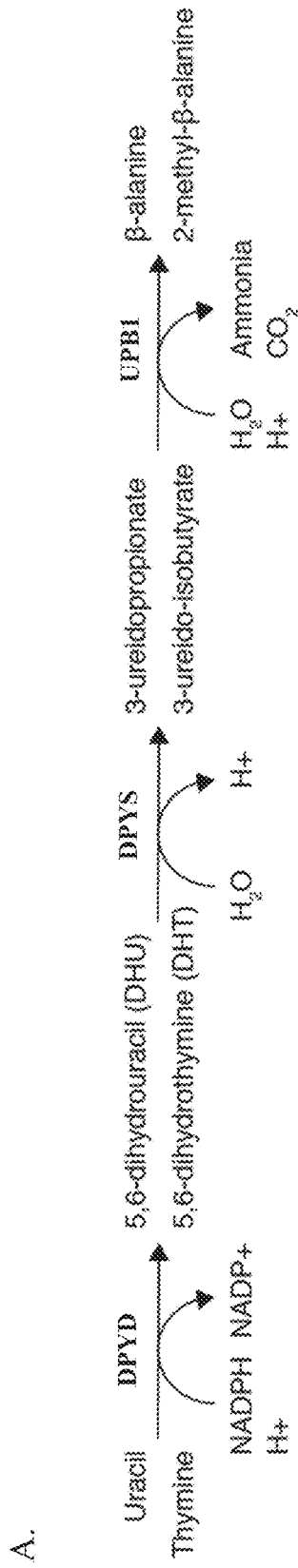
Figure 17:
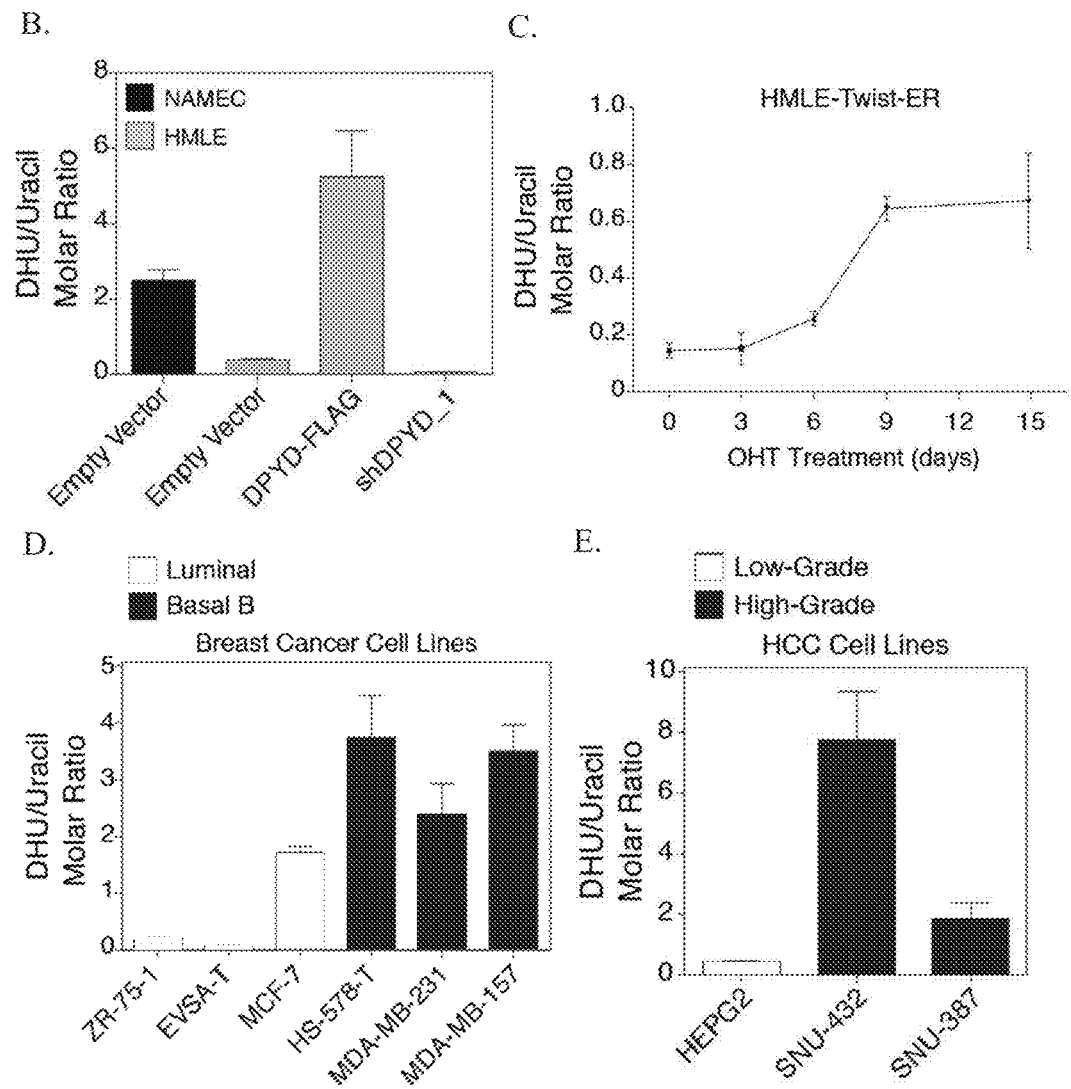

FIG. 17: The products of DPYD are elevated in mesenchymal cells (A) Schematic presentation of the pyrimidine degradation pathway. Gene names are marked in bold: DPYD, dihydropyrimidine dehydrogenase (rate-limiting step); DPYS, dihydropyrimidinase; UPB1, beta-ureidopropionase. Metabolites: DHU, dihydrouracil; DHT, dihydrothymine.

(B) Modulation of DPYD expression affects the cellular DHU/uracil molar ratio. DHU and uracil levels were measured by liquid chromatography and mass spectrometry (LC-MS) in NAMEC or HMLE-Twist-ER cell lines expressing empty vector, DPYD-FLAG or shDPYD_1 hairpin. Each value represents the mean±SD for n=3.

(C) The cellular DHU/uracil ratio increases during EMT. HMLE-Twist-ER cells were treated with OHT for 15 days. At the indicated time points, samples were collected and subjected to LC-MS analysis to determine DHU and uracil levels. The molar concentration ratio between the two metabolites in each sample is presented. Each value represents the mean±SD for n=3.

(D) The cellular DHU/uracil ratio is elevated in Basal B relative to luminal breast cancer cell lines. The abundance of DHU and uracil was measured in the indicated breast cancer cell lines (white, luminal; black basal B) using LC-MS. Each value represents the mean±SD for n=3.

(E) The cellular DHU/uracil ratio is elevated in high-grade relative to low-grade HCC cell lines. Same as (D), but for HCC cell lines (white, low-grade; black, high-grade). Each value represents the mean±SD for n=3.

Figure 18:
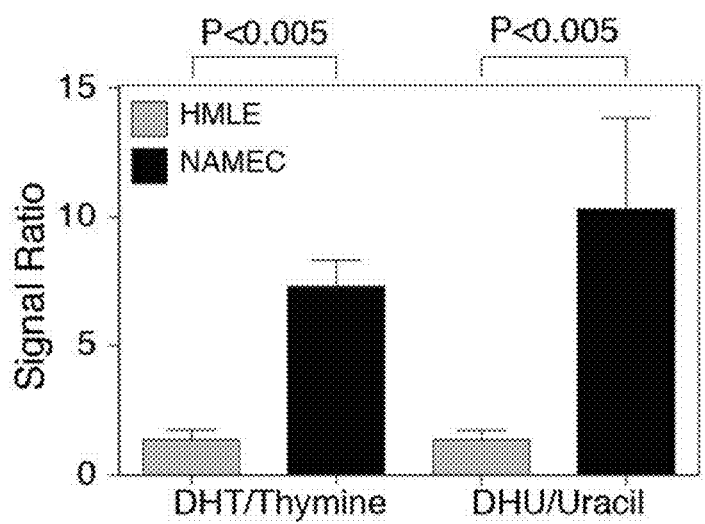
Figure 18:
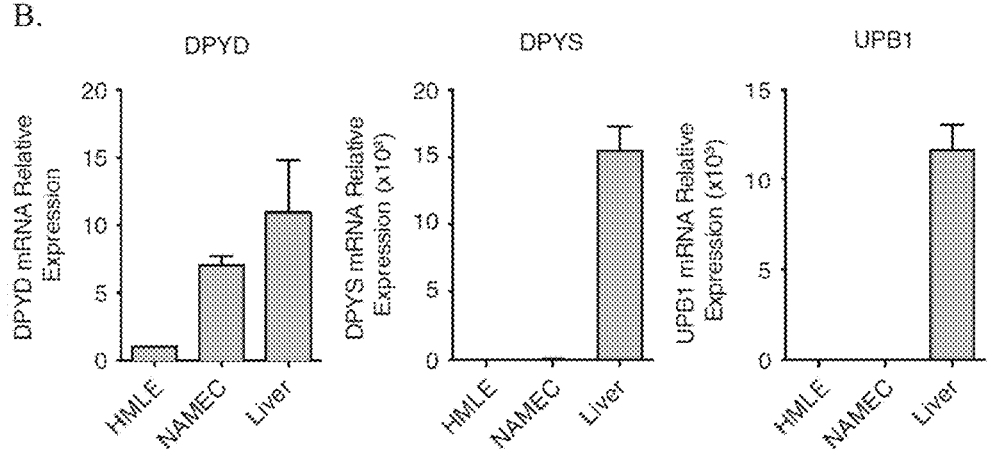
Figure 18:
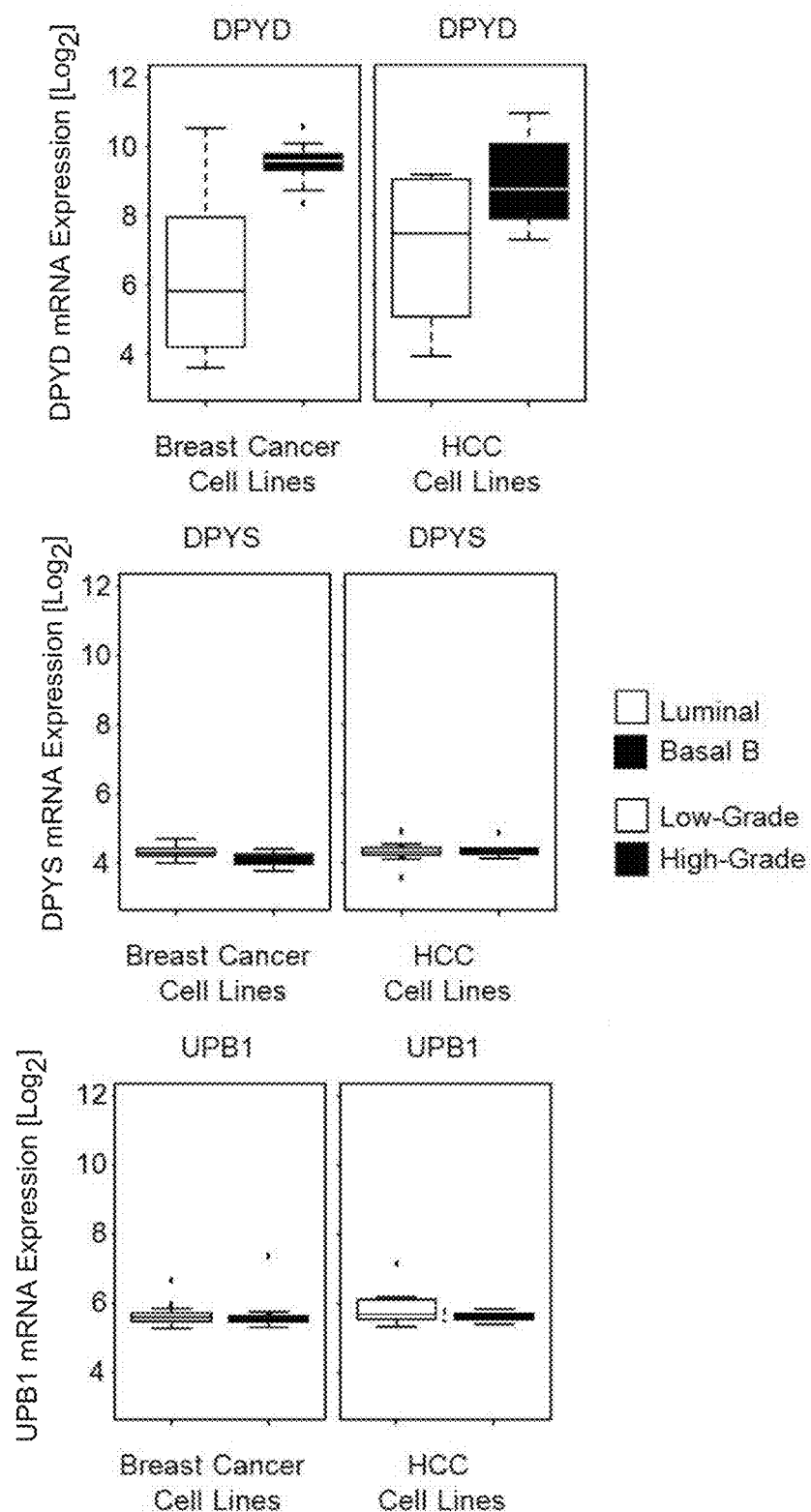

FIG. 18: DPYD products are elevated in mesenchymal cells (A) NAMEC cells contain a higher ratio of the DPYD products dihydrothymine (DHT) and dihydrouracil (DHU) to the corresponding substrates, thymine and uracil, as compared to uninduced HMLE-Twist-ER cells. The abundance of all four metabolites was measured by LC-MS in uninduced HMLE-Twist-ER (HMLE, gray) and NAMEC (black) cells. The bars represent the ratio between the two indicated metabolites in each cell line. Each value represents the mean±SD for n=3. The P values for the indicated comparisons were determined using Student's T test. Each value represents the mean±SD for n=3. The P values for the indicated comparisons were determined using Student's T test.

(B) DPYD is the only pyrimidine degradation pathway enzyme expressed in HMLE-Twist-ER and NAMEC cell lines. The mRNA from HMLE-Twist-ER cells, NAMEC cells, and human liver was isolated and subjected to qPCR to determine the relative expression of DPYD, DPYS and UPB1. Each value represents the mean±SEM for n=3.

(C) Expression of DPYD, but not of the other pyrimidine degradation pathway genes, is elevated in Basal B breast and high-grade HCC cancer cell lines. Box plots represent the expression levels of DPYD, DPYS and UPB1 (as indicated) in breast cancer (white, luminal; black, Basal B) and HCC (white, low-grade; black, high-grade) subtypes.

Figure 19:
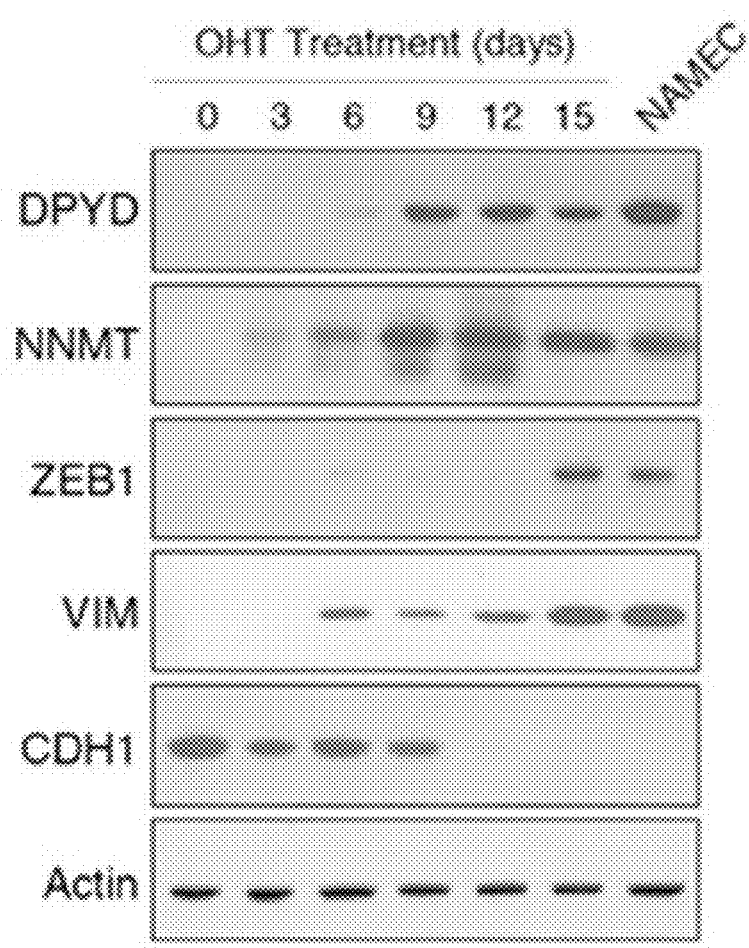
Figure 19:
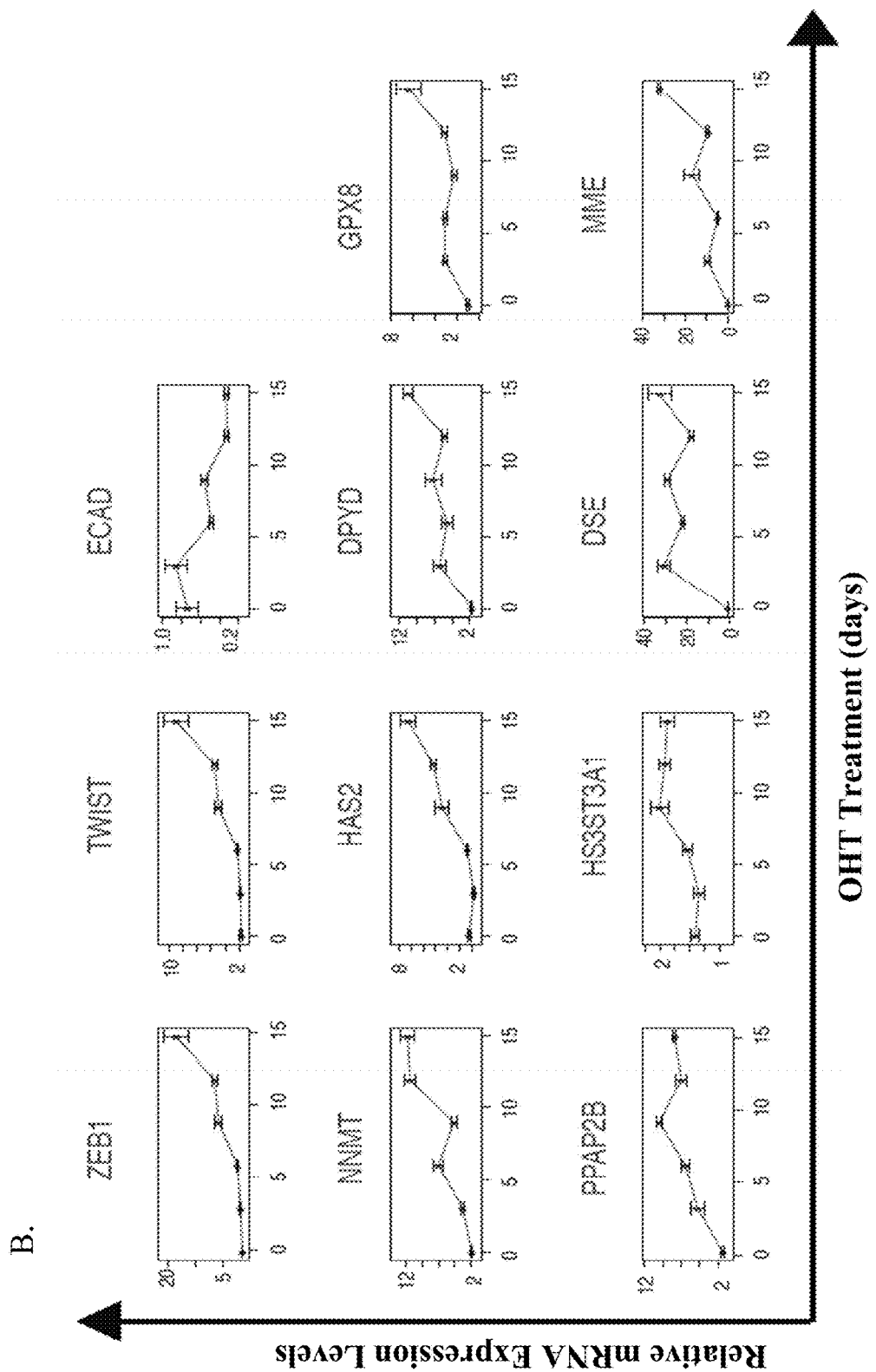
Figure 19:
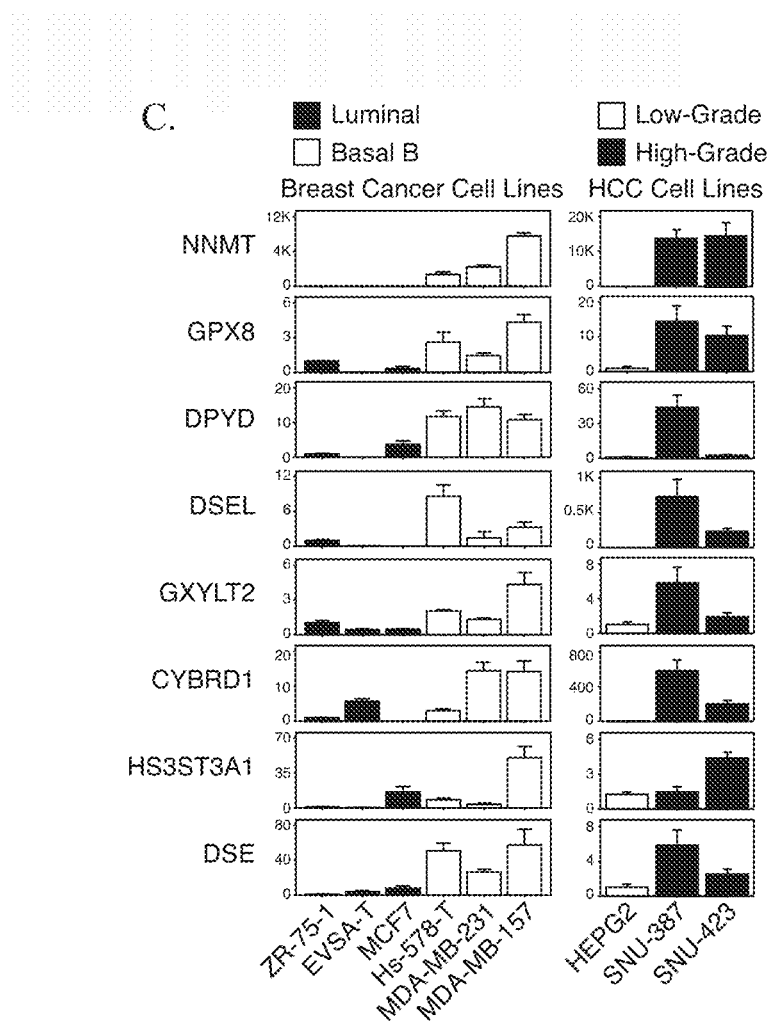

FIG. 19: High expression of mesenchymal metabolic signature (MMS) genes in mesenchymal cell lines (A) MMS protein upregulation in the same cells as in (G). Every three days, cellular proteins were isolated and subjected to immunoblotting using the indicated antibodies. NAMEC cells are mesenchymal cells derived from HMLE cells (see methods).

(B) MMS gene upregulation in an HMLE-Twist-ER inducible EMT system. HMLE-Twist-ER cells were treated with hydroxytamoxifen (OHT) to induce an EMT for 15 days. Every three days, cells were collected and mRNA isolated and subjected to qPCR using the indicated probes. Each value represents the mean±SEM for n=3.

(C) Individual validation of MMS mRNA levels in breast cancer (black, luminal; white, Basal B) and HCC (white, low-grade; black, high-grade) cell lines by quantitative real-time PCR (qPCR). Each value represents the mean±SEM for n=3.

Figure 20:
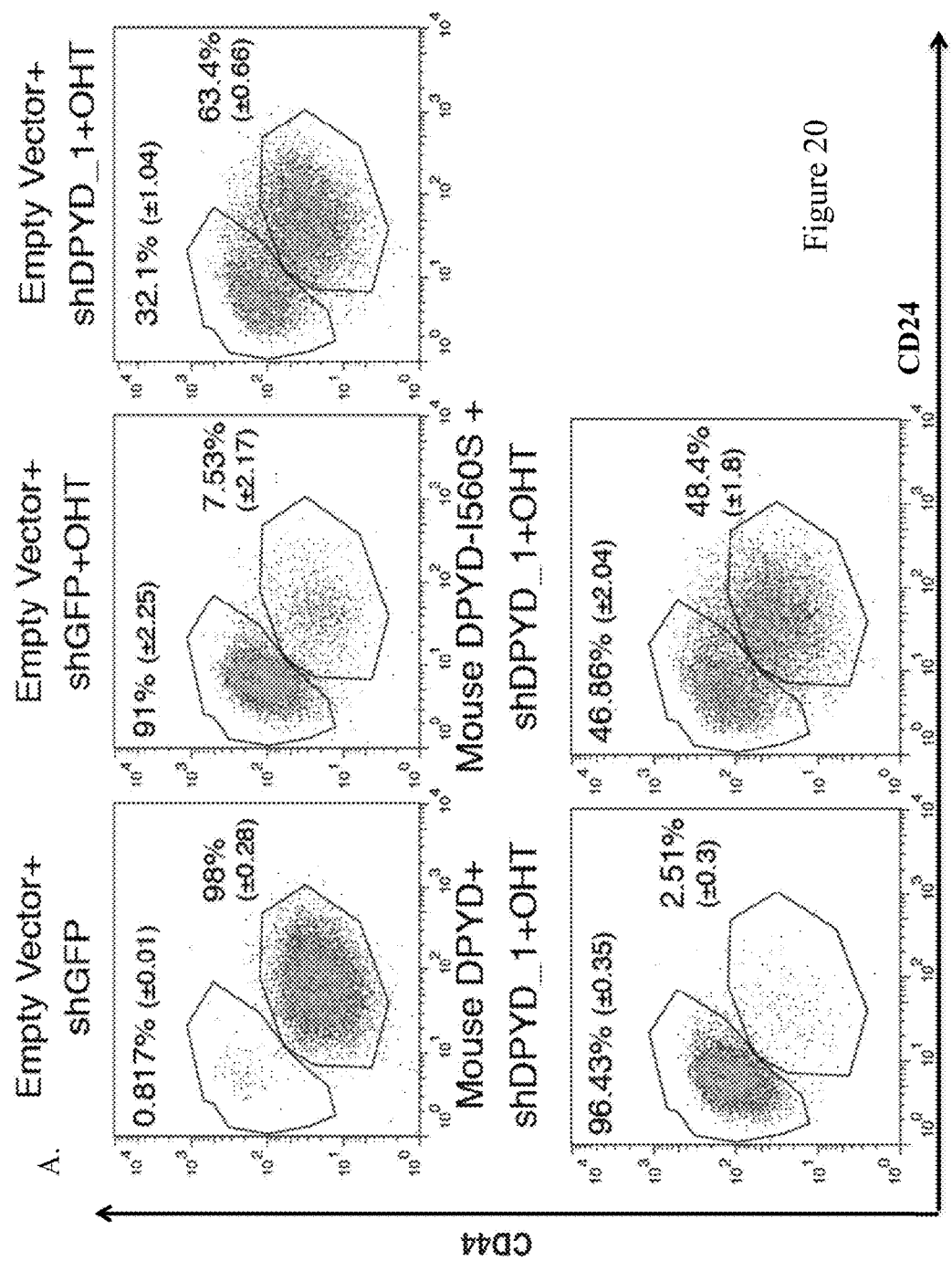
Figure 20:
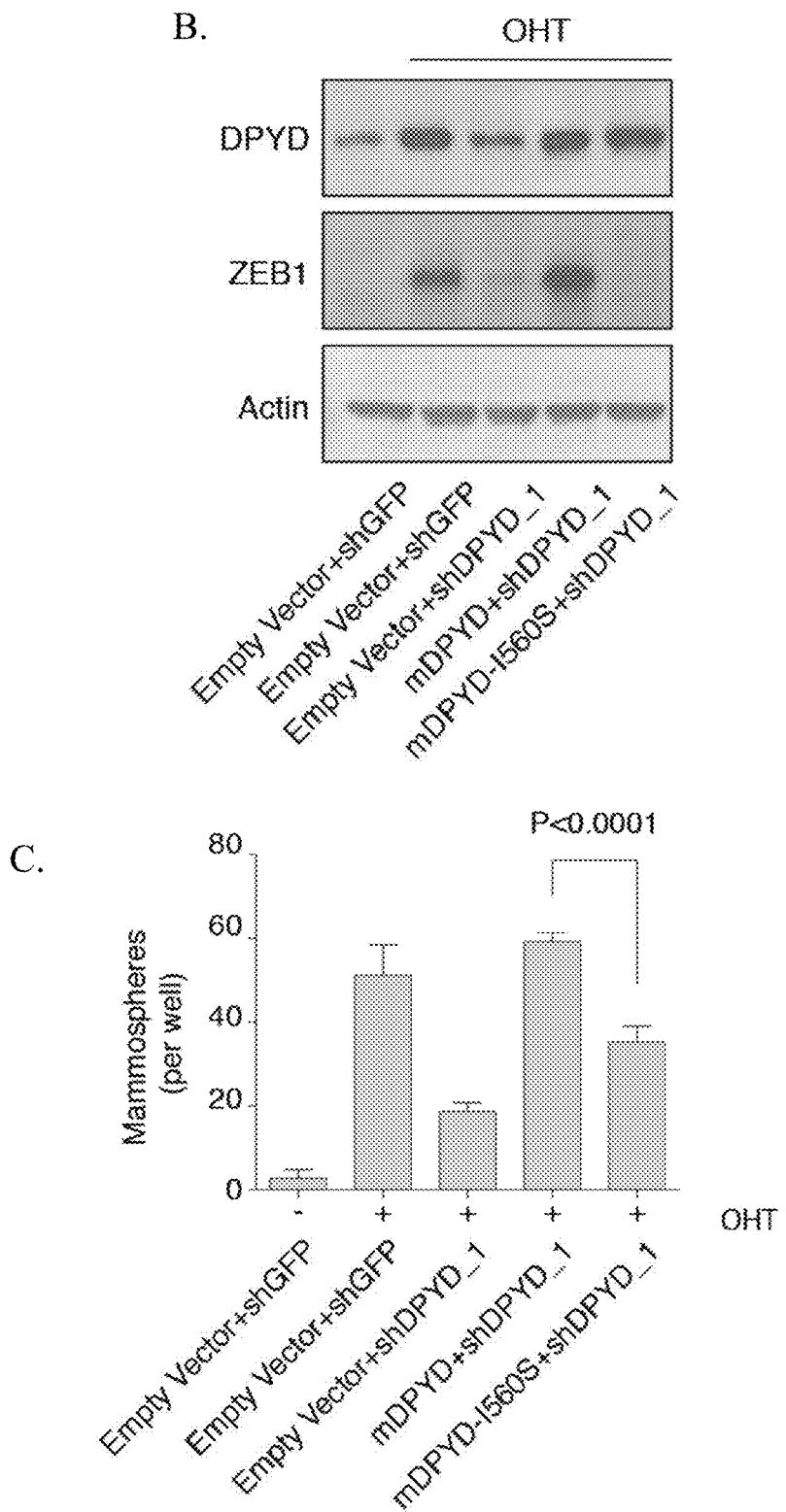
Figure 20:
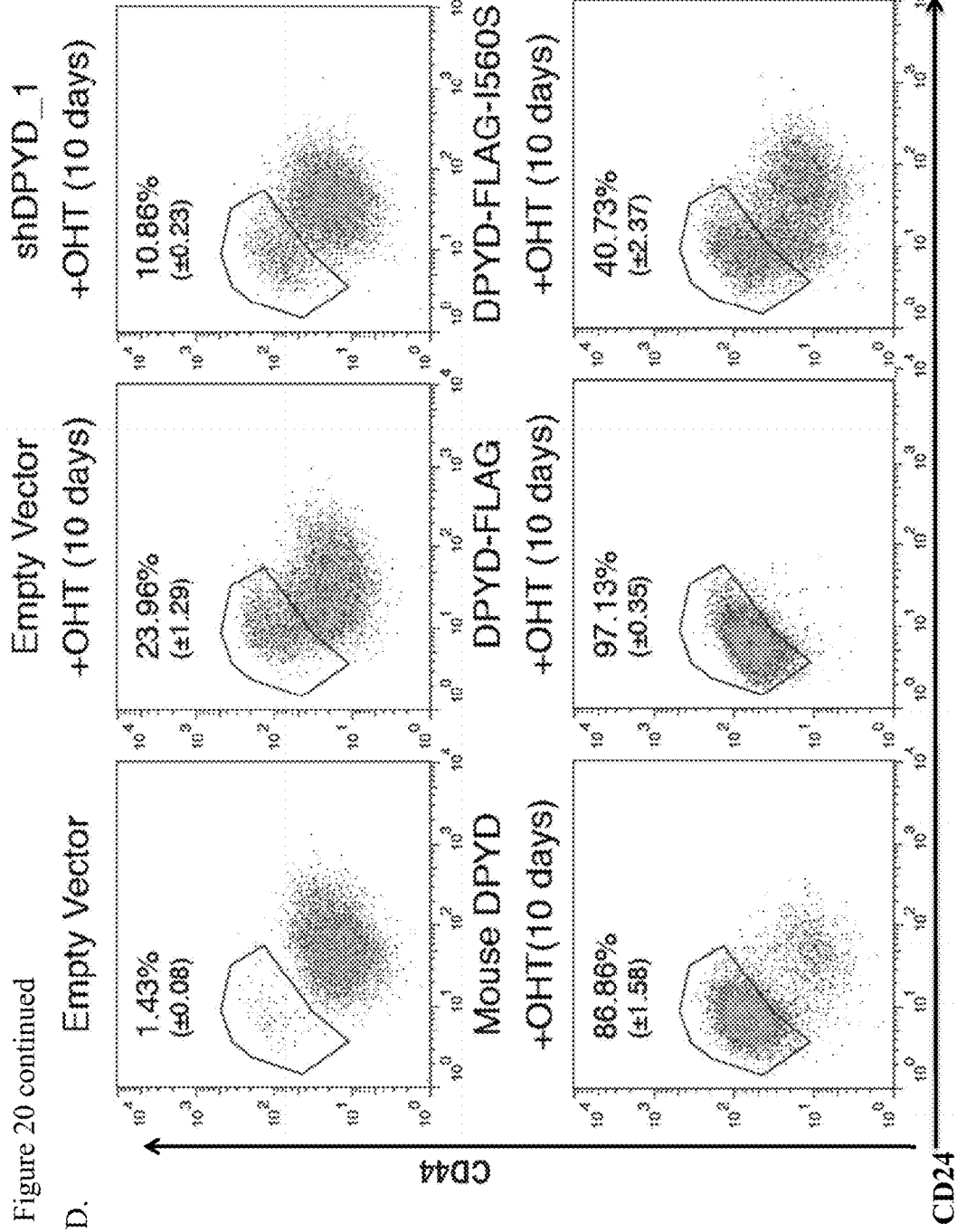
Figure 20:
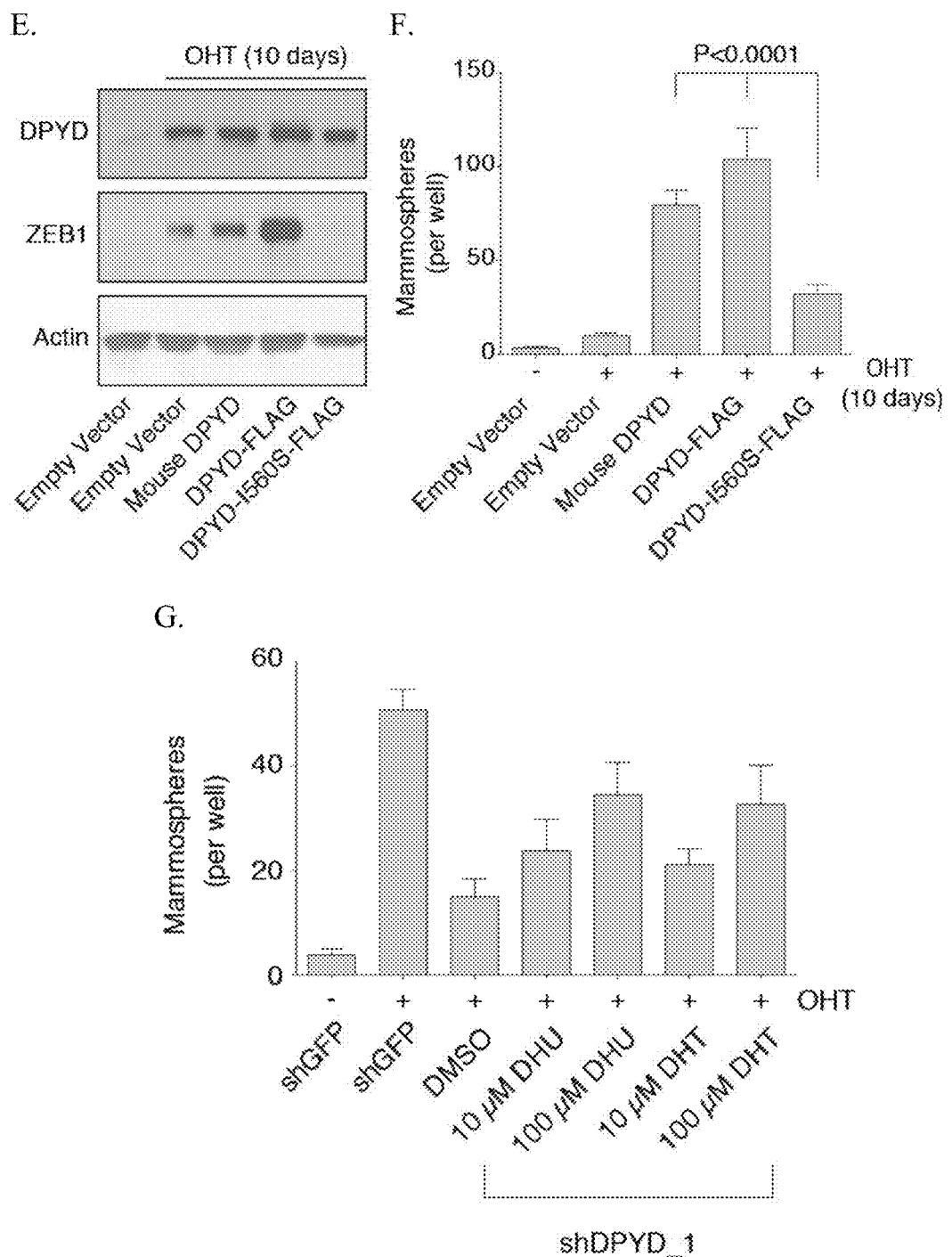

FIG. 20: DPYD enzymatic activity (A) Mouse DPYD-I560S fails to rescue the effect of DPYD knockdown (KD) on the EMT. HMLE-Twist-ER cells were infected with empty vector, mouse DPYD (mD-PYD) or partially active mouse DPYD (DPYD-I560S), together with either shGFP or shDPYD 1. The cells were treated with OHT for 15 days, as indicated, followed by FACS analysis as in FIG. 16A.

(B) Mouse DPYD-I560S fails to rescue the effects of DPYD KD on ZEB1 expression. HMLE-Twist-ER cells infected with the indicated hairpins and vectors were either left untreated or treated with OHT, followed by immunoblotting with the indicated antibodies.

(C) Mouse DPYD-I560S fails to rescue the effects of DPYD KD on mammosphere formation. Cells treated as in (B) were subjected to the in vitro mammosphere formation assay as in FIG. 16C.

(D) DPYD activity accelerates the EMT. HMLE-Twist-ER cells expressing shDPYD 1, human DPYD (DPYD-FLAG), mouse DPYD, or partially active human DPYD-FLAG-I560S were either left untreated or treated with OHT for 10 days, followed by FACS analysis as in FIG. 16A. The percentage of cells in each gate is presented.

(E) Expression of catalytically attenuated DPYD reduces ZEB1 expression. Cells infected with the indicated constructs were either left untreated or treated with OHT for 10 days, followed by immunoblotting with the indicated antibodies.

(F) DPYD activity enhances mammosphere formation. Cells treated as in (D) were subjected to the in vitro mammosphere formation assay as in FIG. 16C.

(G) DPYD products rescue the effect of DPYD KD on mammosphere formation. HMLE-Twist-ER cells expressing shDPYD_1 were treated with the indicated concentrations of dihydrouracil (DHU) or dihydrothymine (DHT) and subjected to the in vitro mammosphere formation assay as in FIG. 16C.

Figure 21:
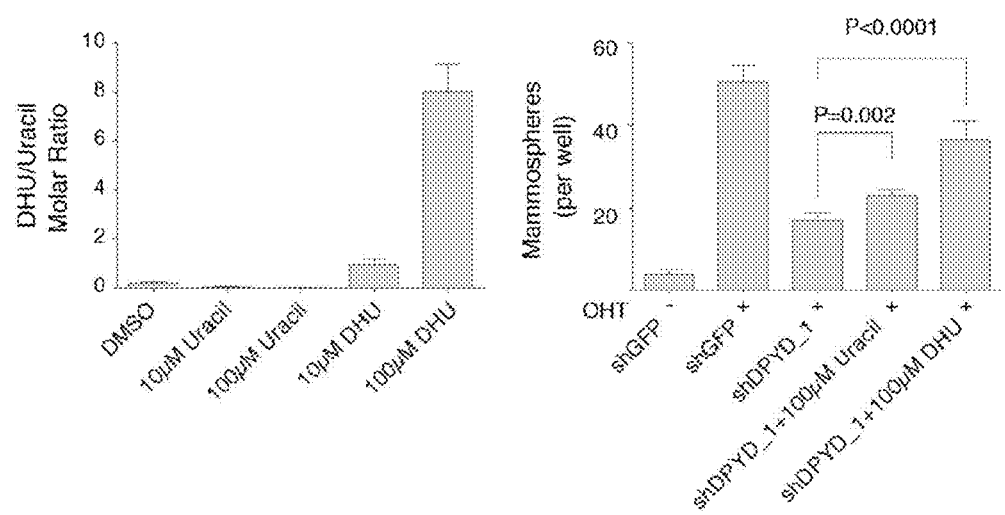

FIG. 21: DPYD activity

DHU rescues the effect of DPYD KD on mammosphere formation more strongly than uracil. HMLE-Twist-ER cells expressing shDPYD_1 where either left untreated or induced with OHT with or without the addition of uracil or dihydrouracil, as indicated. The mammosphere data (right panel) are reported as the number of mammospheres formed per 500 seeded cells; each value represents the mean±SD for n=6. The P value for the indicated comparison was determined using Student's T test.

BRIEF DESCRIPTION OF ELECTRONICALLY FILED TABLES

The following tables were submitted electronically with U.S. Provisional Application Ser. No. 61/768,922, filed on Feb. 25, 2013, entitled "METABOLIC GENE MESENCHYMAL SIGNATURES AND USES THEREOF." The contents of these tables are incorporated herein by reference in their entireties:

E1_MGMS_gene_information.txt; 36.0 kb; date created Feb. 25, 2013; Table with annotation information about MGMS genes.

E2_universalgenes_top_bottom_genes_summary.txt; 24.0 kb; date created Feb. 25, 2013; Table with additional information about universal genes. Top and bottom designations refer to whether the gene is overexpressed (top) or underexpressed (bottom) in cancers.

E3_universalgene_list.txt; 86.0 kb; date created Feb. 25, 2013; Table with additional information about universal genes, including gene IDs (from NCBI Gene database) and Unigene IDs.

E4_high_grade_top_bottomgenes_over 2.5.txt, 8.0 kb; date created Feb. 25, 2013; Table with additional information about the MGMS genes with Z-scores over 2.5. Among other things, it includes the rank by Z-score of the MGMS genes, and various compounds that inhibit gene products of certain of the MGMS genes.

E5_high_grade_top_bottomgenes.txt, 8.0 kb; date created Feb. 25, 2013; Table with additional information about the MGMS genes. Among other things, it includes the rank by Z-score of the MGMS genes, and various compounds that inhibit gene products of certain of the MGMS genes.

DETAILED DESCRIPTION OF INVENTION

Aspects of the invention relate to methods and compositions for characterizing or modulating the expression of human genes involved in various metabolic pathways. Many chemotherapeutic drugs are designed to inhibit metabolic enzymes related to cellular proliferation. Even though many of these anti-metabolites are efficient in inhibiting cellular growth, they often lack specificity. Here, by analyzing changes in metabolic gene expression in a variety of cancerous cells, we aimed to identify metabolic processes important for cancer development. To this end, we assembled ~4,500 gene expression arrays, and generated "MERAV", a tool providing normalized expression of ~1,700 metabolic genes in human normal tissues, cancer cell lines, and primary tumors. We found that while normal cells express tissue-specific metabolic gene expression pattern, tumors lose this specificity, suggesting on a malignant remodeling that affects a variety of tissue specific cellular processes. Interestingly, most cancer cell lines cluster together based on their tissue of origin, with the exception of several high-grade carcinomas that cluster with mesenchymal-derived cell lines. Within the mesenchymal cluster, we identified a set of metabolic genes that includes many enzymes important for extracellular matrix synthesis. Moreover, we found that this set of genes correlates with the epithelial to mesenchymal transition (EMT). Finally, we verified the physiological relevance of these genes by applying a FACS-based functional pool analysis approach, and demonstrated that indeed the knockdown of these genes significantly inhibited EMT. In conclusion, we demonstrated a cancer-dependent remodeling of metabolic gene expression, affecting a variety of cancer-dependent processes such as EMT.

Thus, in some embodiments, it has been found that certain cancer cell lines demonstrate a gene signature based on the expression of human genes involved in metabolic pathways. In some embodiments, it has been found that cancer cell lines derived from a common tissue of origin (e.g., neuroectodermal; mesenchymal) generally cluster together based on their metabolic gene expression profile. In some embodiments, cancer cell lines of non-mesenchymal origin (non-mesenchymally derived), including a number of cancer cell lines derived from a variety of carcinomas as well as from glioblastomas, display a metabolic gene signature characteristic of cancer cell lines of mesenchymal origin (mesenchymally derived cancer cell lines). Thus, in some embodiments, non-mesenchymally derived cancer cell lines that exhibit a mesenchymal phenotype are identified based solely on their metabolic gene expression profile.

Metabolic Gene Mesenchymal Signature

In some embodiments, a set of metabolic genes that exhibit different expression levels in mesenchymally derived cancer cell lines versus non-mesenchymally derived cancer cell lines is provided. In some embodiments, the metabolic genes are those outlined in Table 2. In some embodiments, these genes are referred to as "metabolic mesenchymal genes." In some embodiments, the expression levels of one or more metabolic mesenchymal genes may referred to as a "metabolic gene mesenchymal signature" (MGMS). In some embodiments, this signature may alternatively be referred to as a "metabolic mesenchymal signature".

In some embodiments, analysis of expression or activity of MGMS genes in cancers may be used for a variety of purposes, e.g., in cancer classification, prognosis, diagnosis, or treatment selection. For example, carcinomas that exhibit a MGMS gene expression profile (e.g., carcinomas that cluster with mesenchymal cancer cell lines based on their metabolic gene expression profile) may be more aggressive, associated with a worse prognosis, have an increased likelihood of having metastasized or being prone to metastasize, and/or be characterized by increased cancer stem cell (CSC) formation and/or increased CSC content, as compared with carcinomas that do not exhibit an MGMS gene expression profile. Analysis of the expression or activity of MGMS genes may be used to identify cancer patients (e.g., patients with carcinomas or other cancers) who may benefit from intensive and/or prolonged monitoring for recurrence or metastasis and/or who may benefit from intensive and/or prolonged therapy. For example, patients with carcinomas that exhibit a MGMS gene expression profile may be more likely to benefit from intensive and/or prolonged monitoring or therapy than patients with carcinomas that do not exhibit a MGMS gene expression profile.

Analysis of MGMS genes may be used to identify cancers (e.g., carcinomas or other cancers) for which treatment with drugs that act on (kill or inhibit) CSCs, e.g., CSC-selective drugs, may be particularly appropriate. Analysis of MGMS genes may be used to identify patients with cancer (e.g., carcinomas or other cancers) for whom treatment with drugs that act on (kill or inhibit) CSCs, e.g., CSC-selective drugs, may be particularly appropriate.

In some embodiments, a subset of the MGMS genes may be used, e.g., for cancer classification, prognosis, diagnosis, or treatment selection. In some embodiments, a subset of the MGMS genes comprises or consists of one, more than one, or all MGMS-upregulated genes. In some embodiments a subset of the MGMS genes comprises or consists of at least one, more than one, or all MGMS-downregulated genes. In some embodiments a subset of the MGMS genes consists of one, more than one, or all MGMS genes.

Cancer Classification and Assessment

Provided herein, in some embodiments, are methods for evaluating and classifying a cancer of non-mesenchymal origin (e.g., a carcinoma) in a subject. In some embodiments, the methods involve subjecting a sample of a cancer obtained from a subject to a gene expression analysis and comparing the expression levels to reference expression levels of the plurality of metabolic mesenchymal genes in appropriate reference cells (e.g., mesenchymal cells, cancer stem cells, non-mesenchymal cells, epithelial cells). In some embodiments, the results of the methods are indicative of the extent to which cells in the cancer have undergone a epithelial-to-mesenchymal transition. In some embodiments, the results of the methods are indicative of the presence of cancer stem cells in the cancer. In some embodiments, the results of the methods are indicative of the aggressiveness of the cancer.

In some embodiments, methods for diagnosing a subject as having a cancer (e.g., a carcinoma) are provided. The methods typically involve an assessment of the expression of one or more metabolic mesenchymal genes to determine whether the subject has cancer, the origin of the cancer (e.g., epithelial origin), whether and to what extent the cancer has cancer stem cells, and/or whether the cancer is of an aggressive or non-aggressive type. However, the methods may involve a combination of a pathological examination or other methodology and an assessment of expression of one or more metabolic mesenchymal genes. Accordingly, information obtained from a gene expression analysis may be combined with other information to diagnosis the cancer status or prognosis of the subject. For example, information obtained regarding the subject's genetic predisposition towards the cancer, family history, behavioral characteristics, social habits, environmental exposures, tobacco use and/or information from other diagnostic modalities, e.g., pathological and/or imaging methodologies (e.g., X-ray imaging, ultrasound imaging, etc.) may be combined to make a diagnosis or aid in making a diagnosis.

In some embodiments, the methods involve subjecting a tissue sample obtained from a subject to a pathological examination, in which the results of the pathological examination are indicative of whether the tissue sample comprises a carcinoma or other cancer type. In some embodiments, the pathological examination is further indicative of whether the tissue sample comprises cancer stem cells. In some embodiments, the pathological examination comprises performing microscopic examination on cells of the tissue sample, and determining whether the tissue sample comprises a carcinoma or other cancer type and/or whether the tissue sample comprises cancer stem cells. The pathological examination is, in some embodiments, based at least in part on the morphology of the cells or the expression of one or more markers by the cells as determined by a microscopic examination.

In some embodiments, the methods further comprise subjecting the tissue sample to a gene expression analysis to determine expression levels of one or more metabolic mesenchymal genes in the sample. Often, the results of the gene expression analysis and the pathological examination are together indicative of the nature or origin of the cancer and presence or absence of cancer stem cells. Thus, in some embodiments, methods are provided that are useful for diagnosing (or aiding in diagnosing) a subject as having a carcinoma that contains cancer stem cells. The methods are useful in part because they inform a treating health care provider as to whether a subject will be responsive to a particular treatment, e.g., a cancer stem cell specific treatment, or whether the cancer will likely be resistant to certain standard chemotherapeutics or other aspects relating to treating the subject.

In some embodiments, methods are provided for evaluating aggressiveness of a cancer of non-mesenchymal origin in a subject. The methods, in some embodiments, involve subjecting a sample of the cancer obtained from the subject to a gene expression analysis to determine expression levels of one or more metabolic mesenchymal genes in the sample. In such embodiments, the results of the expression analysis are indicative of whether cancer is aggressive or non-aggressive. Thus, in some embodiments, the methods establish whether the subject has an aggressive or non-aggressive cancer of non-mesenchymal origin. It will be appreciated that an aggressive cancer is a cancer associated with a poor prognosis; a highly malignant cancer; a cancer containing cancer stem cells; a cancer enriched for cancer stem cells; a cancer that is resistant to one or more chemotherapeutic agents; and/or a cancer that has metastasized or is prone to metastasize.

In some embodiments, methods for assessing non-mesenchymally derived cancer cells are provided. In some embodiments, the methods involve subjecting non-mesenchymally derived cancer cells to a gene expression analysis to determine expression levels of one or more metabolic mesenchymal genes in the non-mesenchymally derived cancer cells and comparing the expression levels to reference expression levels of the plurality of metabolic mesenchymal genes in appropriate reference cells. In such embodiments, the results of the comparison are indicative of the extent to which the non-mesenchymally derived cancer cells have undergone a epithelial-to-mesenchymal transition.

In some embodiments, methods for assessing or identifying the tissue of origin of cancer cells are provided. In some embodiments, the methods involve subjecting cancer cells to a gene expression analysis to determine expression levels of one or more metabolic mesenchymal genes in the cancer cells and determining the tissue of origin of the cancer cells based on the expression levels of the plurality of metabolic mesenchymal genes.

In the context of the foregoing classification, assessment, and/or diagnostic methods, the metabolic mesenchymal genes may be selected from Table 2. In some embodiments, the metabolic mesenchymal genes are selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. In some embodiments, the metabolic mesenchymal genes are selected from: QPRT, CYBA, PTER, MFNG, TM7SF2, PLCG2, ST6GAL1, CA2, GLB1L2, PIK3C2B, GCH1, ALDH1A1, GPX2, and GALNT3.

In some embodiments, the product of the metabolic mesenchymal genes function in a pathway selected from: a sulfatase pathway, heparan sulfate biosynthesis pathway, nicotine degradation pathway, prostaglandin pathway, methionine pathway, branched-chain-amino-acid aminotransferase, pathway, glycan pathway, monoxygenase pathway, peptidylamidoglycan pathway, melatonin degradation pathway, phosphatidate phosphatase pathway, hyaluronan synthase pathway, nitric oxide pathway, extracellular sulfatase pathway, dermatan sulfate biosynthesis pathway, phosphodiesterase pathway, neprilysin pathway, glutathione pathway, lipid phosphate phosphohydrolase pathway, glycogen biosynthesis pathway, cytochrome c pathway, UDP-N-acetyl-D-glucosamine biosynthesis pathway, glucosylceramide synthasis pathway, nucleotide pathway, triacylglycerol degradation pathway, amino sugar pathway, sphingosine kinase 1 pathway, carbonic acid pathway, UDP pathway, adenylate kinase pathway, aldoketoreductase pathway, NAD pathway, cytochrome pathway, cholesterol biosynthesis pathway, phospholipase pathway, Beta-galactoside pathway, lactose degradation pathway, tetrahydrobiopterin biosynthesis pathway, retinoate biosynthesis pathway, glutathione peroxidase pathway, and O-glycan pathway.

It should be appreciated that the methods may involve obtaining a tissue sample from a region of a subject suspected of containing the cancer. The tissue sample may be obtained directly, e.g., by excising the tissue sample from the subject. The tissue sample may also be obtained indirectly, e.g., by receiving the tissue sample (e.g., by mail or courier) from a clinician who obtained the sample directly from the subject.

Modulation of MGMS Genes

Modulation of the expression or activity of MGMS genes (e.g., MGMS-EMT genes) or their gene products or modulation of expression or activity of genes or gene products that function in the same metabolic pathways may be used to modulate an epithelial to mesenchymal transition. Methods of modulating MGMS described herein are generally suitable or adaptable for both in vitro and in vivo (e.g., in the context of a treatment for cancer) applications. As used herein, an "epithelial to mesenchymal transition" (EMT) refers to a transformation, or partial transformation, of an epithelial cell into a cell having one or more mesenchymal characteristics that also has one or more properties of a cancer or non-cancer stem cell. The one or more cancer or non-cancer stem cell properties may include the presence or absence (high expression levels or low expression levels) of one or more proteins (e.g., cell surface markers) and/or an increase in one or more (at least 2, at least 3, at least 4, at least 5, at least 6) functional properties including the ability to grow (proliferate) in suspension cultures, ability to form tumors in vivo at low cell seeding numbers, resistance to certain chemotherapies (e.g., resistance to paclitaxel), metastatic ability, migration ability, resistance to apoptosis or anoikis, scattering, and elongation of cell shape. It is to be understood that the extent to which a cell that has undergone an EMT exhibits an increase or decrease in the expression of one or more proteins or an increase in one or more functional properties of a cancer stem cell may be assessed by performing a comparison with a control cell, e.g., a cell that has not undergone an EMT (a negative control cell) or a cell that has undergone an EMT (a positive control cell), e.g., a cancer stem cell.

As described herein, inhibition of MGMS-EMT gene expression inhibits EMT. MGMS-EMT genes and their gene products (and genes and gene products that function in the same metabolic pathways) are of interest as targets for identification, development, selection, or use of agents (e.g., small molecules, peptides, RNAi agents aptamers) useful to inhibit EMT, e.g., in cancer or other conditions associated with pathological EMT, and/or useful to inhibit CSC formation. MGMS-EMT genes and their gene products may be attractive targets for treatment of cancer at least in part because EMT in epithelial-derived cancers can give rise to cancer cells with properties of cancer stem cells and is associated with chemoresistance and with metastasis (which is responsible for most cancer-related mortality). Loss of expression or activity of MGMS-EMT genes and gene products may have little or no effect on cell proliferation, as demonstrated for DPYD. Thus inhibiting these genes or their gene products may be associated with reduced severity or reduced likelihood of typical side effects that occur with cancer chemotherapeutic agents that non-selectively target proliferating cells, as compared with cancer chemotherapeutic agents that non-selectively target proliferating cells. Certain metabolic genes that are not part of the MGMS identified here but that are important for EMT may also be similarly useful (such as ELOVL5 and HNMT, which were identified in the shRNA screen from among the 16 randomly selected metabolic genes that were tested).

In some embodiments an agent that inhibits expression or activity of a MGMS-EMT gene or gene product is used to treat an individual at risk of or suffering from a mesenchymally derived cancer. In some embodiments an agent that inhibits expression or activity of a MGMS-EMT gene or gene product is used to treat an individual at risk of or suffering from a non-mesenchymally derived cancer that exhibits an MGMS gene expression profile. In some embodiments an agent that inhibits expression or activity of a MGMS-EMT gene or gene product is used to treat an individual at risk of or suffering from a CSC-enriched or CSC-dependent cancer.

Enhancing the expression or activity of MGMS-upregulated genes (e.g., MGMS-EMT genes) or their gene products (or other genes/gene products that function in the same metabolic pathway) in epithelial cells and/or reducing the expression or activity of MGMS-downregulated genes or their gene products (or other genes/gene products that function in the same metabolic pathway) in epithelial cells may be useful to promote EMT, e.g., for purposes of generating cells with characteristics of stem cells. In some embodiments such stem cells are generated (e.g., in vitro) from cancer cells, e.g., carcinoma cells. In some embodiments such cells have properties of CSCs. Cells with properties of CSCs may be useful for a variety of purposes. For example, such cells may be useful to study CSC biology, to identify agents that inhibit (e.g., selectively inhibit) CSCs, etc.

In some embodiments cells with properties of stem cells may be generated (e.g., in vitro) from normal, non-cancer cells. Such cells or their differentiated progeny may be useful in cell therapy, e.g., in regenerative medicine.

In some embodiments, cells with properties of stem cells are generated from normal, non-cancer cells by forcing expression in the normal, non-cancer cells of a metabolic mesenchymal gene the product of which induces an epithelial to mesenchymal transition in the cells. Accordingly, in some embodiments, stem cells may be generated by forcing expression in a cell of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1.

Forced expression of the metabolic mesenchymal gene may be accomplished by delivering to a cell a nucleic acid engineered to express the metabolic mesenchymal gene in the cell. The nucleic acid may be delivered via an appropriate vector. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes or portions thereof.

An expression vector is one into which a desired sequence may be inserted, e.g., by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, hosts, colonies or plaques (e.g., green fluorescent protein).

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence need not encode a protein but may instead, for example, encode a functional RNA such as an shRNA. Accordingly, suitable vectors may be used for expressing an inhibitory RNA to inhibit the expression of a metabolic mesenchymal genes, as described elsewhere herein.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art. One of skill in the art will be aware of appropriate regulatory sequences for expression of interfering RNA, e.g., shRNA, miRNA, etc.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), lentiviral vectors (Naldini L, et al., Proc Natl Acad Sci USA. 1996 Oct. 15; 93(21):11382-8) and Ty virus-like particle (Allsopp et al., Eur. J. Immunol 26:1951-1959, 1996).

Another virus useful for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (i.e., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991).

Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect Gene-Juice® Transfection Reagent by Novagen.

Furthermore, in some embodiments, cells with properties of stem cells may be generated by inhibiting expression of a metabolic mesenchymal gene the product of which inhibits or prevents an epithelial to mesenchymal transition in cells. For example, stem cells may be generated by inhibiting expression in a normal, non-cancer cell of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3.

Various strategies for gene knockdown known in the art can be used to inhibit the expression of metabolic mesenchymal gene and others disclosed herein that are useful for inducing EMT. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, antisense inhibition and other nucleotide-based molecules known in the art. In one embodiment, vector-based RNAi modalities (e.g., shRNA or shRNA-mir expression constructs) are used to reduce expression of a gene (e.g., a metabolic mesenchymal gene) in a cell.

In certain embodiments, the activity of a metabolic mesenchymal gene is inhibited by RNA interference. Methods for inhibiting gene expression by RNA interference are disclosed herein and known in the art. In some embodiments, a cell is transfected with a small interfering nucleic acid complementary to an mRNA of a metabolic mesenchymal gene in the cell. Exemplary small interfering nucleic acids are disclosed herein and are known to persons skilled in the art. Methods for transfection of small interfering nucleic acids (e.g., siRNA) are well known in the art and examples are disclosed herein. In some embodiments, the cell has a stably integrated transgene that expresses a small interfering nucleic acid (e.g., shRNA, miRNA) that is complementary an mRNA and that causes the downregulation of the mRNA through the RNA interference pathway.

A broad range of RNAi-based modalities could be also employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3): 176-83, (2006)). siRNAs with amide-linked oligoribonucleosides have been generated that are more resistant to Si nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun 342(3):919-26, 2006). Other molecules that can be used to inhibit expression of a gene (e.g., a metabolic mesenchymal gene) include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10): 2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, nonspecific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

It should be appreciated that these methods are not limited to generating normal cells with stem cell properties, e.g., for regenerative purposes. In some embodiments, it may be desirable to generate cancer stem cells by inducing an EMT in cancer cells. Such cancer stem cells may be useful for studying cancer development and progression for example, and may be useful for identifying agents that affects EMT and cancer development. Accordingly, in some embodiments, methods are provided for generating cancer stem cells that involve forcing expression in the cancer cells of a metabolic mesenchymal gene the product of which induces an epithelial to mesenchymal transition in the cells. And, in other embodiments, methods are provided for generating cancer stem cells that involve inhibiting expression of a metabolic mesenchymal gene the product of which inhibits or prevents an epithelial to mesenchymal transition in cells.

In some embodiments, stem cells may be generated by forcing expression in a cell of a metabolic gene such as ELOVL5 or HNMT. In some embodiments, stem cells may be generated by forcing expression in a cell of a metabolic gene such as ACLY, AGK, ALDH1L1, ARG2, CDA, DIO01, ELOVL5, GCNT3, GGH, GPX3, HNMT, MAOB, NUDT5, RRM1, ST6GALNAC2, or TYMS.

A variety of cell (including primary cells) have the potential for the generation of cell populations bearing properties of stem cells or cancer stem cells. Epithelial cells arising from epithelium may undergo an EMT in response to cell-extrinsic signaling ligands such as TGFβ or Wnt, or through the forced overexpression of EMT transcription factors such as Twist or Snail, or, as disclosed herein, forced expression of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, or, as disclosed herein, forced expression of a metabolic gene such as ACLY, AGK, ALDH1L1, ARG2, CDA, DIOL ELOVL5, GCNT3, GGH, GPX3, HNMT, MAOB, NUDT5, RRM1, ST6GALNAC2, or TYMS, or, as disclosed herein, inhibiting expression of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3.

Methods of Treatment

Methods are also provided herein for treating subjects having or at risk of having cancer. Generally, the methods involve administering one or more agents that alter the expression or activity of the product of a particular metabolic mesenchymal gene in cells (e.g., cancer cells) of the subject.

The methods may involve, for example, administering to the subject an agent that selectively inhibits activity of the product of a metabolic mesenchymal gene that is upregulated in cancer cells compared with non-cancer cells and/or that induces an EMT in cancer cells. The methods may involve administering to the subject an agent that inhibits expression of a metabolic mesenchymal gene that is upregulated in cancer cells compared with non-cancer cells and/or that induces an EMT in cancer cells. In some embodiments, the administration inhibits or reverses epithelial to mesenchymal transitions in cancer cells, and thereby depletes or inhibits an increase in the numbers of cancer stem cells present in the subject. For example, the methods may involve administering an agent to a subject that inhibits expression of a metabolic mesenchymal gene that promotes epithelial to mesenchymal transitions. In such embodiments, the metabolic mesenchymal gene may be selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. In some embodiments, the methods may involve administering an agent to the subject that inhibits expression of a metabolic gene that promotes epithelial to mesenchymal transitions, such as ACLY, AGK, ALDH1L1, ARG2, CDA, DIO1, ELOVL5, GCNT3, GGH, GPX3, HNMT, MAOB, NUDT5, RRM1, ST6GALNAC2, or TYMS. Accordingly, in some embodiments, the agent is an inhibitory oligonucleotide or a nucleic acid engineered to express an inhibitory RNA that selectively inhibits expression of the gene. In other embodiments, the agent is a compound (e.g., a small molecule) that selectively inhibits the activity of the product of the metabolic mesenchymal gene.

In some embodiments, the methods may involve administering to the subject an agent that selectively induces expression of a metabolic mesenchymal gene that is down-regulated in cancer cells compared with non-cancer cells and/or that inhibits or reverses an EMT in cancer cells. Here again, in some embodiments, the administration inhibits or reverses epithelial to mesenchymal transitions in cancer cells in the subject, and thereby depletes or inhibits an increase in the numbers of cancer stem cells present in the subject. For example, the methods may involve administering an agent to the subject that forces expression of a metabolic mesenchymal gene that inhibits epithelial to mesenchymal transitions, such as, for example, a gene selected from: QPRT, CYBA, PTER, MFNG, TM7SF2, PLCG2, ST6GAL1, CA2, GLB1L2, PIK3C2B, GCH1, ALDH1A1, GPX2, and GALNT3. Accordingly, the agent may comprise a nucleic acid engineered to express the metabolic mesenchymal gene.

According to certain methods provided herein for treating subjects having or at risk of having cancer, a treatment affecting the expression or activity of a metabolic mesenchymal gene, or product thereof, may be administered to the subject within particular period of time of at least one other treatment for the cancer in the subject. The particular period of time may be within 5 years, within 2 years, within 1 year, within 1 month, within 3 weeks, within 2 weeks, within 1 week, within 5 days, within 4 days, within 3 days, within 2 days, within 1 day, within 12 hours, within 6 hours, within 2 hours, within 1 hour or less time. The treatment affecting the metabolic mesenchymal gene may be administered to the subject prior to or after the at least one other treatment for the cancer in the subject. The other treatment may be any appropriate treatment, including, for example, a surgery to remove malignant or premalignant cells from the subject; or radiation therapy directed at eradicating malignant or premalignant cells from the subject; or a conventional chemotherapy treatment; or other appropriate treatment.

In some embodiments, treatment methods provided herein are employed in conjunction with methods provided herein for cancer classification, prognosis, diagnosis, or treatment selection. For example, in some embodiments, the treatment methods involve first determining that a subject has cancer or is at risk of developing cancer and then, having established that the subject has cancer, or is at risk of developing cancer, treating the subject according to the methods provided herein. In some embodiments, the methods involve determining that the subject has a cancer that contains cells that exhibit mesenchymal properties by evaluating the expression of one or more metabolic mesenchymal genes in cells isolated from the subject, e.g., isolated from a region of the subject suspected of containing cancerous tissue. In some embodiments, the methods involve determining that the cancer contains cells that exhibit a metabolic gene mesenchymal signature and, having determined that the cancer contains cells that exhibit a metabolic gene mesenchymal signature, treating the subject according to one or more methods disclosed herein. In some embodiments, the metabolic mesenchymal gene selected from Table 2.

In some embodiments, methods for treating a subject having a cancer of non-mesenchymal origin are provided that involve determining that the subject has an aggressive cancer by evaluating the cancer according to methods disclosed herein; and subjecting the subject to intensive and/or prolonged monitoring for recurrence or metastasis, or subjecting the subject to intensive and/or prolonged therapy for the cancer.

In some embodiments, methods for treating a subject having a cancer of non-mesenchymal origin are provided that involve first subjecting a sample of the cancer obtained from the subject to a gene expression analysis to determine expression levels of one or more metabolic mesenchymal genes in the sample; and comparing the expression levels to reference expression levels of the metabolic mesenchymal genes in appropriate reference cells, in which the results of the comparison are indicative of whether the cancer contains or is enriched for cancer stem cells (CSC). In such embodiments, the methods further comprising determining that the cancer contains or is enriched for CSCs and treating the subject with a CSC-selective agent after determining that the cancer contains or is enriched for CSCs.

Methods described herein have broad application to treating disorders, such as cancer, that are associated with cancer stem cells. Cancer is a disease characterized by uncontrolled or aberrantly controlled cell proliferation and other malignant cellular properties. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

In certain embodiments, cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In one embodiment, cancer is a lung carcinoma. In some embodiments, cancer is a breast carcinoma. Other appropriate cancers, particularly carcinomas, will be known to one of ordinary skill in the art.

Some aspects of the invention are methods for treating a subject having, or suspected of having, cancer comprising administering to the subject an effective amount of a compound that selectively targets cancer stem cells, e.g., by targeting the product of a metabolic mesenchymal gene. In some embodiments, the treatment methods of the invention involve treatment of a subject having (e.g., harboring) or at risk of having a cancer stem cell (CSC) and/or a CSC-dependent tumor. In some embodiments, the subject has a tumor of epithelial origin (i.e., a carcinoma).

As used herein, a subject is a mammal, including but not limited to a dog, cat, horse, cow, pig, sheep, goat, chicken, rodent, or primate. Preferred subjects are human subjects. The human subject may be a pediatric or adult subject. In some embodiments the adult subject is a geriatric subject. Whether a subject is deemed "at risk" of having a tumor is a determination that may be within the discretion of the skilled practitioner caring for the subject. Any suitable diagnostic test and/or criteria can be used. For example, a subject may be considered "at risk" of having a tumor if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc. In some embodiments, if the compound is one that has been previously (prior to the instant invention) administered to subjects for purposes other than treating cancer, e.g., for treatment of a condition other than cancer, the subject is not one to whom the compound would normally be administered for such other purpose and/or the compound is administered in a formulation or at a dose distinct from that known in the art to be useful for such other purpose.

Moreover, as used herein treatment or treating includes amelioration, cure, and/or maintenance of a cure (i.e., the prevention or delay of relapse) of a disorder (e.g, a tumor). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). A suitable dose and therapeutic regimen may vary depending upon the specific compound used, the mode of delivery of the compound, and whether it is used alone or in combination.

As used herein, a therapeutically effective amount generally refers to an amount of a compound that inhibits formation, progression, growth and/or spread (e.g., metastasis) of a tumor or cell. In some embodiments, therapeutically effective amount is an amount of a compound sufficient to inhibit growth of a cell. A therapeutically effective amount can refer to any one or more of the compounds or compositions described herein, or discovered using the methods described herein, that inhibit the growth and/or survival of cells, e.g., CSCs. In some embodiments, a therapeutically effective amount is an amount sufficient to affect the expression or activity of the product of a metabolic mesenchymal gene in a cell.

In some embodiments, a therapeutically effective amount is an amount of an agent (e.g., a compound) sufficient to inhibit the activity or expression in a cell of the product of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1. In some embodiments, a therapeutically effective amount is an amount of an agent (e.g., a compound) sufficient to inhibit the activity or expression in a cell of the product of a metabolic mesenchymal gene selected from: DPYD, DPYSL2, DPYSL3, PPAP2B, MICAL2, PPAPDC1A, GPX8, MGST1, PLCB4, COX7A1, EXT1, DSEL, B3GNT9, CA12, HS3STSA1, MSRB3, SULF1, and UAP1. In some embodiments, a therapeutically effective amount is an amount of an agent (e.g., a compound) sufficient to inhibit the activity or expression in a cell of the product of a metabolic gene selected from: ACLY, AGK, ALDH1L1, ARG2, CDA, DIO01, ELOVL5, GCNT3, GGH, GPX3, HNMT, MAOB, NUDT5, RRM1, ST6GALNAC2, or TYMS. In some embodiments, a therapeutically effective amount is an amount sufficient to induced expression of QPRT, CYBA, PTER, MFNG, TM7SF2, PLCG2, ST6GAL1, CA2, GLB1L2, PIK3C2B, GCH1, ALDH1A1, GPX2, and GALNT3.

In some embodiments, treatment methods involve administering 4-methylumbelliferone or an analog thereof in an amount sufficient to inhibit the activity of HAS2 protein in cells of the subject.

In some embodiments, treatment methods involve administering coumarin or an analog thereof in an amount sufficient to inhibit the activity of CA12 protein in cells of the subject. Some naturally occurring coumarin derivatives include umbelliferone (7-hydroxycoumarin), aesculetin (6,7-dihydroxycoumarin), hemiarin (7-methoxycoumarin), psoralen and imperatorin.

In some embodiments, treatment methods involve administering a GABA analog, such as gabapentin, pregabalin, atagabalin or analog of any one of these agents in an amount sufficient to inhibit the activity of BCAT1 protein in cells of the subject.

In some embodiments, treatment methods involve administering JZL184 or an analog thereof in an amount sufficient to inhibit the activity of MGLL protein in cells of the subject.

In some embodiments, treatment methods involve administering miglustat or an analog thereof in an amount sufficient to inhibit the activity of UGCG protein in cells of the subject.

In some embodiments, treatment methods involve administering phosphoramidon or an analog thereof in an amount sufficient to inhibit the activity of MME protein in cells of the subject.

In some embodiments, treatment methods involve administering raloxifene or an analog thereof in an amount sufficient to inhibit the activity of AOX1 protein in cells of the subject.

In some embodiments, treatment methods involve administering ribavirin or an analog thereof in an amount sufficient to inhibit the activity of ENPP1 protein in cells of the subject.

In some embodiments, treatment methods involve administering 53826 or an analog thereof in an amount sufficient to inhibit the activity of ENPP2 protein in cells of the subject.

In some embodiments, treatment methods involve administering SK1-I (BML-258) or an analog thereof in an amount sufficient to inhibit the activity of SPHK1 protein in cells of the subject.

In some embodiments, treatment methods involve administering an aldose reductase inhibitor, such as sorbinil, epalrestat, ranirestat, fidarestat, zopolrestat or an analog of any one of these agents, in an amount sufficient to inhibit the activity of AKR1B1 protein in cells of the subject. Aldose reductase (or aldehyde reductase) is an NADPH-dependent oxidoreductase that catalyzes the reduction of a variety of aldehydes and carbonyls, including monosaccharides. It is known for catalyzing the reduction of glucose to sorbitol, the first step in polyol pathway of glucose metabolism. Other aldose reductase inhibitors are disclosed in MacCari, R, et al, (2011). "In vitro evaluation of 5-arylidene-2-thioxo-4-thiazolidinones active as aldose reductase inhibitors". Bioorganic & Medicinal Chemistry Letters 21 (1): 200-3. doi: 10.1016/j.bmcl.2010.11.041. PMID), the contents of which relating to aldose reductase inhibitors are incorporated herein by reference.

In some embodiments, treatment methods involve administering TMS or an analog thereof in an amount sufficient to inhibit the activity of CYP1B1 protein in cells of the subject.

In some embodiments, treatment methods involve administering gimeracil or an analog thereof in an amount sufficient to inhibit the activity of DPYD protein in cells of the subject. In some embodiments, the methods further comprise administering 5-FU to the subject. However, in some embodiments, the gimeracil or analog thereof is administered in the absence of 5-FU or other chemotherapy agents metabolized by DPYD.

Methods for establishing a therapeutically effective amount for any compounds or compositions described herein will be known to one of ordinary skill in the art. As used herein, pharmacological compositions comprise compounds or compositions that have therapeutic utility, and a pharmaceutically acceptable carrier, e.g., that facilitate delivery of compounds or compositions, in a therapeutically effective amount. The effective amount for any particular application can also vary depending on such factors as the cancer being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned with the goal of avoiding substantial toxicity and yet effective to treat the particular subject. In some embodiments a useful compound increases the average length of survival, increases the average length of progression-free survival, and/or reduces the rate of recurrence, of subjects treated with the compound in a statistically significant manner.

Subject doses of the compounds described herein typically range from about 0.1 µg to 10,000 mg, more typically from about 1 µg to 8000 mg, e.g., from about 10 µg to 100 mg once or more per day, week, month, or other time interval. Stated in terms of subject body weight, typical dosages in certain embodiments of the invention range from about 0.1 µg to 20 mg/kg/day, e.g., from about 1 to 10 mg/kg/day, e.g., from about 1 to 5 mg/kg/day. In certain embodiments reduced dose may be used when different pathway inhibitors are administered in combination either concomitantly or sequentially. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is often the case that a maximum dose be used, that is, the highest safe dose according to sound medical judgment.

The dose used may be the maximal tolerated dose or a sub-therapeutic dose or any dose there between. Multiple doses of the molecules of the invention are also contemplated. When the molecules of the invention are administered in combination a sub-therapeutic dosage of either of the molecules, or a sub-therapeutic dosage of both, may be used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences; as well as many other medical references relied upon by the medical profession as guidance for the treatment of cancer.

The compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds of the invention may, for example, be inhaled, ingested or administered by systemic routes. Thus, a variety of administration modes, or routes, are available. The particular mode selected will depend, of course, upon the particular compound selected, the particular condition being treated and the dosage required for therapeutic efficacy. The methods of this invention, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Other appropriate routes will be apparent to one of ordinary skill in the art.

According to the methods of the invention, the compounds may be administered in a pharmaceutical composition. Administering the pharmaceutical composition of the present invention may be accomplished by any means known to the skilled artisan. In addition to the active agent, the pharmaceutical compositions of the present invention typically comprise a pharmaceutically-acceptable carrier. The term "pharmaceutically-acceptable carrier", as used herein, means one or more compatible solid or liquid filler diluents or encapsulating substances which are suitable for administration to a human or lower animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present.

The pharmaceutically-acceptable carrier employed in conjunction with the compounds of the present invention is used at a concentration sufficient to provide a practical size to dosage relationship. The pharmaceutically-acceptable carriers, in total, may comprise from about 60% to about 99.99999% by weight of the pharmaceutical compositions of the present invention, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but nonpharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that the compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences). Those of skill in the art can readily determine the various parameters and conditions for producing aerosols without resort to undue experimentation.

The compounds of the invention may be administered directly to a tissue. Preferably, the tissue is one in which the cancer cells are found. Alternatively, the tissue is one in which the cancer is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application Publication No. WO 95/24929, entitled "Polymeric Gene Delivery System", which reports on a biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Cells

Aspects of the invention provide test cells and control cells, for example test and control cells that are useful for identifying compounds that specifically target the products of metabolic mesenchymal genes (e.g., a gene listed in Table 2) and/or that specifically target cancer stem cells. In some embodiments, the test cells are cells that have been determined to exhibit a metabolic gene mesenchymal signature. As described herein, test or control cells can be primary cells, non-immortalized cell lines, immortalized cell lines, transformed immortalized cell lines, benign tumor derived cells or cell lines, malignant tumor derived cells or cell lines, transgenic cell lines, etc. In some embodiments the tumor is a metastatic tumor, in which case the cells may be derived from the primary tumor or a metastasis. In some embodiments, test cells are cells that have undergone or that have the capacity to undergo an epithelial to mesenchymal transition.

In some embodiments, test cells may be cells that are engineered to express an inhibitory RNA that selectively inhibits expression of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3. Test cells may be cells that are engineered to express a metabolic mesenchymal gene selected from the group consisting of: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1.

In some embodiments, the effects of one or more conditions on test cells (e.g., exposing the test cells to an agent that effects expression or activity of a metabolic mesenchymal cell) are compared with the effects of the same one or more conditions in appropriate reference cells. As used herein, "appropriate reference cells" are control cells suitable for determining whether one or more conditions effect test cells in particular way. Reference cells may therefore serve as positive or negative controls. In some embodiments, control cells are mesenchymal cells. In some embodiments, control cells are non-mesenchymal cells (e.g., epithelial cells).

In one embodiment, a control cell is a cancer stem cell, optionally which expresses one or more cancer stem cell biomarker(s). In certain embodiments, a cancer stem cell biomarker is selected from E-Cadherin, TWIST, and a $CD44^+CD24^-$ marker profile. Non limiting cancer stem cell biomarkers include: CD20, CD24, CD34, CD38, CD44, CD45, CD105, CD133, CD166, EpCAM, ESA, SCA1, Pecam, Strol, $FOXC2^{pos}$, N-cadherin$^{high}$, E-cadherin$^{low/neg}$, alpha-catenin$^{low/neg}$, gamma-catenin$^{low/neg}$, vimentin$^{pos}$, and fibronectin$^{pos}$. Other exemplary cancer stem cell markers will be apparent to one of ordinary skill in the art. In some embodiments, a control cell is a cell that has undergone an EMT, for example a cell that has reduced E-Cadherin expression.

In some embodiments, a control cell is a cancer cell that is not a cancer stem cell, optionally which does not exhibit detectable expression of one or more cancer stem cell biomarker(s). More than one set of control cells may be provided, such as cancer cells that are not cancer stem cells and non-cancer cells. Cells (test or reference) may be subjected to one or more genetic or chemical perturbations (e.g., siRNA treatment or other treatment) and then incubated for a predetermined time. The predetermined time is a time sufficient to produce a desired effect in a control cell (e.g., inhibit the growth and/or survival thereof).

In some embodiments the cells are mammalian cells, e.g., human cells or non-human animal cells, e.g., cells of non-human primate, rodent (e.g., mouse, rat, guinea pig, rabbit), origin, or interspecies hybrids. In certain embodiments the test and control cells are obtained from a biopsy (e.g., tissue biopsy, fine needle biopsy, etc.) or at surgery for a cancerous or noncancerous condition.

In some embodiments, cells (e.g., test cells, controls cells) of the invention may be derived from a cancer (e.g., naturally occurring cancer). In some embodiments, cells (e.g., test cells, controls cells) of the invention may be derived from a cancer of epithelial origin (e.g., breast cancer). In some embodiments, the cancer from which cells are derived is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, melanoma, or a testicular tumor. In one embodiment, cancer is a lung carcinoma. In one embodiment, cancer is a breast carcinoma. Other cancers will be known to one of ordinary skill in the art. In some embodiments the cancer is a spontaneously arising cancer. In some embodiments the cancer is a cancer associated with a known or characteristic genetic mutation or polymorphism. In some embodiments the cancer is an experimentally produced cancer. In some embodiments the cancer is a hormone-responsive cancer. In some embodiments the cells are derived from an early stage cancer or precancerous lesion, e.g., a papilloma, adenoma, dysplastic lesion, etc., or a carcinoma in situ. In some embodiments the cancer is one that is responsive to a chemotherapeutic agent or combination thereof (e.g., any one or more of the chemotherapeutic agents discussed below). In some embodiments the cancer is one that is resistant to a chemotherapeutic agent or combination thereof.

In some embodiments, cancer cells are experimentally produced. Cancer cells can be experimentally produced by a number of methods known in the art that result in transformation of a non-cancer cell (non-transformed cell) to a cancer cell (transformed cell). Such experimentally produced cancer cells may be metastatic or non-metastatic.

As certain cells undergo senescence naturally after multiple rounds of cell division and cannot be passaged for prolonged periods, it is often advantageous to immortalize them with hTert and, in some embodiments, subsequently transform them with a SV40-LargeT antigen to allow for their long-term maintenance in vitro. These cells can subsequently be tested for their ability to undergo an epithelial-mesenchymal transition (EMT) and assayed for the gain of stem cell properties. Further introduction of an oncogenic H-Ras (G12V) can confer these cells with tumorigenic potential including the generation of cancer stem cells. Thus, it is possible to generate populations of cancer stem cells and non-CSCs for the purpose of therapeutic screening. Non-limiting examples of cells that are useful for generating cell populations bearing properties of stem cells or cancer stem cells, include: NHBE (Lonza, CC-2540): normal human bronchial/tracheal epithelial cells (for the study of lung cancer); PrEC (Lonza, CC-2555): human prostate epithelial cells (for the study of prostate cancer); InEpC (Lonza, CC-2931): human intestinal epithelial cells (for the study of gastrointestinal cancers); and HPNE-hTert (ATCC, CRL-4023): human pancreas ductal epithelial cells (for the study of pancreatic cancer). Further examples, e.g., HMLE cells, are disclosed in International Application Publication Number, WO/2009/126310, entitled, METHODS FOR IDENTIFICATION AND USE OF AGENTS TARGETING CANCER STEM CELLS, the contents of which are incorporated herein by reference.

In some embodiments, carcinoma cells are provided that comprise basal-like cancer cells. In some embodiments, carcinoma cells arise from the airway epithelium, pancreas ductal epithelium, intestinal epithelium, prostate epithelium or breast epithelium. In some embodiments, the carcinoma cells are carcinoma cells (e.g., from breast epithelium) characterized as $Her2^{neg}$, $ER^{neg}$, and/or $PR^{neg}$.

In some cases, cancer cells are produced from non-cancer cells by transfecting the non-cancer cells (transiently or stably) with one or more expression vector(s) encoding an oncogene. Such oncogenes, when expressed, lead to neoplastic or hyperplastic transformation of a cell. The oncogene may be a complete sequence of the oncogene, preferably an oncogenic form of the oncogene, or it may be a fragment of the oncogene that maintains the oncogenic potential of the oncogene. Exemplary oncogenes include MYC, SRC, FOS, JUN, MYB, RAS, ABL, BCL2, HOXI1, HOX1 1L2, TAL1/SCL, LMO1, LMO2, EGFR, MYCN, MDM2, CDK4, GLI1, IGF2, activated EGFR, mutated genes, such as FLT3-ITD, mutated of TP53, PAX3, PAX7, BCR/ABL, HER2/NEU, FLT3R, FLT3-ITD, SRC, ABL, TAN1, PTC, B-RAF, PML-RAR-alpha, E2A-PBX1, and NPM-ALK, as well as fusion of members of the PAX and FKHR gene families Other exemplary oncogenes are well known in the art and several such examples are described in, for example, The Genetic Basis of Human Cancer (Vogelstein, B. and Kinzler, K. W. eds. McGraw-Hill, New York, N.Y., 1998). Homologues of such genes can also be used.

In some cases, cancer cells can be produced from non-cancer cells by transfecting the non-cancer cells (transiently or stably) with one or more expression vector(s) encoding an inhibitory molecule (e.g., shRNA, mirRNA) capable of inhibiting the expression of a tumor suppressor gene. Such inhibitory molecules, when expressed, lead to neoplastic or hyperplastic transformation of a cell. Exemplary tumor suppressor genes include RB, TP53, APC, NF-1, BRCA-1, BRCA-2 and WT-1. Other exemplary tumor suppressor genes are well known in the art.

In some cases, cancer cells can be produced from non-cancer cells by transfecting the non-cancer cells (transiently or stably) with one or more expression vector(s) encoding an inhibitory molecule (e.g., shRNA) capable of inhibiting the expression of a tumor suppressor gene and one or more expression vector(s) encoding an oncogene.

In some embodiments, cells (e.g., test cells, control cells) of the invention are derived from noncancerous tissue. For example, the cells may be derived from any epithelial tissue. One of skill in the art will appreciate that "epithelium" refers to layers of cells that line the cavities and surfaces of structures throughout the body and is also the type of tissue of which many glands are at least in part formed. Such tissues include, for example, tissues found in the breast, gastrointestinal tract (stomach, small intestine, colon), liver, biliary tract, bronchi, lungs, pancreas, kidneys, ovaries, prostate, skin, cervix, uterus, bladder, ureter, testes, exocrine glands, endocrine glands, blood vessels, etc. In some embodiments the epithelium is endothelium or mesothelium. In certain embodiments the cells are human breast epithelial cells. In certain embodiments the cells are noncancerous human breast cells obtained from a reduction mammoplasty. In certain embodiments, the test and control cells are derived from any cell type that normally expresses E-cadherin. In certain embodiments, the test and control cells are of a cell type that does not normally express N-cadherin. In certain embodiments, the test and control cells are of a cell type that normally expresses E-cadherin at levels at least 5, 10, 20, 50, or 100-fold higher levels, on average, than those at which it expresses N-cadherin.

In some embodiments the cells (test and/or control) have been modified, e.g., genetically modified, so as to express, inhibit, or delete one or more oncogenes or tumor suppressor genes. In some embodiments such modification immortalizes the cells. In some embodiments such modification transforms the cells to tumorigenic cells. For example, in certain embodiments test and/or control cells are immortalized by expressing telomerase catalytic subunit (e.g., human telomerase catalytic subunit; hTERT) therein. In certain embodiments test and/or control cells are transformed by expressing SV40 (e.g., early region) or Ras, optionally activated Ras such as H-rasV12, therein. In some embodiments cells are modified or treated so as to have reduced or essentially absent expression and/or functional activity of cell cycle checkpoint or DNA damage sensing proteins, e.g., p16, e.g., p16$^{INK4a}$, p53 and/or retinoblastoma (Rb) proteins. For example, cells can be modified to express a shRNA targeted to one or more of these genes, or to express a viral protein that binds to one or more of these proteins. Combinations of such modifications can be used. For example, cells may be modified to express SV40 large T (LT), hTERT, and H-rasV12. Other means of immortalizing and/or transforming cells are known in the art and are within the scope of the invention.

In certain embodiments of the invention the test cells and control cells are derived from an initial population of substantially identical cells that have not undergone an EMT. Certain of these cells are manipulated so as to render them suitable for use as test cells, e.g., by modifying them so as to be able to induce EMT in a controlled manner and then inducing EMT or by treating them with an agent that induces EMT, e.g., as described herein. In certain embodiments such as these the test and control cells are genetically matched but have one or several defined genetic differences such as those described herein that result in the test cells having undergone EMT while the control cells have not undergone EMT. In certain embodiments, two populations of cells derived from the same starting population, wherein one population has been modified by introducing a vector and the other population has not been so modified. In certain embodiments, two populations of cells derived from the same starting population, wherein one population has been modified by introducing an expression construct encoding an inhibitory nucleic acid or protein element and the other population has been modified by introducing a expression construct encoding a control nucleic acid or protein element (e.g., one that would not be expected to inhibit an endogenous cellular gene or protein). Typically the expression constructs are otherwise similar or identical. In certain embodiments of the invention, the test cells and control cells are genetically matched and contain an expression construct (optionally integrated into the genome) comprising a sequence encoding a short interfering RNA capable of inducing EMT (such as a shRNA or miRNA targeted to a metabolic mesenchymal gene), wherein the sequence is operably linked to a regulatable (e.g., inducible or repressible) promoter. In certain embodiments of the invention, the test cells and control cells are genetically matched and contain an expression construct (optionally integrated into the genome) comprising a sequence encoding a protein capable of inducing EMT, wherein the sequence is linked to a regulatable (e.g., inducible or repressible) promoter. Regulatable expression systems are known in the art and include, e.g., systems utilizing promoters that are inducible by heavy metals, small molecules, etc. Drug-regulatable promoters that are suited for use in mammalian cells include the tetracycline/doxycycline regulatable promoter systems.

"Genetically matched" includes cells or populations of cells that have largely identical genomes, e.g., their genomes are at least 95%, 98%, 99%, 99.5%, 99.9%, 99.99% identical, or more. Typically, genetically matched cells are derived from the same subject or, in the case of certain species such as mice or rats, from different subjects belonging to a particular inbred strain. In some embodiments genetically matched cells are derived from the same tissue sample. In some embodiments of the invention, test and control cells will have been derived from the same initial population of genetically matched cells and will have undergone no more than 2, 5, 10, 15, 20, 25, 30, 35, 40, 50, 60, 70, 80, 90, or 100 rounds of cell division before being used in an inventive method. In some embodiments two or more cells or cell lines may be identified as having originated from the same sample or subject. If desired, cells may be tested to confirm whether they are derived from a single subject, sample, or a particular cell line by any of a variety of methods known in the art such as DNA fingerprinting (e.g., short tandem repeat (STR) analysis) or single nucleotide polymorphism (SNP) analysis (which may be performed using, e.g., SNP arrays (e.g., SNP chips) or sequencing).

The invention provides genetically matched test cells (or cells that can be induced to undergo an EMT) and control cells and kits containing such cells (e.g., test cells, control cells, or both test cells and control cells, e.g., in separate containers). In some embodiments, test cells comprise naturally arising mesenchymal cells that are formed, e.g., in the absence of introduced exogenous EMT-inducing transcription factors, such as Twist, Snail and Slug and/or in the absence of genetic modification that inhibits E-cadherin expression.

In some embodiments the test cells and control cells express different detectable markers. In some embodiments, cells may be provided as a frozen vial containing cells, e.g., in a suitable medium. The medium may comprise one or more agents for cryopreservation.

In some embodiments, epithelial cells are provided that have undergone a mesenchymal to epithelial transition (MET). In some embodiments, such epithelial cells are generated from normal mesenchymal cells. In some embodiments, such epithelial cells are generated from cancer stem cells. In some embodiments, such epithelial cells are generated from cells of epithelial origin that have undergone an EMT or that are progeny of such cells. Thus, in some embodiments, the methods may be used to revert cells that have undergone an EMT and acquired one or more mesenchymal characteristics back to cells having an epithelial phenotype. In some embodiments, such epithelial cells are generated by forced expression in the cells of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3. In some embodiments, such epithelial cells are generated by inhibiting expression in the cells of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, or by inhibiting expression in the cells of a metabolic gene such as ACLY, AGK, ALDH1L1, ARG2, CDA, DIO1, ELOVL5, GCNT3, GGH, GPX3, HNMT, MAOB, NUDT5, RRM1, ST6GALNAC2, or TYMS.

Screening Methods

In some embodiments, methods are provided for identifying agents that specifically target the product of a metabolic mesenchymal gene. In some embodiments, screening may be carried out in vitro or in vivo using any of the assays disclosed herein, or any assay known to one of ordinary skill in the art to be suitable for contacting a test cell with an agents and assaying for a parameter of interest, e.g., for the activity of a metabolic mesenchymal gene and/or for alterations in the growth and/or survival cells.

In some embodiments, the test cells are cells that have been determined to exhibit a metabolic gene mesenchymal signature. In some embodiments, the methods involve exposing the test cells to a test agent and determining the extent to which the test agent inhibits growth or invasiveness of the test cells. Test agents that inhibit growth or invasiveness of the tests cells are identifying as candidate cancer stem cell targeting agents.

In some embodiments, methods are provided for identifying metabolic mesenchymal genes that inhibit an epithelial to mesenchymal transition (EMT). The methods may involve, for example, forcing expression of or inhibiting expression of a metabolic mesenchymal gene in a test cell and subjecting the test cell to a condition suitable for inducing an EMT, while the metabolic mesenchymal gene is expressed or inhibited. The methods permit one to identify metabolic mesenchymal genes that control EMT in the cells. Thus, in some embodiments, the methods involve determining whether the test cells express one or more biomarkers that are indicative of an EMT. In some embodiments, if the one or more biomarkers indicates that the EMT has not occurred in the test cell, then the metabolic mesenchymal gene is identified as a metabolic mesenchymal gene that controls EMT. If expression or activity of the metabolic mesenchymal gene is inhibited during induction of the EMT and the EMT does not occur, then the metabolic mesenchymal gene is identified as promoting the EMT. Similarly, if expression of the metabolic mesenchymal gene is induced during induction of the EMT and the EMT does not occur, then the metabolic mesenchymal gene is identified as inhibiting the EMT.

Reduced expression of certain of the MGMS-downregulated genes (not tested in the shRNA screen described here) may promote or be required for EMT. In other words, expression of certain of the MGMS-downregulated genes, e.g., at or above the level at which they are expressed in most non-mesechymally derived cancers, may inhibit EMT. Such genes may be identified using an approach that involves forced expression of the MGMS-downregulated genes in HMLE-TWIST cells.

Activation of TWIST with tamoxifen normally causes HMLE-TWIST cells to undergo EMT, accompanied by increased expression of mesenchymal markers and decreased expression of epithelial markers. If loss of expression of an MGMS-downregulated gene promotes or is required for EMT, an increased proportion of tamoxifen-treated HMLE-TWIST cells forced to express that gene will retain an epithelial marker expression pattern than would be the case in the absence of forced expression of the gene.

Identification of MGMS-downregulated genes that inhibit EMT may be performed by testing the effects of forced expression of individual genes on the ability of HMLE-TWIST cells (or other suitable cells) forced to express a particular MGMS-downregulated gene to undergo EMT, e.g., using individual cell lines, co-cultures (e.g., HMLE-TWIST cells in co-culture with HMLE-TWIST cells forced to express a particular MGMS-downregulated gene), or using a pooled screen approach in which a pool of vectors comprising open reading frames (e.g., cDNAs) encoding MGMS-downregulated genes are introduced into HMLT-TWIST cells; the cells are treated with tamoxifen; cell populations expressing mesenchymal or epithelial marker patterns are isolated; DNA or RNA encoding the MGMS-downregulated genes is isolated from the cell populations, and the genes are identified, e.g., based on sequence.

MGMS-downregulated genes that inhibit EMT are expected to be underrepresented in the mesenchymal population and/or overrepresented in the epithelial cell population. Agents that enhance expression or activity of those MGMS-downregulated genes that inhibit EMT (or their gene products) may be useful, e.g., to inhibit EMT. Agents that inhibit expression or activity of those MGMS-downregulated genes that inhibit EMT (or their gene products) may be useful, e.g., to promote EMT.

In one aspect agents (e.g., compounds) are contacted with test cells (and optionally control cells) at a predetermined dose. In one embodiment the dose may be about up to 1 nM. In another embodiment the dose may be between about 1 nM and about 100 nM. In another embodiment the dose may be between about 100 nM and about 10 uM. In another embodiment the dose may be at or above 10 uM. Following incubation for an appropriate time, optionally a predetermined time, the effect of agents on the growth and/or survival of the test cell is determined by an appropriate method known to one of ordinary skill in the art. Cells can be contacted with agents for various periods of time. In certain embodiments cells are contacted for between 12 hours and 20 days, e.g., for between 1 and 10 days, for between 2 and 5 days, or any intervening range or particular value. Cells can be contacted transiently or continuously.

As used herein, "suppress", "inhibit", or "reduce" may, or may not, be complete. For example, cell proliferation, may, or may not, be decreased to a state of complete arrest for an effect to be considered one of suppression, inhibition or reduction of cell proliferation. Similarly, gene expression may, or may not, be decreased to a state of complete cessation for an effect to be considered one of suppression, inhibition or reduction of gene expression. Moreover, "suppress", "inhibit", or "reduce" may comprise the maintenance of an existing state and the process of bringing about a state change. For example, inhibition of an epithelial to mesenchymal transition may refer to the prevention of an EMT in a cell and/or the process of reversing an EMT in a cell, i.e., inducing a mesenchymal to epithelial cell transition. Similarly, inhibition of cell survival may refer to killing of a cell, or cells, such as by necrosis or apoptosis, and the process of rendering a cell susceptible to death, such as by inhibiting the expression or activity of an anti-apoptotic regulatory factor. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99% of a reference level (e.g., a control level).

In some cases the level of modulation (e.g., suppression, inhibition, or reduction) compared with a control level is statistically significant. As used herein, "statistically significant" refers to a p-value of less than 0.05, e.g., a p-value of less than 0.025 or a p-value of less than 0.01, using an appropriate statistical test (e.g, ANOVA, t-test, etc.).

In certain embodiments, the effects of an agent on the growth and/or survival of the test cell and/or control cell is determined. For example, these effects may be determined using a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Other exemplary assays include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CellTitre Glo; Nuclear Fragmentation Assays; Cytoplasmic Histone Associated DNA Fragmentation Assay; PARP Cleavage Assay; TUNEL staining; and Annexin staining. In one embodiment, gene expression analysis (e.g., microarray, cDNA array, quantitative RT-PCR, RNAse protection assay) is employed to examine the expression of genes whose products mediate cell cycle/growth and/or survival.

In other embodiments, alterations the status of a test cell and/or control cell may be assessed by examining protein levels, for example the level of a cancer stem cell marker, or a protein indicative of an EMT. Protein levels can be assessed by any appropriate method known to one of ordinary skill in the art, such as western analysis. Other methods known to one of ordinary skill in the art could be employed to analyze proteins levels, for example immunohistochemistry, immunocytochemistry, ELISA, radioimmunoassays, proteomics methods, such as mass spectroscopy or antibody arrays.

Still other parameters disclosed herein that are relevant for assessing cells in assays for screening for agents for their effects, e.g., on the products of metabolic mesenchymal genes. For example, high-content imaging or Fluorescence-activated cell sorting (FACS) of cells may be used. In one embodiment, the effect of a compound on a test cell and/or control cell can be assessed by evaluating the apoptotic state of the test cell using automated microscopic imaging or FACS (See for example United States Patent Publication 20070172818). In some cases, fluorescence-based TUNEL staining (e.g., using a FITC-dUTP with standard TUNEL methods known in the art) can reveal apoptosis in a test cell and/or control cell. Other methods include immunocytochemistry using an antibody (e.g., cleaved PARP, cleaved Lamin A, etc.) to detect caspase activity. These examples of imaging are not intended to be limiting, and other similar methods will be readily apparent to one of ordinary skill in the art.

The foregoing assay methods of the invention are amenable to high-throughput screening (HTS) implementations. In some embodiments, the screening assays of the invention are high throughput or ultra-high throughput (e.g., Fernandes, P. B., Curr Opin Chem Biol. 1998 2:597; Sundberg, S A, Curr Opin Biotechnol. 2000, 11:47). HTS refers to testing of up to, and including, 100,000 compounds per day. Whereas ultra-high throughput (uHTS) refers to screening in excess of 100,000 compounds per day. The screening assays of the invention may be carried out in a multi-well format, for example, a 96-well, 384-well format, or 1,536-well format, and are suitable for automation. In the high throughput assays of the invention, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays of the invention. Typically, HTS implementations of the assays disclosed herein involve the use of automation. In some embodiments, an integrated robot system consisting of one or more robots transports assay microplates between multiple assay stations for compound, cell and/or reagent addition, mixing, incubation, and finally readout or detection. In some aspects, an HTS system of the invention may prepare, incubate, and analyze many plates simultaneously, further speeding the data-collection process. High throughput screening implementations are well known in the art. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Wiser, the contents of which are both incorporated herein by reference in their entirety.

As described herein, compounds or compositions that substantially affect the growth and/or survival of a test cell, and/or that are candidate modulators of the EMT program can be uncovered using the disclosed test methods. Examples of types of compounds or compositions that may be tested include, but are not limited to: anti-metastatic agents, cytotoxic agents, cytostatic agents, cytokine agents, anti-proliferative agents, immunotoxin agents, gene therapy agents, angiostatic agents, cell targeting agents, HDAC inhibitory agents, etc. In some embodiments, the test compound is a kinase inhibitor.

The following provides further examples of test compounds and is not meant to be limiting. Those of ordinary skill in the art will recognize that there are numerous additional types of suitable test compounds that may be tested using the methods, cells, and/or animal models of the invention. Test compounds can be small molecules (e.g., compounds that are members of a small molecule chemical library). The compounds can be small organic or inorganic molecules of molecular weight below about 3,000 Daltons. The small molecules can be, e.g., from at least about 100 Da to about 3,000 Da (e.g., between about 100 to about 3,000 Da, about 100 to about 2,500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be natural products, synthetic products, or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art (e.g., as exemplified by Obrecht and Villalgrodo, Solid-Supported Combinatorial and Parallel Synthesis of Small-Molecular-Weight Compound Libraries, Pergamon-Elsevier Science Limited (1998)), and include those such as the "split and pool" or "parallel" synthesis techniques, solid-phase and solution-phase techniques, and encoding techniques (see, for example, Czarnik, A. W., Curr Opin. Chem. Biol. (1997)

1:60). In addition, a number of small molecule libraries are publicly or commercially available (e.g., through Sigma-Aldrich, TimTec (Newark, Del.), Stanford School of Medicine High-Throughput Bioscience Center (HTBC), and ChemBridge Corporation (San Diego, Calif.).

Compound libraries screened using the new methods can comprise a variety of types of test compounds. A given library can comprise a set of structurally related or unrelated test compounds. In some embodiments, the test compounds are peptide or peptidomimetic molecules. In some embodiments, test compounds include, but are not limited to, peptide analogs including peptides comprising non-naturally occurring amino acids, phosphorous analogs of amino acids, amino acids having non-peptide linkages, or other small organic molecules. In some embodiments, the test compounds are peptidomimetics (e.g., peptoid oligomers, e.g., peptoid amide or ester analogues, D-peptides, L-peptides, oligourea or oligocarbamate); peptides (e.g., tripeptides, tetrapeptides, pentapeptides, hexapeptides, heptapeptides, octapeptides, nonapeptides, decapeptides, or larger, e.g., 20-mers or more); cyclic peptides; other non-natural peptide-like structures; and inorganic molecules (e.g., heterocyclic ring molecules). Test compounds can also be nucleic acids.

The test compounds and libraries thereof can be obtained by systematically altering the structure of a first "hit" compound, also referred to as a lead compound, that has a desired effect, and correlating the structure of that compound to a resulting biological activity (e.g., a structure-activity relationship study). Such libraries can be obtained using any of the numerous approaches in combinatorial library methods known in the art, including: peptoid libraries (libraries of molecules having the functionalities of peptides, but with a novel, non-peptide backbone which are resistant to enzymatic degradation but which nevertheless remain bioactive; see, e.g., Zuckermann, et al., J. Med. Chem., 37:2678-85 (1994)); spatially addressable parallel solid phase or solution phase libraries; synthetic library methods requiring deconvolution; the "one-bead on e-Compound" library method; and synthetic library methods using affinity chromatography selection (Lam, Anticancer Drug Des. 12:145 (1997)). Examples of methods for the synthesis of molecular libraries can be found in the art, for example in: DeWitt et al., Proc. Natl. Acad. Sci. USA, 90:6909 (1993); Erb et al., Proc. Natl. Acad. Sci. USA, 91:11422 (1994); Zuckermann et al., J. Med. Chem., 37:2678 (1994); Cho et al., Science, 261:1303 (1993); Carrell et al., Angew. Chem. Int. Ed. Engl., 33:2059 (1994); Carell et al., Angew. Chem. Int. Ed. Engl., 33:2061 (1994); and in Gallop et al., J. Med. Chem., 37:1233 (1994). Libraries of compounds can be presented in solution (e.g., Houghten (1992) Biotechniques, 13:412-421), or on beads (Lam (1991) Nature, 354:82-84), chips (Fodor (1993) Nature, 364:555-556), bacteria (Ladner, U.S. Pat. No. 5,223,409), spores (Ladner, U.S. Pat. No. 5,223,409), plasmids (Cull et al. (1992) Proc. Natl. Acad. Sci. USA, 89:1865-1869) or on phage (Scott and Smith (1990) Science, 249:386-390; Devlin (1990) Science, 249:404-406; Cwirla et al. (1990) Proc. Natl. Acad. Sci. USA, 87:6378-6382; Felici (1991) J. Mol. Biol., 222:301-310; Ladner, supra.).

In some embodiments, the methods of the invention are used to screen "approved drugs". An "approved drug" is any compound (which term includes biological molecules such as proteins and nucleic acids) which has been approved for use in humans by the FDA or a similar government agency in another country, for any purpose.

Applicants reserve the right to exclude any particular compound, compounds, or compound class from the scope of "test compound" and/or from the compositions and methods of the invention. In some embodiments the "test compound" is not a compound found in, or known in the art as an ingredient of, tissue culture medium, e.g., a compound provided for purposes of culturing the cells. In some embodiments the test compound may be one found in, or known in the art as an ingredient of, tissue culture medium, but is used as a test compound at concentrations differing from those at which it is typically used as an ingredient of tissue culture medium. In some embodiments the compound is not a compound known in the art as being useful for treating cancer and/or for reducing side effects associated with chemotherapy.

Dihydropyrimidine Dehydrogenase (DYPD)

Dihydropyrimidine dehydrogenase (DPD, EC 1.3.1.2, encoded by the gene DYPD) is a pyrimidine catabolic enzyme and is the initial and rate-limiting enzyme in the pathway by which the pyrimidine bases uracil and thymine are degraded (FIG. 7). DPD catalyzes reduction of uracil and thymine to 5,6-dihydrouracil and 5,6-dihydrothymine, respectively. Dihydropyrimidinase (DHP, EC 3.5.2.2, encoded by the gene DPYS) then catalyzes the hydrolytic ring opening of the dihydropyrimidines. In the third step, the resulting N-carbamyl-β-alanine and N-carbamyl-β-aminoisobutyric acid are converted to β-alanine and 3-aminoisobutyric acid, ammonia and CO2 by β-ureidopropionase (UPB1, EC 3.5.1.6, encoded by the gene UPB1). β-alanine and β-aminoisobutyric acid are amino acids and are metabolized by amino acid metabolism pathways. Further information regarding DPD, DHP, and UPB1, including information regarding locations of various mutations that result in deficiencies of these enzymes in human patients and structural information derived in part from crystal structures of pig (DPD, DHP) or *Drosophila* (β-ureidopropionase) proteins, may be found in, e.g., the following papers and references cited therein: van Kuilenburg A B, et al., Novel disease-causing mutations in the dihydropyrimidine dehydrogenase gene interpreted by analysis of the three-dimensional protein structure. Biochem J. (2002) 364:157-63; van Kuilenburg A B, et al., Dihydropyrimidinase deficiency: Phenotype, genotype and structural consequences in 17 patients. Biochim Biophys Acta (2010) 1802(7-8):639-48; van Kuilenburg A B, et al., β-Ureidopropionase deficiency: Phenotype, genotype and protein structural consequences in 16 patients. Biochimica et Biophysica Acta (2012) 1822: 1096-1108.

In some embodiments, methods are provided herein for identifying a candidate agent for dihydropyrimidine dehydrogenase (DPD) dependent inhibition of an EMT. The methods generally involve exposing DPD to a test agent and assessing the enzymatic activity of DPD while exposed to a test agent, and determining whether exposure to test agent inhibits activity of the DPD. In some embodiments, the enzymatic activity of DPD assessed in the methods is comprises the catalytic reduction of a pyrimidine, for example, the catalytic reduction of uracil to 5,6-dihydrouracil and/or the catalytic reduction of thymine to 5,6-dihydrothymine. In some embodiments, the methods may involve determining whether the test agent inhibits an EMT in cells of epithelial origin. Thus, the test agent can be evaluated to determine whether or not it inhibits an EMT in a manner that depends (at least in part) on the expression of DPD in the cells.

The test agent can be further characterized with respect to its effects on other aspects of the DPD pathway in cells. Without wishing to be bound by any theory, Applicants propose that in some embodiments the effect of DPD in promoting EMT may not require activity of the downstream enzymes in the pyrimidine catabolism pathway (DHP and UPB1); DPD may act in EMT at least in part by affecting one or more biological activities of DPYSL2 and DPYSL3. The proteins encoded by DPYSL2 and DPYSL3 are members of a family of proteins known as collapsin response mediator proteins (CRMPs). DPYSL2 encodes CRMP2 (also known as dihydropyrimidinase-related protein 2) and DPYSL3 encodes CRMP4 (also known as dihydropyrimidinase-related protein 3). CRMPs are a family of five intracellular phosphoproteins that are most highly expressed in the nervous system during development and are implicated in neurite outgrowth and axonal guidance. RNAs encoding CRMPs 1-5 are alternatively spliced to yield shorter (~65 kDa) and longer forms (~80 kDa) containing N-terminal extensions. CRMPs likely exist as hetero-tetrameric complexes in vivo. CRMP1-CRMP4 bind to tubulin heterodimers and microtubules and play a role in cytoskeletal dynamics. CRMP4 has also been shown to promote F-actin bundling. While related in sequence to DPD, CRMPs lack known catalytic activity.

Without wishing to be bound by any theory, CRMPs, such as CRMP2 and CRMP4, may promote cytoskeletal reorganization associated with EMT, which may facilitate cancer cell invasion, migration, and/or metastasis. It is possible that one or more products generated as a result of DPD's action on uracil and/or thymine (e.g., 5,6 dihydrouracil and/or 5,6-dihydrothymine) may act as a modulator of activity of one or more CRMPs such as CRMP2 and/or CRMP4. While CRMPs lack known enzymatic activity they may contain pockets that accommodate binding of such compounds, which may result in, e.g., conformational change or alteration of protein-protein interaction(s). Such modulation may, for example, enhance the ability of CRMPs to promote cytoskeletal remodeling and/or one or more other processes that occurs during EMT.

Accordingly, the extent to which the expression or intracellular localization of a dihydropyrimidinase-related protein (e.g., CRMP2, CRMP4) is altered in response to the test agent can be evaluated. This assessment can provide insight on whether dihydropyrimidinase-related proteins are operative in the cells during the EMT and whether the test agent affects their activity. The methods may further involve, in some embodiments, a determination as to whether the cytoskeletal organization of cells is altered in response to being exposed to the test agent or whether the test agent affects invasiveness, migration ability, and/or one or more metastatic characteristics of cells.

Kits

Cells or agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents or cells described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of a kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit.

In some embodiments, a kit is provided that comprises one or more containers housing reagents for forcing expression in a cell of epithelial origin a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, in which at least one reagent comprises a nucleic acid encoding the metabolic mesenchymal gene; and instructions for forcing expression of the metabolic mesenchymal gene to induce the cell to undergo an epithelial to mesenchymal transition.

In some embodiments, a kit is provided that comprises one or more containers housing reagents for inhibiting expression or activity in the cell of a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3, in which at least one reagent comprises an inhibitory agent that inhibits expression or activity of the metabolic mesenchymal gene; and instructions for inhibiting expression or activity in the cell of a metabolic mesenchymal gene to induce the cell to undergo an epithelial to mesenchymal transition.

In some embodiments, a kit is provided that comprises one or more containers housing reagents for forcing expression in a cell of epithelial origin a metabolic mesenchymal gene selected from: QPRT, CYBA, PTER, MFNG, TM7SF2, PLCG2, ST6GAL1, CA2, GLB1L2, PIK3C2B, GCH1, ALDH1A1, GPX2, and GALNT3, in which at least one reagent comprises a nucleic acid encoding the metabolic mesenchymal gene; and instructions for forcing expression of the metabolic mesenchymal gene to inhibit or reverse an epithelial to mesenchymal transition in the cell.

In some embodiments, a kit is provided that comprises one or more containers housing reagents for inhibiting expression in the cell of a metabolic mesenchymal gene selected from: NNMT, GPX8, DSE, HS3ST3A1, DPYD, DPYSL2, DPYSL3, PAPSS2, GLT8D2, CYBRD1, GFPT2, ARSJ, EXT1, AOX1, PTGR1, MSRB3, BCAT1, GXYLT2, MICAL2, PAM, CYP1B1, PPAPDC1A, HAS2, DDAH1, SULF1, DSEL, PLCB4, MME, MGST1, PPAP2B, GBE1, COX7A1, GALNT10, UGCG, ENPP1, PDE1C, MGLL, UAP1, ENPP2, CHI3L1, SPHK1, CA12, B3GNT9, AK5, and AKR1B1, in which at least one reagent comprises an inhibitory agent that inhibits expression or activity of the metabolic mesenchymal gene; and instructions for inhibiting expression or activity in the cell of a metabolic mesenchymal gene to inhibit or reverse an epithelial to mesenchymal transition in the cell. In some embodiments, the inhibitory agent is an inhibitory oligonucleotide or a nucleic acid encoding an inhibitory RNA.

As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

Also provided herein are kits for evaluating the expression of metabolic mesenchymal genes. In some embodiments, kits are provided that comprise one or more containers housing at least two oligonucleotides, each of which oligonucleotides hybridizes to a different nucleic acid, in which each nucleic acid has a nucleotide sequence of a metabolic mesenchymal gene selected from Table 2. It should be appreciated that each of the one or more containers may house one or multiple different oligonucleotide types, and that for each type of oligonucleotide multiple copies may be housed in the container. The oligonucleotides are useful for detecting the presence in a sample of nucleic acid (e.g., mRNA, cDNA, cRNA, etc.) corresponding to a metabolic mesenchymal gene.

In some embodiments, a solid support (e.g., a bead or array substrate) is provided having immobilized thereto oligonucleotide probes consisting essentially of at least one, at least two or more different oligonucleotide probes each of which hybridizes to a different nucleic acid, in which each different nucleic acid has a nucleotide sequence of a metabolic mesenchymal gene selected from Table 2. It should be appreciated that the solid support may have multiple copies of each oligonucleotide probe directed against a particular one of the different nucleic acids so as to provide a suitable number of probes for detecting presence of a nucleic acid target in a sample. It should also be appreciated that, in some embodiments, the basic and novel property of these supports is that they are specifically tailored to assess the expression of metabolic mesenchymal genes without evaluating genes in other pathways. It should be appreciated, however, that in some embodiments, the solid support may comprise at least one control oligonucleotide probe that hybridizes to a control nucleic acid, such as a nucleic acid has a nucleotide sequence of a housekeeping gene (e.g., GAPDH, Beta-Actin). Presence of the control oligonucleotides probes permits comparisons to be made between different samples by providing a measurement for data normalization.

According to some aspects of the invention, arrays are provided that comprise, or consist essentially of, oligonucleotide probes that hybridize to nucleic acids having sequence correspondence to mRNAs of at least two, at least three, at least four, at least five, at least six, at least seven, at least eight, at least nine, at least ten or more genes selected from Table 2. Accordingly, provided herein are oligonucleotide (nucleic acid) arrays that are useful in the methods for determining levels of multiple nucleic acids simultaneously. Methods for producing nucleic acid arrays are well known in the art. For example, nucleic acid arrays may be constructed by immobilizing to a solid support large numbers of oligonucleotides, polynucleotides, or cDNAs capable of hybridizing to nucleic acids corresponding to mRNAs, or portions thereof. The skilled artisan is also referred to Chapter 22 "Nucleic Acid Arrays" of Current Protocols In Molecular Biology (Eds. Ausubel et al. John Wiley and #38; Sons NY, 2000), International Publication WO00/58516, U.S. Pat. No. 5,677,195 and U.S. Pat. No. 5,445,934 which provide non-limiting examples of methods relating to nucleic acid array construction and use in detection of nucleic acids of interest.

In some embodiments, kits are provided that comprise one or more containers housing at least two different antigen binding agents, each of which different antigen binding agents binds specifically to a protein product of a metabolic mesenchymal gene selected from Table 2. It should be appreciated that each of the one or more containers may house one or multiple different antigen binding agents, and that for each type of antigen binding agents multiple copies may be housed in the container. The oligonucleotides are useful for detecting the presence in a sample of a protein encoded by a metabolic mesenchymal gene.

In some embodiments, solid supports are provided having immobilized thereto antigen binding agents consisting essentially of at least one, at least two or more different antigen binding agents each of which binds specifically to a protein product of a metabolic mesenchymal gene selected from Table 2. It should be appreciated that the solid support may have multiple copies of each antigen binding agent directed against a particular one of the different proteins so as to provide a suitable number of antigen binding agents for detecting presence of a protein target in a sample. It should also be appreciated that, in some embodiments, the basic and novel property of these supports is that they are specifically tailored to assess the expression of proteins encoded by metabolic mesenchymal genes without evaluating proteins encoded by genes in other pathways. It should be appreciated, however, that in some embodiments, the solid support may comprise at least one control antigen binding agent that binds specifically to a control protein, such as the product of a house keeping gene. Presence of the control antigen binding agents permits comparisons to be made between different samples by providing a measurement for data normalization. In some embodiments, the antigen binding agents are antibodies or antigen-binding fragments thereof. According to some aspects of the invention, arrays are provided that comprise, or consist essentially of, antibodies that bind specifically to proteins encoded by at least two, at least three, at least four, at least five, at least six, at least seven, at least eight, at least nine, at least ten, or more genes listed in Table 2.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

All references described herein are incorporated by reference for the purposes described herein.

Exemplary embodiments of the invention will be described in more detail by the following examples. These embodiments are exemplary of the invention, which one skilled in the art will recognize is not limited to the exemplary embodiments.

Examples

Gene Profiling

A set of 1,704 human genes involved in various metabolic pathways was selected (Possemato et al., Nature. 2011 Aug. 18; 476(7360):346-50). Microarray-derived human gene expression data for these metabolic genes was obtained from several sources and was analyzed using unsupervised hierarchical clustering. Analysis showed that cancer cell lines demonstrate a cancer specific metabolic gene signature. It was found that cancer cell lines derived from a common tissue of origin (e.g., neuroectodermal; mesenchymal) generally cluster together based on their metabolic gene expression profile. One of the findings of this work is that certain cancer cell lines of non-mesenchymal origin (non-mesenchymally derived), including a number of cancer cell lines derived from a variety of carcinomas as well as from glioblastomas, display a metabolic gene signature characteristic of cancer cell lines of mesenchymal origin (mesenchymally derived cancer cell lines), as demonstrated by the fact that they cluster with mesenchymally-derived cancer cell lines (FIGS. 3A and 3B). Notably, high-grade hepatocellular cancer and breast cancer basal B cell lines cluster with mesenchymally-derived tumor cell lines (FIG. 3C). Mesenchymally-derived cancer cell lines as well as carcinoma cell lines that display a mesenchymal pattern of metabolic gene expression express known characteristic mesenchymal markers (FIG. 3D), confirming their mesenchymal phenotype. These results show that non-mesenchymally derived cancer cell lines that exhibit a mesenchymal phenotype can be identified based solely on their metabolic gene expression profile.

Metabolic Genes that Exhibit Different Expression Levels in Mesenchymally Derived Cancer Cell Lines Versus Non-Mesenchymally Derived Cancer Cell Lines A set of metabolic genes that exhibit different expression levels in mesenchymally derived cancer cell lines versus non-mesenchymally derived cancer cell lines was identified and designated as the "metabolic gene mesenchymal signature" (MGMS), sometimes referred to as "metabolic mesenchymal signature". These genes are listed in Table 2. Table 2 also indicates, for each MGMS gene, whether it exhibited increased expression (upregulated; red) or decreased expression (downregulated; green) in mesenchymally derived cancer cell lines. MGMS genes that exhibit increased expression in mesenchymally derived cancer cell lines as indicated in Table 2 may be referred to as "MGMS-upregulated genes". MGMS genes that exhibit decreased expression in mesenchymally derived cancer cell lines as indicated in Table 2 may be referred to as "MGMS-downregulated genes". Increased expression of the metabolic gene mesenchymal signature in mesenchymal cancers versus non-mesenchymal cancers was confirmed by analysis of expression data from primary tumors (FIG. 4A).

Assessment of MGMS-Related Gene Function

Using a pooled shRNA-based screen, certain of the MGMS-upregulated genes were demonstrated to play an important role in EMT (FIG. 5, S5). The screen utilized HMLE-TWIST cells, which contain a tamoxifen-activatable form of TWIST (Mani, S., et al., Cell. 2008 May 16; 133(4): 704-715). HMLE-TWIST cells normally undergo EMT following induction of TWIST activity with tamoxifen, causing them to express mesenchymal rather than epithelial markers. The screen is based on inhibiting (e.g., preventing) HMLE-TWIST cells from undergoing EMT upon induction of TWIST, as they normally would, by shRNA-mediated knockdown of genes whose expression promotes (e.g., is required for) EMT. HMLE-TWIST cells that do not undergo EMT upon tamoxifen treatment retain their expression of epithelial markers rather than exhibiting expression of mesenchymal markers.

To perform the screen, HMLE-TWIST cells were infected with a pooled shRNA library of about 500 different shRNAs, targeting 75 genes (some genes were represented by more than one shRNA). The 75 genes (listed in FIG. 13D) included 12 known mesenchymal genes, 42 of the 43 upregulated genes from the metabolic gene mesenchymal signature, 1 of the MGMS-downregulated genes, 16 randomly selected metabolic genes that are not part of the metabolic gene mesenchymal signature, and 4 control genes. After tamoxifen treatment, cell populations with mesenchymal or epithelial phenotypes were sorted by FACS based on their expression levels of CD44 and CD24. (Mesenchymal phenotype cell population was identified based on $CD44^{high}/CD24^{low}$. Epithelial phenotype cell population was identified based on $CD44^{low}/CD24^{high}$.) Genomic DNA was isolated from each group, and the abundance of the various shRNAs was determined by massively parallel sequencing and compared. ShRNAs that were underrepresented in the $CD44^{high}/CD24^{low}$ population (which has undergone EMT) as compared to the $CD44^{low}/CD24^{high}$ population (which has not undergone EMT) were identified. The genes corresponding to these shRNAs play a role in EMT, as demonstrated by the fact that inhibiting expression of these genes in HMLE-TWIST cells resulted in a marked reduction in the ability of these cells to undergo EMT following induction of TWIST activity with tamoxifen. MGMS genes that were identified in this work as affecting EMT are listed in the middle column of the table in FIG. 5D and are sometimes referred to as "MGMS-EMT genes".

One of the MGMS-EMT genes, DPYD, was selected for further study. It was shown that inhibiting expression of DPYD inhibits EMT but does not affect cell proliferation (FIG. 14C).

Assessment of DPYD in Epithelial to Mesenchymal Transition

To further investigate the mechanism by which DPYD acts in EMT, Applicants examined the expression of DPYS and UBP1 in HMLE-TWIST cells using quantitative PCR. Results were normalized to the expression level in human liver tissue. DPYS and UBP1 expression was not detected either in untreated HMLE-TWIST cells or in HMLE-TWIST cells that had been treated with tamoxifen for 15 days to induce EMT (FIG. 8A).

Applicants noticed that two genes in the metabolic gene mesenchymal signature, DPYSL2 and DPYSL3, encode proteins that are known to be related in sequence to DPD (the protein encoded by DPYD). Applicants examined expression of DPYSL2 and DPYSL3 in HMLE-TWIST cells. Consistent with their increased expression in mesenchymally derived cancers, expression of both DPYSL2 and DPYSL3 increased markedly in HMLE-TWIST cells after 15 days treatment with tamoxifen (FIG. 8B). FIG. 8C is a time course showing DPYSL2 and DPYSL3 expression in HMLE-TWIST cells during tamoxifen treatment relative to expression at time 0 (start of treatment) as determined using quantitative PCR.

TABLE 1

Universal metabolic genes segregated by metabolic pathways

| | | Pathways | Metabolic Enzymes |
|---|---|---|---|
| Nucleotide Biosynthesis | Purine | De novo | IMPDH1, PPAT, ATIC, GART, PAICS, PFAS, PNP |
| | | Salvage | ADK, ADA, HPRT1 |
| | Pyrimidine | De novo | CAD, CTPS, DTYMK, TYMS, NME1 |
| | | Salvage | TK1, UCK2 |

TABLE 1-continued

Universal metabolic genes segregated by metabolic pathways

| | | Pathways | Metabolic Enzymes |
|---|---|---|---|
| | Not Defined | Nucleotide<br>Folate | RRM1, RRM2, NUDT1,<br>NUDT5, NUDT15, NUDT21,<br>PRPS1<br>MTHFD1, MTHFD1L, MTHFD2<br>[ADCY4, CECR1, GMPR,<br>GUCY1A3, PDE2A, PDE9A,<br>ALDH1L1]<br>AK2, DCK, DGUOK, NT5DC2 |
| Lipids | Energy | Triacylglycerol Biosynthesis<br>Beta-Oxidation | ACYL, ACOT7, [PPAP2A,<br>PPAP2A, ACSS1]<br>[ACADVL] |
| | Structural | Cholesterol<br>Desaturated Fatty Acid<br>Ether Lipids<br>Phosphatidylcholine Biosynthesis | SQLE, ACAT2<br>ELOVL6, FADS1<br>AGPS, NCEH1<br>[CHKB] |
| | Signaling | Lipid Signaling<br>Prostanoid Biosynthesis<br>Arachidonic Acid | MNPP1, [ENPP2, ITPKB,<br>PIK3R1, PLA2G4C, PLCL1]<br>[PTGDS]<br>[EPHX2] |
| | Not Defined | | [CYP4F12, ECHDC2, ECHDC3,<br>PHYHD1, ACACB], SCD,<br>ACBD6 |
| Amino<br>Acids | Biosynthesis | Spermidine Biosynthesis<br>Amino Acid Biosynthesis<br>Creatine-Phosphate Biosynthesis<br>Selencyslaine Biosynthesis | SRM, ODC1<br>ASNS, AHCY, PSAT, PSPH,<br>SHMT2, [GLUL]<br>[CKM, CKMT2]<br>SEPHS1 |
| | Degradation | Spermidine Degradation<br>Amino Acid Degradation | [SAT1]<br>[GATM, ALDH6A1, AMT,<br>ACO3, BHMT2, CDO1, MAOA,<br>MAOB, ASPA] |
| Steroid | Biosynthesis | Bile Acid Biosynthesis<br>Androgen Biosynthesis<br>Steroid<br>Retinioc Acid<br>Thyroid Hormone Metabolism | [ACOX2, CYP27A1]<br>SRD5A1, SRD5A3, [AKR1C1]<br>SOAT1, ARSJ<br>THNSL2, [ALDH1A1, BCO2]<br>[SULT1A1] |
| | Degradation | Nicotine Degradation<br>Ethanol Degradation | [FMO2]<br>[ALDH2, ADH1B] |
| | Not Defined | | [ALOX5AP, HSD11B1,<br>HSD17B14] |
| Carbon | | Glycolysis<br>PPP<br>Glycerol-3-Phosphate shuttle<br>Citric Acid<br>Respiratory Chain<br>Glycogen Degradation | PFKP, PKM, ENO1, PGK1<br>G6PD, TKT, RPE<br>[GPD1, GPD1L]<br>[COX7A1, NDUFA4L2]<br>COQ2, PDSS1, [D2HGDH]<br>[PGM5] |
| Glycan | Biosynthesis | N-Glycan Biosynthesis<br>Glycosylphosphatidylinositol(GPI)-<br>Anchor<br>Dermatan Sulfate Biosynthesis | ALG8, C1GALT1, GALNT10,<br>MANEAL<br>PIGF, PIGW, PIGX<br>HS2ST1, [CSGALNACT1] |
| | Degradation | D-Glucuronate Degradation<br>Glycogen Degradation | [CRYL1]<br>PYGL, [PYGM] |
| | Not Defined | | AGK, FUT8, [MAN1C1] |
| Redox | | Glutathione Biosynthesis<br>Glutathione Redox Reactions<br>Glutathione Mediated<br>Detoxification<br>Redox<br>Thioredoxin Pathway | GCLM, GGH, [GSTT1, GGT5<br>GSTA4]<br>GPX8, [GPX3]<br>CYB5B, PRDX4, [EPHX1, SOD3]<br>GLRX2, GLRX3<br>TXNRD1 |
| Other | Co-Factor | Nicotinate and nicotinamide<br>metabolism<br>Carbonic Anhydrases<br>Thio-Molybdenum Cofactor<br>Biosynthesis | NQO1, [C9orf95, INMT,<br>CYP4X1]<br>[CA4]<br>MOCOS |
| | Not Defined | | ACN9, NAA50, FXN, [ADHFE1] |

Bold-Rate Limiting Enzymes
No Bracket = Up-regulated
Bracket = Down-regulated

TABLE 2

Metabolic mesenchymal signature genes segregated by metabolic pathway.

| | | Pathways | Metabolic Enzymes |
|---|---|---|---|
| Nucleotide Biosynthesis | Pyrimidine Nucleotide | Degradation | DPYD, DPYSL2, DPYSL3<br>AKS, ENPP1 |
| Lipids | Energy | Triacylglycerol Degradation | MGLL |
| | Structural | Cholesterol | [TM7SF2], AKR1B1 |
| | Signaling | Sphingosine | SPHK1, UGCG<br>ENPP2, PPAP2B, PPAPDC1A, PDE1C, PLCB4<br>PTGR1, [P1K3C2B, PLCG2, ALDH1A1] |
| Amino Acid | Degradation | Branched Amino Acid Degradation | BCAT1 |
| | | Amino Acid Degradation | CYP1B1 |
| | | Tetrahydrobioplerin Biosynthesis | [GCH1] |
| Carbon | TCA | | CYBRD, COX7A1, [CYBA] |
| Redox | Glutathione | | MGST1, GPX8, [GPX2] |
| Glycan | Beta-Galactose | | [ST6GAL1, GLB1L2] |
| | Dermatan Sulfate Biosynthesis | | DSE, DSEL |
| | Heparin Sulfate | | HS3ST3A1, EXT1 |
| | Sulfatases | | ARSJ, SULF1, PAPSS2 |
| | GlcNAc | | GFPT2, GALNT10, UAP1 |
| | Glycan | | GXYLT2, GBE1, GLT8D2, [GALNT3] |
| | Hyaluronan Synthease | | HAS2 |
| | Glyco Protein | | PAM, CHI3L1 |
| | Other | | B3GNT9, [MFNG] |
| CoFactor | Nicotineamid | | AOX1, NNMT, [QPRT] |
| Other | | | MICAL2, MME, DDAH1, MSRB3, [PTER]<br>CA12, [CA2] |

Bold-Rate Limiting Enzymes
No Brackets = Up-regulated
[Brackets] = Down-regulated DPYD Expression Promotes the EMT To further establish the role of DPYD in the EMT, HMLE-Twist-ER cells were individually infected with eight distinct shRNAs targeting DPYD and found that DPYD knockdown decreased the percentage of cells with a mesenchymal profile ($CD24^{low}/CD44^{high}$) after OHT treatment in a dose-dependent manner (FIG. 15A). DPYD knockdown with the hairpins shDPYD_1 and shDPYD_4, which most strongly reduced DPYD expression (FIG. 15B), did not affect cell viability (FIG. 15C) but did decrease the percentage of cells with a mesenchymal profile (FIG. 16A) as well as suppress the expression of ZEB1 and vimentin (VIM) (FIGS. 16B and 15D). Moreover, DPYD knockdown also decreased the capacity of the cells to form mammospheres, a unique capacity of the mesenchymal-like ($CD24^{low}/CD44^{high}$) but not epithelial ($CD24^{high}/CD44^{low}$) HMLE cells (FIG. 16C). Thus, this functional assay confirmed that a reduction in DPYD expression inhibits the EMT.

To confirm that the effects of the DPYD shRNAs are not due to off-target effects, DPYD levels were restored in shDPYD-expressing HMLE-Twist-ER cells by ectopically expressing the mouse isoform of DPYD (mDPYD), which is 86% identical to the human isoform but unaffected by the shRNAs targeting human DPYD (FIG. 15E). Expression of mDPYD in the presence of shDPYD_1 fully restored EMT induction to the level observed in controls (FIG. 16D). Additionally, in these cells the expression of the mesenchymal markers ZEB1 and VIM (FIG. 16E) and the capacity for mammosphere formation (FIG. 16F) were also restored. Ectopic expression of mDPYD increased the percentage of mesenchymal-like cells relative to the empty-vector control (FIG. 16D, compare the top left and bottom left panels), indicating that the expression level of DPYD is a limiting factor in regulating the EMT process. Thus, DPYD expression is elevated during the EMT and plays an role in this process.

Cellular Dihydropyrimidine Levels are Elevated During EMT

Having demonstrated that DPYD expression plays a critical role in the EMT, the extent to which its metabolic products increase in abundance during this process was assessed. To do so, liquid chromatography and mass spectrometry (LC-MS) were used to determine the cellular concentration of DPYD substrates (uracil and thymine) and products (dihydrouracil and dihydrothymine) (FIG. 17A). In HMLE-Twist-ER cells, overexpression or knockdown of DPYD resulted in a corresponding ~10-fold increase or decrease, respectively, in the intracellular DHU/uracil molar ratio (FIG. 17B). Moreover, NAMEC cells had higher DHU/uracil and DHT/thymine ratios than HMLE-Twist-ER cells (by 10- and 6-fold, respectively; FIGS. 17B and 18A), consistent with the higher endogenous DPYD expression level in the former cells (FIG. 19A). In addition, OHT treatment of HMLE-Twist-ER cells, which progressively upregulates DPYD expression (FIGS. 19B and 19A) gradually increased the cellular DHU/uracil molar ratio by 5-fold (FIG. 17C). DPYD expression and DHU/uracil ratios were also correlated in breast cancer and HCC cell lines (FIGS. 17D and 17E). Notably, the higher DHU/uracil molar ratio in MCF7 breast cancer cells compared to the other luminal cell lines (FIG. 17D) correlates with the relatively high expression of DPYD in these cells (FIG. 19C). Thus, DHU/uracil ratios correlate closely with DPYD expression levels and mesenchymal character in a number of cellular settings, indicated that DPYD is enzymatically active in the cancer cell lines examined.

DPYD is normally expressed in the liver, where it is the rate-limiting enzyme of a three-step pyrimidine degradation pathway that converts uracil and thymine to β-alanine and 2-methyl-β-alanine, respectively (FIG. 17A). In the liver, the products of DPYD are further catabolized by dihydropyrimidinase (DPYS) and beta-ureidopropionase (UPB1) (FIG. 17A). It was determined that HMLE-Twist-ER and NAMEC cells express DPYD, but not certain other components of the pathway (FIG. 18B). In addition, unlike DPYD expression, DPYS and UPB1 expression is not elevated in breast Basal B and high-grade HCC cell lines (FIG. 18C). These observations are consistent with DPYD products accumulating in mesenchymal-like cancer cells, but not under normal physiological conditions.

DPYD Enzymatic Activity Supports EMT

The accumulation of DPYD products in mesenchymal-like cells suggests that its function in the EMT is mediated through its enzymatic activity. Thus, the ability of the catalytically attenuated mouse DPYD mutant (mDPYD-I560S, also known as DPYD*13) to rescue the inhibitory effect of shDPYD_1 on EMT induction was assessed. Whereas expression of wild-type mDPYD in the presence of shDPYD_1 restored the EMT induction following OHT treatment, mDPYD-I560S had a greatly capacity to rescue CD44/CD24 expression and mammosphere formation, and completely failed to restore ZEB1 expression (FIG. 20A-C). In addition, it was determined that, while control cells treated with OHT for only 10 days displayed an intermediate marker expression profile, cell lines ectopically expressing either mouse or human DPYD (DPYD-FLAG) displayed higher mesenchymal marker expression at this time point (FIG. 20D), resembling the profile of control cells after 15 days of treatment (FIG. 20A). In contrast to wild-type DPYD, overexpression of the mutant DPYD-I560S had a greatly attenuated effect on cell-surface marker expression and mammosphere formation, while preventing ZEB1 expression (FIG. 20D-F). Thus, the function of DPYD in the EMT program requires its enzymatic activity; moreover, the accelerated kinetics of EMT in DPYD-overexpressing cells suggests that DPYD products may be rate-limiting in this process.

To further confirm the role of DPYD products in the EMT, the extent to which exogenous addition of these metabolites could substitute for DPYD loss was assessed. Indeed, treatment of shDPYD_1 cells with DHU or DHT resulted in a dose-dependent rescue of mammosphere formation (FIG. 20G), whereas the DPYD substrate uracil had a significantly smaller effect (FIG. 21), despite the fact that uracil and DHU accumulated to comparable intracellular concentrations (data not shown). Therefore, the effect of DPYD knockdown on mammosphere formation can be rescued either by ectopic expression of active DPYD (FIGS. 16F and 20C) or by adding its products to cells. Together, these results confirm that the MMS gene DPYD plays a critical role in the EMT via its enzymatic activity and dihydropyrimidine production.

Methods:

Antibodies

Antibodies were obtained from the following sources: Epithelial-Mesenchymal Transition (EMT) Antibody Sampler Kit (89782) (includes antibodies for ZEB1, VIM, CDH1, and SLUG), DPYD (4654), and Actin (3700) from Cell Signaling Technology; FITC-labeled anti-CD24 (555427), and APC-labeled anti-CD44 (559942) from BD Bioscience; HRP-labeled anti-mouse and anti-rabbit secondary antibodies from Santa Cruz Biotechnology.

Cell Lines and Cell Culture

The immortalized human mammary epithelial cells expressing ectopic Twist-ER (HMLE-Twist-ER) and Naturally Arising MEsenchymal Cells (NAMECs) were used. HMLE-Twist-ER and NAMEC cells were maintained in MEGM (Lonza) growth media. The cell lines ZR-75-1, EVSA-T, MCF7, MDA-MB-231, MDA-MB-157, Hs-578-T, HEPG2, SNU-387, and SNU-432 were obtained from ATCC and were maintained in DMEM supplemented with 10% IFS. All cells were cultured at 37° C. with 5% $CO_2$. For EMT induction, HMLE-Twist-ER cells were treated with 4-hydroxytamoxifen (OHT) (Sigma, H7904) at a final concentration of 10 nM for the indicated number of days.

Cancer Cell Line Gene Expression Matrix and Median of Median Determination

Cancer cell line gene expression data were collected from (1) Cancer Cell Line Encyclopedia (CCLE), (2) GlaxoSmithKline (GSK) cell line data (cabig.nci.nih.gov/caArray_GSKdata/), (3) and Gene Expression Omnibus database (GEO). Data were normalized by RMA using the Affymetrix package from Bioconductor. A custom probeset definition was used for processing the arrays as defined by Dai M et al such that there was one probeset per Entrez Gene I D. The cell lines were classified based on their tissue of origin (with the exception of breast and lung cell lines, which were further divided based on Estrogen Receptor status (for breast) or SLC and NSCLC (lung)), resulting in 22 different groups. In order to avoid bias toward tissues that are represented by a large number of cell lines, we calculated the cancer cell lines median in two steps. First, the median expression value for each gene among the cancer cell lines from a single tissue of origin was calculated, resulting in one value for each gene in each tissue of origin. Second, these tissue-of-origin median values were combined, and their median was determined to obtain the "cancer cell line median of medians" value for each gene. The relative gene expression level for each metabolic gene in each cell line was calculated as the ratio of its expression level to the corresponding median of median value.

Primary Tumor Gene Expression Matrix and Median of Median Determination

Primary tumor gene expression data were collected from (1) "Expression Project for Oncology" (intgen.org/expo/) and (2) Gene Expression Omnibus database (GEO). Data were normalized by RMA using the Affymetrix package from Bioconductor. A probeset definition was used for processing the arrays such that there was one probeset per Entrez Gene I D. The calculation for the primary tumor median of medians was conducted similarly to that of cancer cell lines median of medians.

Identification of the Metabolic Mesenchymal Signature (MMS) Genes

For each metabolic gene, the ratio between the mean expression level in mesenchymal (mesenchymal group) and non-mesenchymal cell lines (all other groups) was determined. The mean and standard deviation of all the metabolic gene expression ratios was calculated, and all genes upregulated above a Z-score of 2.5 or below a Z-score of −2 were classified as MMS.

Fluorescence-Activated Cell Sorting (FACS) Analysis

Cells were prepared according to standard protocols and suspended in 1% Serum/PBS on ice prior to FACS. 7-AAD (Life Technologies) was used to exclude dead cells. Cells were sorted on a BD FACSAria or analyzed using the FACSCalibur HTS (BD Biosciences) with FlowJo software (Tree Star, Ashland, Oreg.).

RNA Preparation and RT-PCR Analysis

Total RNA was isolated from cells or tissues using the RNeasy Kit (Qiagen, 74106) and reverse-transcription was performed using Superscript III reverse transcriptase (Invitrogen, 18080-044). The resulting cDNA was diluted in DNase-free water (1:10) before quantification by real-time quantitative PCR. mRNA transcription levels were measured using SYBR Green PCR master mix (Applied Biosystems, 430955) and Biosystems 7900HT sequence Detection System v2.3 software. All data are expressed as the ratio between the expression level of the target gene mRNA and that for Actin. Primers used for qRT-PCR were obtained from Integrated DNA Technology and are listed in the table below. Human adult liver total RNA was from Cell Application (1H21-50).

| Genes | SEQ ID NO: Forward | | SEQ ID NO: Reverse | |
|---|---|---|---|---|
| CYBRD1 | 1 | TCGTCTGGGTCCTCCACTAC | 18 | TGGCAGCAACTGCATTTAAC |
| DPYD | 2 | GTGTTCCACTTCGGCCAAGAA | 19 | GAGTCGTGTGCTTGATGTCAT |
| DSE | 3 | GGGCTCCAGTGTGTTTTTCA | 20 | GTCGGTGATGTAGGCTGACA |
| DSEL | 4 | GGCCTTGGTGACTGGAGTAG | 21 | GCTGGGCCAGAAAAACATAC |
| GPX8 | 5 | ACTTCAGCGTGTTGGCTTTT | 22 | AGGCCTGATGACTTCAATGG |
| GXYLT2 | 6 | GCTTGGGAGGACATGTTGTA | 23 | CAGTGATCGGGACGGTAGTT |
| HS3ST3A1 | 7 | TGGAGAAGACGCCCAGTTAC | 24 | GACAGCGTCTGCGTGTAGTC |
| MME | 8 | AGAAGAAACAGCGATGGACTCC | 25 | CATAGAGTGCGATCATTGTCACA |
| NNMT | 9 | GACATCGGCTCTGGCCCCACT | 26 | GACATCGGCTCTGGCCCCACT |
| PPAP2B | 10 | TGAGAGCATCAAGTACCCACT | 27 | ACGTAGGGGTTCTGAATCGTC |
| HAS2 | 11 | CTCTTTTGGACTGTATGGTGCC | 28 | AGGGTAGGTTAGCCTTTTCACA |
| ZEB1 | 12 | TGCACTGAGTGTGGAAAAGC | 29 | TGGTGATGCTGAAAGAGACG |
| CDH1 | 13 | TTGCACCGGTCGACAAAGGAC | 30 | TGGATTCCAGAAACGGAGGCC |
| VIM | 14 | ACCCGCACCAACGAGAAGGT | 31 | ATTCTGCTGCTCCAGGAAGCG |
| DPYS | 15 | ATTGATTTCGCCATTCCTCAGAA | 32 | GCTGTAGTCGCAGCAAACTTT |
| UPB1 | 16 | GCGCGTTCTCTATGGCAAG | 33 | CCGCTGCTTCAAAGGCATATC |
| TWIST | 17 | TGCGGAAGATCATCCCCACG | 34 | GCTGCAGCTTGCCATCTTGGA |

Pooled shRNA Screen pLKO.1 lentiviral plasmids encoding shRNAs targeting 74 genes were obtained and combined to generate a plasmid pool. HMLE cells were infected with the pooled lentivirus so as to ensure that each cell contained only one viral integrant. Cells were selected for 3 days with 0.5 mg/ml puromycin, after which $10^6$ cells were removed, washed, and frozen at −80° C. (FIG. 3A, day 0). The remaining cells were split into OHT-treated and untreated samples. After 15 days, the OHT-treated cells were trypsinized, washed with phosphate buffered saline (PBS)+1% inactivated fetal calf (IFC) serum, and FACS-sorted using CD44/CD24 antibodies in order to separate the mesenchymal and epithelial populations.

Genomic DNA was isolated from all the cells using the QIAampDNA mini kit (Qiagen). To amplify the shRNAs encoded in the genomic DNA, PCR was performed for 33 cycles at an annealing temperature of 66° C. using 3.5 μg of genomic DNA, the primer pair indicated below, and DNA polymerase (TAKARA EX Clontech lab). Forward primers containing unique 2-nucleotide barcodes were used so that PCR products obtained from many samples could be sequenced together. After purification, the PCR products from each cell sample were quantified by ethidium bromide staining (Sigma) after gel electrophoresis, pooled in equal proportions, and analyzed by high-throughput sequencing (Illumina). The shRNAs from all 4 DNA samples (day 0, day 15 untreated, day 15 OHT-treated mesenchymal, and day 15 OHT-treated epithelial) were sequenced together. Sequencing reads were de-convoluted using GNU Octave software by segregating the sequencing data by barcode and matching the shRNA stem sequences to those expected to be present in the shRNA pool, allowing for mismatches of up to 3 nucleotides. The $\log_2$ values reported are the average $\log_2$ of the fold change in the abundance of each shRNA in the mesenchymal-like samples compared to epithelial cells. The mean and standard deviation of the control hairpins (GFP, RFP, Luciferase, LacZ) were calculated and used to set a cutoff (one standard deviation below the control mean). Every gene that had at least two hairpins with a $\log_2$ value below the cutoff was considered a hit.

Mammosphere Assay 500 cells/well were seeded in 96-well ultra-low adhesion plates (Corning, 3474) in MammoCult Basal Medium (Stem Cell Technology, 05621) containing 2.6% methylcellulose (Stem Cell Technology, H4100) and 10% MammoCult Proliferation Supplements (Stem Cell Technology, 05621), supplemented with 0.5 μg/ml hydrocortisone, 4 μg/ml Heparin and Pen/strep. Spheres were counted 12-14 days later.

Metabolite Extraction

Solvents were obtained from Fisher Scientific and were Optima LC/MS grade except where otherwise specified. Cells grown in standard tissue culture plates (500,000 cells per sample) were washed twice in an ice-cold solution of 0.9% NaCl in deionized water, followed by extraction on dry ice in 1 mL 80% methanol containing 10 ng/mL phenylalanine-$d_8$ and valine-$d_8$ (Sigma-Aldrich) as internal standards. The cell mixtures were shaken vigorously on a Vortex mixer for 10 min. at 4° C., vacuum-dried, and resuspended in 100

µL LC/MS grade water (Fisher). These extracts were then centrifuged at 15,000×g at 4° C. for 10 min, and the supernatants were passed through a cellulose acetate particulate filter (National Scientific).

Liquid Chromatography (LC) Analysis

An UltiMate 3000 UPLC system with autosampler (Dionex) was used for this study. Biological triplicate samples (typically 10 µL) were injected onto an Atlantis dC18 2.1×150 mm (3 µm particle size) column (Waters) and eluted isocratically in a mobile phase consisting of 1 mM ammonium acetate, 5 mM formic acid, and 3.3% methanol (mobile phase A) at a flow rate of 0.2 mL/min. The run time was 19 min; the autosampler was held at 4° C. and the column compartment was held at 12.5° C. To minimize carryover, blank injections were performed after every six analytical runs. In addition, after every 12 analytical runs, the column was cleaned with a gradient from 100% mobile phase A to 100% acetonitrile over 10 min, followed by 15 min. at 100% acetonitrile, and finally by 15 min re-equilibration in 100% mobile phase A, all at 0.2 mL/min.

Mass Spectrometry (MS) Analysis

The UPLC system was coupled to a QExactive orbitrap mass spectrometer equipped with a HESI II probe (Thermo Fisher Scientific) operating in positive ion mode. The spray voltage was set to 3.9 kV, and the heated capillary and the HESI probe were both held at 270° C. The sheath gas flow was set to 28 units, the auxiliary gas flow was set to 13 units, and the sweep gas flow was set to 5 units. External mass calibration was performed every 7 days. The MS data acquisition was performed by targeted Selected Ion Monitoring (tSIM) of the metabolites of interest and the internal standards, with the resolution set at 35,000, the AGC target at $10^5$, the maximum injection time at 250 msec, and the isolation window at 1.0 m/z. The full scan range was 70-1000 m/z. Quantitation of the data was performed with XCalibur QuanBrowser 2.2 (Thermo Fisher Scientific) using a 5 ppm mass tolerance, by a researcher blinded to the identity of the samples. Pure thymine (T0376), and uracil (U1128) were obtained from Sigma-Aldrich and dihydrothymine (L01996), and dihydrouracil (L01918) were obtained from Alfa Aesar and were run in half-log serial dilution (3 nM-100 µM) to confirm chromatographic retention times and generate standard curves for quantitation of each analytical batch.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for inhibiting or reversing an epithelial to mesenchymal transition in a cell of epithelial origin, the method comprising:
   inhibiting expression in the cell of the metabolic mesenchymal gene DPYD, thereby inhibiting or reversing an epithelial to mesenchymal transition in the cell, and wherein expression of the metabolic mesenchymal gene is inhibited in the absence of exposure of the cell to 5'fluorouracil.

2. The method of claim 1, wherein inhibiting expression comprises accumulating in the cell an exogenous inhibitory RNA that inhibits the metabolic mesenchymal gene.

3. The method of claim 1, wherein the cell of epithelial origin is a cancer cell.

4. The method of claim 1, wherein the cell of epithelial origin is in vivo.

5. The method of claim 1, wherein the cell of epithelial origin is in vitro.

6. The method of claim 1 further comprising determining the extent to which inhibition of the metabolic mesenchymal gene affects invasiveness, migration ability, and/or one or more metastatic characteristics of the cell of epithelial origin.

7. The method of claim 1 further comprising assaying activity of the metabolic mesenchymal gene in the cell of epithelial origin.

8. The method of claim 1 further comprising assaying alterations in the growth and/or survival of the cell of epithelial origin.

9. The method of claim 1, wherein the cell is of breast epithelial origin and wherein the method further comprises assessing the extent to which the cell is capable of mammosphere formation.

10. The method of claim 1 further comprising evaluating one or more epithelial markers on the cell.

11. The method of claim 1 further comprising determining whether the cell acquires a $CD44^{low}/CD24^{high}$ expression profile.

12. The method of claim 1 further comprising determining dihydrouracil (DHU) and/or uracil levels in the cell.

13. The method of claim 1 further comprising determining a molar ratio of dihydrouracil (DHU) to uracil in the cell.

14. The method of claim 1, wherein the cell is a breast cancer cell.

15. The method of claim 14, wherein the breast cancer cell is a basal subtype-B breast cancer cell.

16. The method of claim 1, wherein the cell is a hepatocellular carcinoma (HCC) cancer cell.

17. The method of claim 16, wherein the HCC cancer cell is of a high grade cancer.

* * * * *

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tcgtctgggt cctccactac                                                    20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
gtgttccact tcggccaaga a                                                  21

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
gggctccagt gtgttttca                                                     20

<210> SEQ ID NO 4
```

-continued

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ggccttggtg actggagtag                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
acttcagcgt gttggctttt                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
gcttgggagg acatgttgta                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
tggagaagac gcccagttac                                               20

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
agaagaaaca gcgatggact cc                                            22

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 9
gacatcggct ctggccccac t                                             21

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
```

```
tgagagcatc aagtacccac t                                            21

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
ctcttttgga ctgtatggtg cc                                           22

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tgcactgagt gtggaaaagc                                              20

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
ttgcaccggt cgacaaagga c                                            21

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
acccgcacca acgagaaggt                                              20

<210> SEQ ID NO 15
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 15
attgatttcg ccattcctca gaa                                          23

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 16
gcgcgttctc tatggcaag                                               19

<210> SEQ ID NO 17
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 17
tgcggaagat catccccacg                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
tggcagcaac tgcatttaac                                                    20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
gagtcgtgtg cttgatgtca t                                                  21

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gtcggtgatg taggctgaca                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
gctgggccag aaaaacatac                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
aggcctgatg acttcaatgg                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
cagtgatcgg gacggtagtt                                                    20
```

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
gacagcgtct gcgtgtagtc                                            20

<210> SEQ ID NO 25
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 25
catagagtgc gatcattgtc aca                                        23

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 26
gacatcggct ctggccccac t                                          21

<210> SEQ ID NO 27
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 27
acgtaggggt tctgaatcgt c                                          21

<210> SEQ ID NO 28
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 28
agggtaggtt agccttttca ca                                         22

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
tggtgatgct gaaagagacg                                            20

<210> SEQ ID NO 30
<211> LENGTH: 21
<212> TYPE: DNA
<213> ORGANISM: Artificial Sequence
<220> FEATURE:

```
<223> OTHER INFORMATION: Synthetic Oligonucleotide

<400> SEQUENCE: 30
tggattccag aaacggaggc c                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 31
attctgctgc tccaggaagc g                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 32
gctgtagtcg cagcaaactt t                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 33
ccgctgcttc aaaggcatat c                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 34
gctgcagctt gccatcttgg a                                              21

<210> SEQ ID NO 35
<211> LENGTH: 21
<212> TYPE: DNA
<213> ORGANISM: Homo sapiens

<400> SEQUENCE: 35
gctgtccaac taatcttgat a                                              21

<210> SEQ ID NO 36
<211> LENGTH: 21
<212> TYPE: DNA
<213> ORGANISM: Mus musculus

<400> SEQUENCE: 36
gctgtcccac atctcttgac a                                              21
```